United States Patent
Ando et al.

(10) Patent No.: US 11,334,770 B1
(45) Date of Patent: May 17, 2022

(54) PHENOTYPE ANALYSIS OF CELLULAR IMAGE DATA USING A DEEP METRIC NETWORK

(71) Applicant: Google LLC, Mountain View, CA (US)

(72) Inventors: Dale M. Ando, South San Francisco, CA (US); Marc Berndl, Mountain View, CA (US)

(73) Assignee: Google LLC, Mountain View, CA (US)

( * ) Notice: Subject to any disclaimer, the term of this patent is extended or adjusted under 35 U.S.C. 154(b) by 136 days.

(21) Appl. No.: 16/983,136

(22) Filed: Aug. 3, 2020

Related U.S. Application Data

(63) Continuation of application No. 16/133,542, filed on Sep. 17, 2018, now Pat. No. 10,769,501, which is a
(Continued)

(51) Int. Cl.
*G06K 9/62* (2022.01)
*G06N 3/08* (2006.01)
(Continued)

(52) U.S. Cl.
CPC ......... *G06K 9/6267* (2013.01); *G06K 9/6215* (2013.01); *G06K 9/6228* (2013.01);
(Continued)

(58) Field of Classification Search
CPC .. G06K 9/6267; G06K 9/6215; G06K 9/6228; G06K 9/6257; G06K 9/6288;
(Continued)

(56) References Cited

U.S. PATENT DOCUMENTS

| 5,733,721 A | 3/1998 | Hemstreet, III et al. |
| 6,789,069 B1 | 9/2004 | Barnhill et al. |

(Continued)

FOREIGN PATENT DOCUMENTS

WO  2019178322 A1  9/2019

OTHER PUBLICATIONS

Weakly Supervised Learning of Single-Cell Feature Embeddings Juan C. Caicedo, et al; available at https://doi.org/10.1101/293431; preprint uploaded to bioRxiv (biorxiv.org) on Apr. 2, 2018.
(Continued)

*Primary Examiner* — Brenda C Bernardi
(74) *Attorney, Agent, or Firm* — McDonnell Boehnen Hulbert & Berghoff LLP

(57) ABSTRACT

The present disclosure relates to phenotype analysis of cellular image data using a deep metric network. One example embodiment includes a method. The method includes receiving a target image of a target biological cell having a target phenotype. The method also includes obtaining a semantic embedding associated with the target image. The semantic embedding is generated using a machine-learned, deep metric network model. Further, the method includes obtaining, for each of a plurality of candidate images of candidate biological cells each having a respective candidate phenotype, a semantic embedding associated with the respective candidate image. In addition, the method includes identifying, for each of the semantic embeddings, common morphological variations and reducing, for each of the semantic embeddings based on the identified common morphological variations, effects of nuisances. Even further, the method includes determining, by the computing device, a similarity score for each candidate image.

24 Claims, 32 Drawing Sheets

Related U.S. Application Data continuation-in-part of application No. 15/808,699, filed on Nov. 9, 2017, now Pat. No. 10,467,754, which is a continuation-in-part of application No. 15/433,027, filed on Feb. 15, 2017, now Pat. No. 10,134,131.

(51) Int. Cl.
| | |
|---|---|
| *G06V 30/262* | (2022.01) |
| *G01N 33/48* | (2006.01) |
| *G01N 33/20* | (2019.01) |
| *G06V 20/69* | (2022.01) |

(52) U.S. Cl.
CPC ......... *G06K 9/6257* (2013.01); *G06K 9/6288* (2013.01); *G06N 3/08* (2013.01); *G06V 30/274* (2022.01); *G01N 33/20* (2013.01); *G01N 33/48* (2013.01); *G06V 20/698* (2022.01); *G06V 2201/10* (2022.01)

(58) Field of Classification Search
CPC ............... G06K 9/726; G06K 9/00147; G06K 2209/27; G06N 3/08; G01N 33/20; G01N 33/48
See application file for complete search history.

(56) References Cited

U.S. PATENT DOCUMENTS

| | | | | |
|---|---|---|---|---|
| 9,183,384 | B1* | 11/2015 | Bruhmuller | ............ G06N 20/00 |
| 10,146,914 | B1 | 12/2018 | Victors et al. | |
| 10,281,456 | B1 | 5/2019 | Victors et al. | |
| 2002/0111742 | A1 | 8/2002 | Rocke et al. | |
| 2005/0209785 | A1 | 9/2005 | Wells et al. | |
| 2006/0050946 | A1 | 3/2006 | Mitchison et al. | |
| 2006/0204103 | A1* | 9/2006 | Mita | ...................... G06K 9/6256 |
| | | | | 382/190 |
| 2010/0166266 | A1 | 7/2010 | Jones et al. | |
| 2013/0116215 | A1 | 5/2013 | Coma et al. | |
| 2015/0071541 | A1 | 3/2015 | Qutub et al. | |
| 2015/0268822 | A1* | 9/2015 | Waggoner | ............... G06F 3/167 |
| | | | | 715/722 |
| 2016/0364522 | A1 | 12/2016 | Frey et al. | |
| 2017/0372224 | A1 | 12/2017 | Reimann | |
| 2018/0084198 | A1 | 3/2018 | Kumar et al. | |
| 2018/0089534 | A1 | 3/2018 | Ye | |
| 2018/0260687 | A1* | 9/2018 | Kanno | .................. G06N 3/0454 |
| 2018/0314716 | A1* | 11/2018 | Kim | ...................... G06T 1/0007 |
| 2018/0322660 | A1* | 11/2018 | Smith | .................. G06K 9/6267 |
| 2018/0350067 | A1 | 12/2018 | Hamilton | |
| 2019/0192880 | A1* | 6/2019 | Hibbard | ............... A61N 5/1039 |
| 2019/0304568 | A1* | 10/2019 | Wei | ........................ G16B 40/20 |

OTHER PUBLICATIONS

"Using Deep Learning to Enhance Cancer Diagnosis and Classification", Rasool Fakoor, et al; Conference Paper, Jun. 2013.
"Machine Learning in Cell Biology—Teaching Computers to Recognize Phenotypes"; Christoph Sommer, et al.; Journal of Cell Science, 126 (24), pp. 5529-5539; Nov. 2013.
"A Comparison of Machine Learning Algorithms for Chemical Toxicity Classification using a Stimulated Multi-scale Data Model"; Richard Judson, et al.; BMC Bioinformatics, 9:241; May 19, 2008.
"Enhanced CellClassifier: a Multi-class Classification Tool for Microscopy Images"; Benjamin Misselwitz, et al.; BMC Bioinformatics, 11:30; Jan. 14, 2010.
"Approaches to Dimensionality Reduction in Proteomic Biomarker Studies"; Melanie Hilario, et al.; Briefings in Bioinformatics, vol. 9, No. 2, pp. 102-118; Feb. 29, 2008.
"Automatic Identification of Subcellular Phenotypes on Human Cell Arrays"; Christian Conrad, et al.; Genome Research 14, pp. 1130-1136; Jun. 2004.
"Machine Learning and Its Applications to Biology"; Adi L. Tarca, et al.; PLoS Computational Biology, vol. 3, Issue 6, pp. 0953-0963; Jun. 2007.
"Pattern Recognition Software and Techniques for Biological Image Analysis"; Lior Shamir, et al.; PLoS Computational Biology, vol. 6, Issue 11, pp. 1-10; Nov. 24, 2010.
"Computational Phenotype Discovery Using Unsupervised Feature Learning over Noisy, Sparse, and Irregular Clinical Data"; Thomas A. Lasko, et al.; PLoS ONE, vol. 8, Issue 6, pp. 1-13; Jun. 24, 2013.
"Scoring Diverse Cellular Morphologies in Image-Based Screens with Iterative Feedback and Machine Learning"; Thouis R. Jones, et al.; PNAS, vol. 16, No. 6, pp. 1826-1831; Feb. 10, 2009.
"Analyzing Array Data Using Supervised Methods"; Markus Ringnér, et al.; Pharmacogenomics 3(3), pp. 403-415; May 2002.
"Development and Validation of a Deep Learning Algorithm for Detection of Diabetic Retinopathy in Retinal Fundus Photographs"; Varun Gulshan, et al.; JAMA 316(22), pp. 2402-2410; Nov. 29, 2016.
"Learning Fine-grained Image Similarity with Deep Ranking"; Jiang Wang, et al.; 2014 IEEE Conference on Computer Vision and Pattern Recognition (CVPR); Conference Dates: Jun. 23-28, 2014; Date Accessible Online: Sep. 25, 2014.
"Comparison of Methods for Image-based Profiling of Cellular Morphological Responses to Small-molecule Treatment"; Vebjorn Ljosa, et al.; Journal of Biomolecular Screening 18(10), pp. 1321-1329; Sep. 17, 2013.
"FaceNet: A Unified Embedding for Face Recognition and Clustering"; Florian Schroff, et al.; 2015 IEEE Conference on Computer Vision and Pattern Recognition (CVPR); Conference Dates: Jun. 7-12, 2015; Date Accessible Online: Oct. 15, 2015.
"The Why and How of Phenotypic Small-Molecule Screens"; Ulrike S. Eggert; Nature Chemical Biology, vol. 9, No. 4, pp. 206-209; Mar. 18, 2013.
"When Quality Beats Quantity: Decision Theory, Drug Discovery, and the Reproducibility Crisis"; Jack W. Scannell, et al.; PLoS ONE 11(2); Feb. 10, 2016.
"Pipeline for Illumination Correction of Images for High-Throughput Microscopy"; Shantanu Singh, et al.; Journal of Microscopy; vol. 256, Issue 3, pp. 231-236; Sep. 16, 2014.
"High-Content Phenotypic Profiling of Drug Response Signatures across Distinct Cancer Cells"; Peter D. Caie, et al.; Molecular Cancer Therapeutics; vol. 9, Issue 6, pp. 1913-1926; Jun. 1, 2010.
"Annotated High-Throughput Microscopy Image Sets for Validation"; Vebjorn Ljosa, et al.; Nature Methods 9(7); Published Online Jun. 28, 2012.
"Automating Morphological Profiling with Generic Deep Convolutional Networks"; Nick Pawlowski, et al.; bioRxiv preprint—http://dx.doi.org/10.1101/085118; Published Online Nov. 2, 2016.
"Visualizing Data using t-SNE"; Laurens van der Maaten, et al.; Journal of Machine Learning Research; vol. 9, pp. 2579-2605; Nov. 2008.
"Quantitative High-Throughput Screening: A Titration-Based Approach that Efficiently Identifies Biological Activities in Large Chemical Libraries"; James Inglese, et al.; vol. 103, No. 31, pp. 11473-11478; Aug. 1, 2006.
"Screening Cellular Feature Measurements for Image-Based Assay Development"; David J. Logan, et al.; Journal of Biomolecular Screening; vol. 15, No. 7; Jun. 1, 2010.
"Classifying and Segmenting Microscopy Images with Deep Multiple Instance Learning"; Oren Z. Kraus, et al.; Bioinformatics; vol. 32, No. 12, pp. i52-i59; Published Online Jun. 11, 2016.
"Increasing the Content of High-Content Screening: An Overview"; Shantanu Singh, et al.; Journal of Biomolecular Screening; vol. 19, No. 5, pp. 640-650; Apr. 7, 2014.
"Triplet Networks for Robust Representation Learning"; Mason Victors, Recursion Pharmaceuticals; DeepBio Video Conference hosted by the Carpenter Lab at the Broad Institute; Presented Sep. 28, 2016.
"Applications in Image-Based Profiling of Perturbations"; Juan C Caicedo, et al.; Current Opinion in Biotechnology, 39, pp. 134-142; Apr. 17, 2016.

(56) References Cited

OTHER PUBLICATIONS

"Data Analysis Using Regression and Multilevel/Hierarchical Models"; Andrew Gelman, et al.; Cambridge University Press New York, NY, USA, vol. 1; Jun. 13, 2012.
"Deep Learning"; Yann LeCun, et al.; Nature, 521, pp. 436-444; May 28, 2015.
"A Threshold Selection Method from Gray-Level Histograms"; Nobuyuki Otsu; IEEE Transactions on Systems, Man, and Cybernetics, vol. SMC-9, No. 1, pp. 62-66; Jan. 1979.
"Scikit-learn: Machine Learning in Python"; Fabian Pedregosa, et al.; Journal of Machine Learning Research, 12, pp. 2825-2830; Oct. 2011.
"Is Poor Research the Cause of the Declining Productivity of the Pharmaceutical Industry? An Industry in Need of a Paradigm Shift"; Frank Sams-Dodd; Drug Discovery Today, vol. 18, Issues 5-6, pp. 211-217; Mar. 2013.
"Correlation Alignment for Unsupervised Domain Adaptation"; Baochen Sun, et al.; arXiv.1612.01939v1; retrieved from http://arxiv.org/abs/1612.01939; uploaded to arxiv.org on Dec. 6, 2016.
"How Were New Medicines Discovered?"; David C Swinney, et al.; Nature Reviews Drug Discovery, 10, pp. 507-519; Jul. 2011.
"Developing Predictive Assays: The Phenotypic Screening rule of 3"; Fabien Vincent, et al.; Science Translational Medicine, vol. 7, Issue 293, pp. 293ps15; Jun. 24, 2015.
"Improving Phenotypic Measurements in High-Content Imaging Screens"; D. Michael Ando, et al.; bioRxiv preprint; retrieved from https://www.biorxiv.org/content/early/2017/07/10/161422.full.pdf; posted online Jul. 10, 2017.
"A novel scheme for abnormal cell detection in Pap smear images"; Tong Zhao et al.; Proceedings of SPIE, vol. 5318, pp. 151-162; 2004.
"From Cell Image Segmentation to Differential Diagnosis of Thyroid Cancer"; S. Ablameyko et al.; IEEE 1051-4651/02, pp. 763-766; 2002.
"Automated Classification of Pap Smear Tests Using Neural Networks"; Zhong Li et al.; IEEE 0-7803-7044-9/01, pp. 2899-2901; 2001.
"Using CellProfiler for Automatic Identification and Measurement of Biological Objects in Images"; Martha S. Vokes, et al.; Current Protocols in Molecular Biology 14.17.1-14.17.12 (Apr. 2008).
"Strategy for Identifying Repurposed Drugs for the Treatment of Cerebral Cavernous Malformation"; Christopher C. Gibson, et al.; American Heart Association Journal—Circulation (Jan. 20, 2015).
"CellProfiler: Image Analysis Software for Identifying and Quantifying Cell Phenotypes"; Anne E. Carpenter, et al.; Genome Biology 2006, 7:R100 (Oct. 31, 2006).
"Quantifying Co-Cultured Cell Phenotypes in High-Throughput Using Pixel-Based Classification"; David J. Logan, et al.; Methods 96, 6-11 (Dec. 11, 2015).
"Cell Painting, a High-Content Image-Based Assay for Morphological Profiling Using Multiplexed Fluorescent Dyes"; Mark-Anthony Bray, et al.; Nature Protocols, 11(9): 1757-1774 (Aug. 25, 2016).
Olympus Life Science, Introduction to Confocal Microscopy, Dec. 31, 2014, Wayback Machine, file:///C:/Users/bbernardi/Documents/e-Red%20Folder/16133542/Confocal%20Microscopy%20-%20Introduction%20_%20Olympus%20Life%20Science.pdf, p. 1-11, (Year: 2014).
Sanjee Abeytunge, Evaluation of breast tissue with confocal strip—mosaiking microscopy: a test approach emulating pathology-like examination, Mar. 22, 2017, Journal of Biomedical Optics, p. 1-20. (Year: 2017).
Chetak Kandaswamy, High-Content Analysis of Breast Cancer using Single-Cell Deep Transfer Learning, 2016, Journal of Biomolecular Screening, vol. 21(3), p. 252-259. (Year: 2016).
Juan C. Caicedo, Weakly Supervised Learning of Single-Cell Feature Embedding, Jun. 2018, IEEE/CVF Conference on Computer Vision and Pattern Rcognition, p. 9309-9318. (Year: 2018).
Juan C. Caidedo, Applications in image-based profiling of perturbations, Jun. 2016, Current Opinion in Biotechnology, p. 134-142. (Year: 2016).
Heba Sailem, Discovery of Rare Phenotypes in Cellular Images Using Weakly Supervised Deep Learning, 2017, IEEE International Conference on Computer Vision Workshops, p. 49-55. (Year: 2017).

\* cited by examiner

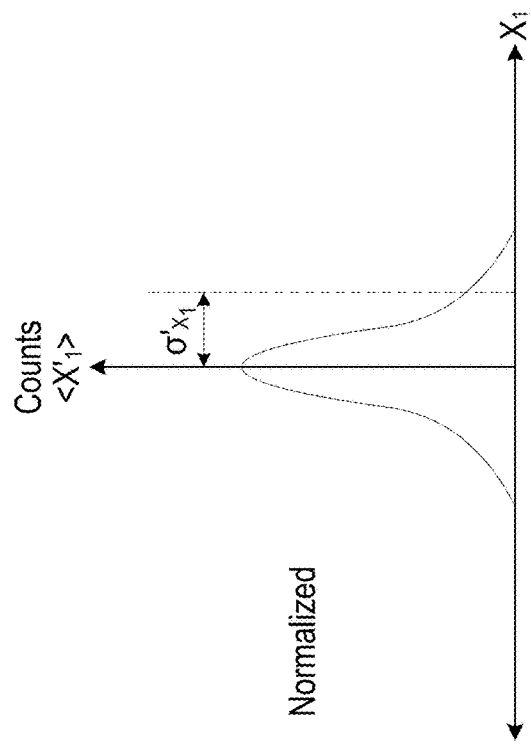
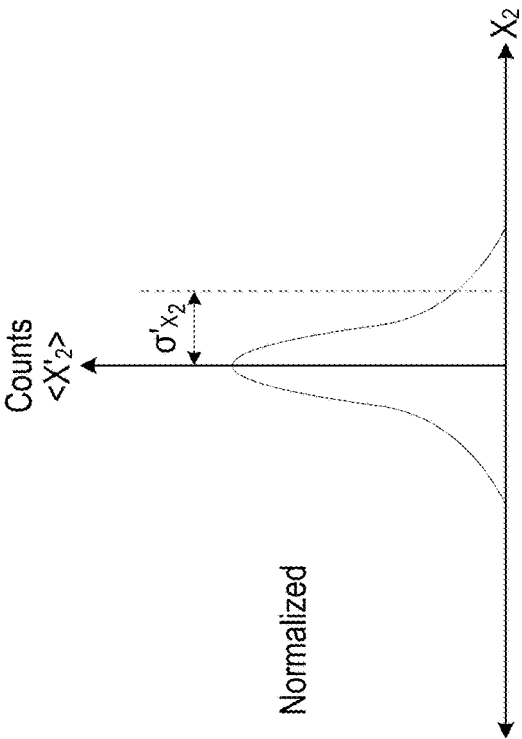
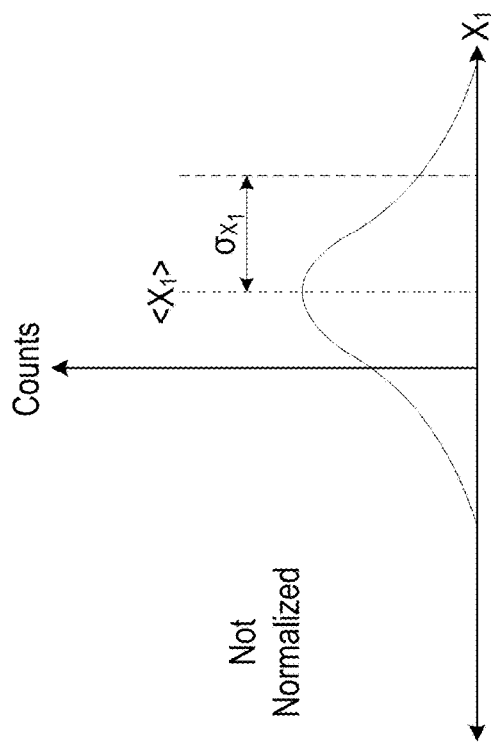
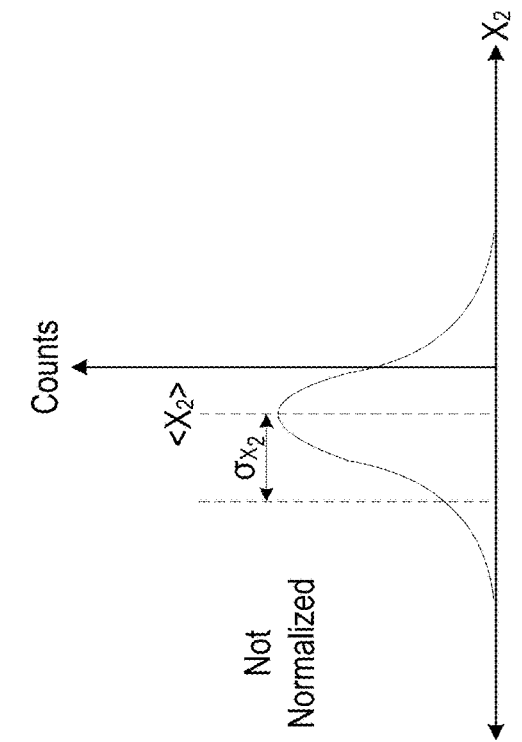
FIG. 2A
FIG. 2B
FIG. 2C
FIG. 2D

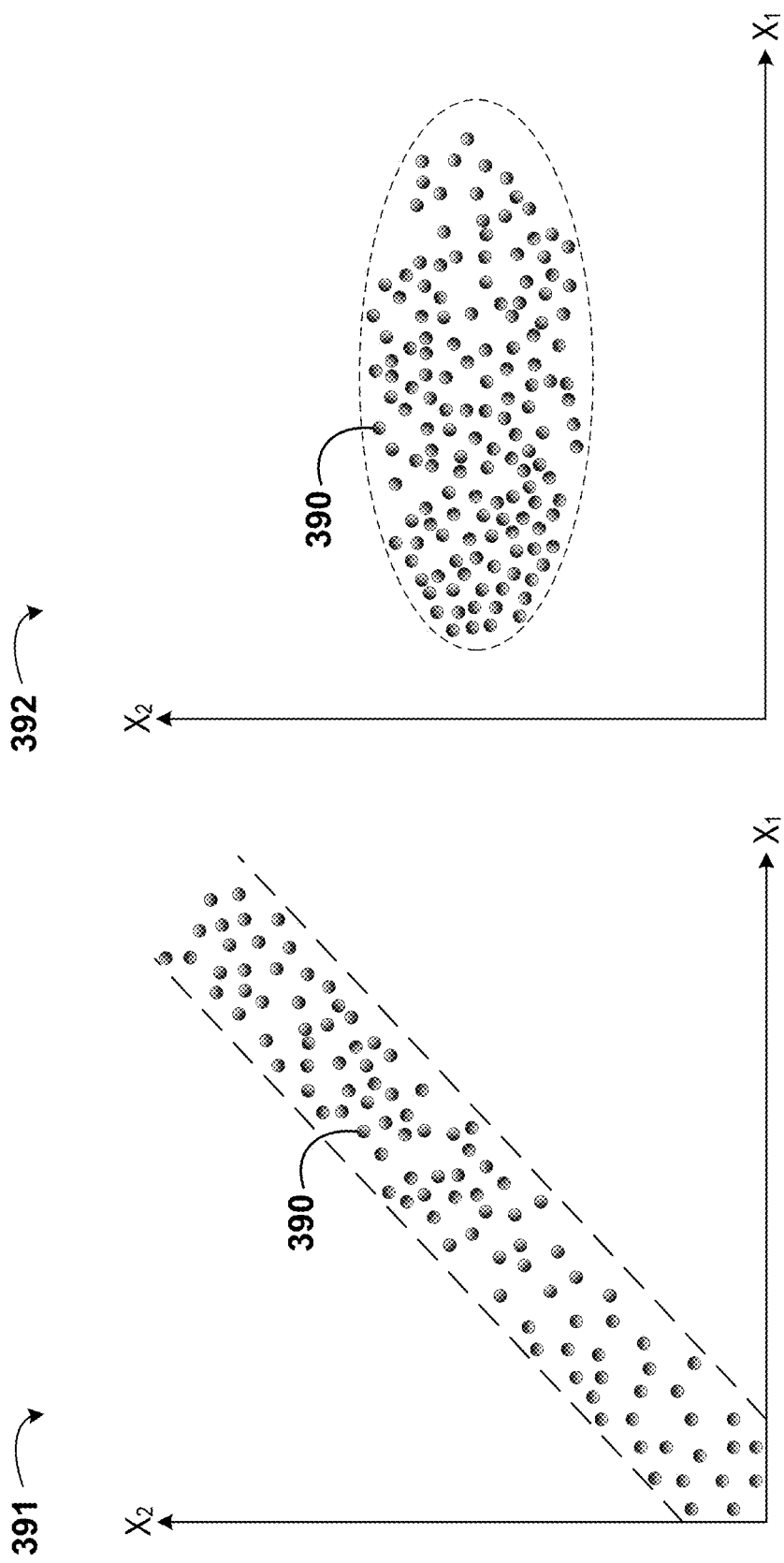

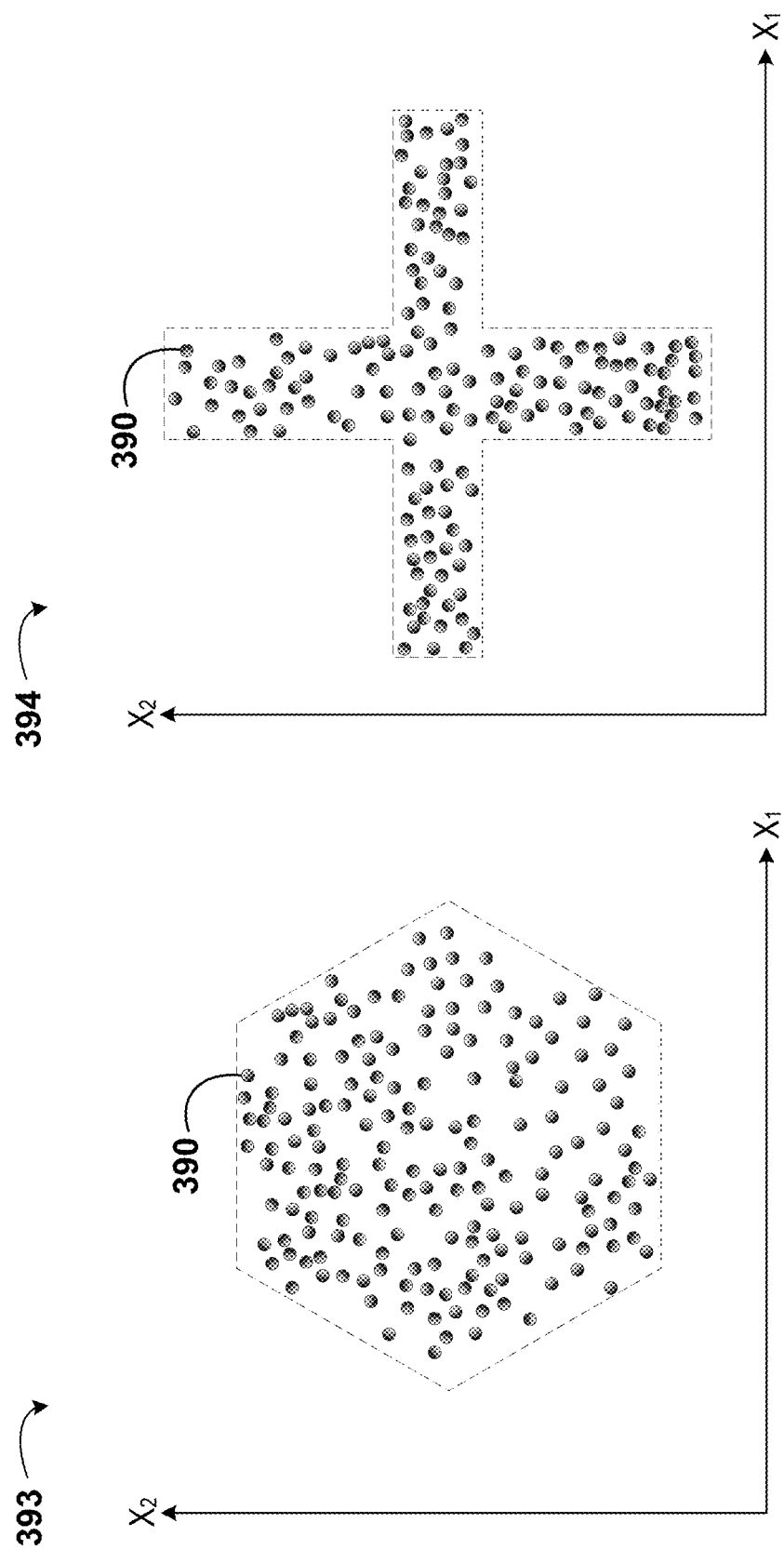

400

|  | $Y_1$ | $Y_2$ |
|---|---|---|
| Target Phenotype | 8.2 | 5.6 |
| Candidate Phenotype$_1$ | 3.6 | 9.5 |
| Candidate Phenotype$_2$ | 1.8 | 10.0 |
| Candidate Phenotype$_3$ | 4.2 | 1.3 |
| Candidate Phenotype$_4$ | 5.0 | 5.9 |
| Candidate Phenotype$_5$ | 9.0 | 4.8 |
| Candidate Phenotype$_6$ | 10.0 | 7.4 |

FIG. 4A

| | $Y_1$ | $Y_2$ | Vector Distance to Target Phenotype |
|---|---|---|---|
| Target Phenotype | 8.2 | 5.6 | 0 |
| Candidate Phenotype$_1$ | 3.6 | 9.5 | 6.03 |
| Candidate Phenotype$_2$ | 1.8 | 10.0 | 7.77 |
| Candidate Phenotype$_3$ | 4.2 | 1.3 | 5.87 |
| Candidate Phenotype$_4$ | 5.0 | 5.9 | 3.21 |
| Candidate Phenotype$_5$ | 9.0 | 4.8 | 1.13 |
| Candidate Phenotype$_6$ | 10.0 | 7.4 | 2.55 |

404 (table), 405 (Vector Distance to Target Phenotype column)

|  | $Y'_1$ | $Y'_2$ |
|---|---|---|
| Target Phenotype | 4.1 | 5.6 |
| Candidate Phenotype$_1$ | 1.8 | 9.5 |
| Candidate Phenotype$_2$ | 0.9 | 10.0 |
| Candidate Phenotype$_3$ | 2.1 | 1.3 |
| Candidate Phenotype$_4$ | 2.5 | 5.9 |
| Candidate Phenotype$_5$ | 4.5 | 4.8 |
| Candidate Phenotype$_6$ | 5.0 | 7.4 |

FIG. 4D

| | $Y'_1$ | $Y'_2$ | Vector Distance to Target Phenotype |
|---|---|---|---|
| Target Phenotype | 4.1 | 5.6 | 0 |
| Candidate Phenotype$_1$ | 1.8 | 9.5 | 4.53 |
| Candidate Phenotype$_2$ | 0.9 | 10.0 | 5.44 |
| Candidate Phenotype$_3$ | 2.1 | 1.3 | 4.74 |
| Candidate Phenotype$_4$ | 2.5 | 5.9 | 1.63 |
| Candidate Phenotype$_5$ | 4.5 | 4.8 | 0.89 |
| Candidate Phenotype$_6$ | 5.0 | 7.4 | 2.01 |

FIG. 4F

PHENOTYPE ANALYSIS OF CELLULAR IMAGE DATA USING A DEEP METRIC NETWORK

CROSS-REFERENCE TO RELATED APPLICATIONS

The present application is a Continuation application claiming priority to U.S. application Ser. No. 16/133,542, filed Sep. 17, 2018; which itself is a Continuation-in-Part application claiming priority to U.S. application Ser. No. 15/808,699, filed Nov. 9, 2017; which itself is a Continuation-in-Part application claiming priority to U.S. application Ser. No. 15/433,027, filed Feb. 15, 2017; the contents of each of which are hereby incorporated by reference in their entirety.

BACKGROUND

Unless otherwise indicated herein, the materials described in this section are not prior art to the claims in this application and are not admitted to be prior art by inclusion in this section.

Understanding mechanisms by which a disease acts can be important when prescribing a treatment regimen for a patient having such a disease. For some diseases, the current state of knowledge may not be at a level that allows for such a treatment regimen to be developed. Thus, methods of improving the level of understanding of disease mechanisms, or of screening for effective treatments even while remaining relatively unknowledgeable about a given disease mechanism, could be useful in treating patients.

Further, machine learning is a field in computing that involves a computing device training a model using "training data." There are two primary classifications of methods of training models: supervised learning and unsupervised learning. In supervised learning, the training data is classified into data types, and the model is trained to look for variations/similarities among known classifications. In unsupervised learning, the model is trained using training data that is unclassified. Thus, in unsupervised learning, the model is trained to identify similarities based on unlabeled training data.

Once the model has been trained on the training data, the model can then be used to analyze new data (sometimes called "test data"). Based on the model's training, a computing device can use the trained model to evaluate the similarity of the test data.

There are numerous types of machine-learned models, each having its own set of advantages and disadvantages. One popular machine-learned model is an artificial neural network. The artificial neural network involves layers of structure, each trained to identify certain features of an input (e.g., an input image, an input sound file, or an input text file). Each layer may be built upon sub-layers that are trained to identify sub-features of a given feature. For example, an artificial neural network may identify composite objects within an image based on sub-features such as edges or textures.

Given the current state of computing power, in some artificial neural networks many such sub-layers can be established during training of a model. Artificial neural networks that include multiple sub-layers are sometimes referred to as "deep neural networks." In some deep neural networks, there may be hidden layers and/or hidden sub-layers that identify composites or superpositions of inputs. Such composites or superpositions may not be human-interpretable.

SUMMARY

The specification and drawings disclose embodiments that relate to phenotype analysis of cellular image data using a deep metric network.

In a first aspect, the disclosure describes a method. The method includes receiving, by a computing device, a target image of a target biological cell having a target phenotype. The method also includes obtaining, by the computing device, a semantic embedding associated with the target image. The semantic embedding associated with the target image is generated using a machine-learned, deep metric network model. Further, the method includes obtaining, by the computing device for each of a plurality of candidate images of candidate biological cells each having a respective candidate phenotype, a semantic embedding associated with the respective candidate image. The semantic embedding associated with the respective candidate image is generated using the machine-learned, deep metric network model. In addition, the method includes identifying, by the computing device for each of the semantic embeddings, common morphological variations. Still further, the method includes reducing, by the computing for each of the semantic embeddings based on the identified common morphological variations, effects of nuisances. Additionally, the method includes determining, by the computing device, a similarity score for each candidate image. The similarity score for each candidate image represents a degree of similarity between the target phenotype and the respective candidate phenotype.

In a second aspect, the disclosure describes a non-transitory, computer-readable medium having instructions stored thereon. The instructions, when executed by a processor, cause the processor to execute a method. The method includes receiving, by the processor, a target image of a target biological cell having a target phenotype. The method also includes obtaining, by the processor, a semantic embedding associated with the target image. The semantic embedding associated with the target image is generated using a machine-learned, deep metric network model. Further, the method includes obtaining, by the processor for each of a plurality of candidate images of candidate biological cells each having a respective candidate phenotype, a semantic embedding associated with the respective candidate image. The semantic embedding associated with the respective candidate image is generated using the machine-learned, deep metric network model. In addition, the method includes identifying, by the processor for each of the semantic embeddings, common morphological variations. Still further, the method includes reducing, by the processor for each of the semantic embeddings based on the identified common morphological variations, effects of nuisance. Additionally, the method includes determining, by the processor, a similarity score for each candidate image. The similarity score for each candidate image represents a degree of similarity between the target phenotype and the respective candidate phenotype.

In a third aspect, the disclosure describes a method. The method includes preparing a multi-well sample plate with a target biological cell having a target phenotype and candidate biological cells. The method also includes applying a variety of candidate treatment regimens to each of the candidate biological cells. Further, the method includes recording a target image of the target biological cell. Additionally, the method includes recording candidate images of each of the candidate biological cells, each having a respective candidate phenotype arising in response to the candidate treatment regimen being applied. Still further, the method includes receiving, by a computing device, the target image and the candidate images. In addition, the method includes obtaining, by the computing device, a semantic embedding associated with the target image. The semantic embedding associated with the target image is generated using a machine-learned, deep metric network model. Even further, the method includes obtaining, by the computing device for each candidate image, a semantic embedding associated with the respective candidate image. The semantic embedding associated with the respective candidate image is generated using the machine-learned, deep metric network model. Yet further, the method includes identifying, by the computing device for each of the semantic embeddings, common morphological variations. Still yet further, the method includes reducing, by the computing device for each of the semantic embeddings based on the identified common morphological variations, effects of nuisances. Even yet further, the method includes determining, by the computing device, a similarity score for each candidate image. The similarity score for each candidate image represents a degree of similarity between the target phenotype and the respective candidate phenotype. Still yet even further, the method includes selecting, by the computing device, a preferred treatment regimen among the variety of candidate treatment regimens based on the similarity scores.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 2A is a graphical illustration of an un-normalized set of phenotypic data, according to example embodiments.

FIG. 2B is a graphical illustration of a normalized set of phenotypic data, according to example embodiments.

FIG. 2C is a graphical illustration of an un-normalized set of phenotypic data, according to example embodiments.

FIG. 2D is a graphical illustration of a normalized set of phenotypic data, according to example embodiments.

FIG. 3I is a graphical illustration of a topology enforced during training of a machine-learned, deep metric network model, according to example embodiments.

FIG. 3J is a graphical illustration of a topology enforced during training of a machine-learned, deep metric network model, according to example embodiments.

FIG. 3K is a graphical illustration of a topology enforced during training of a machine-learned, deep metric network model, according to example embodiments.

FIG. 3L is a graphical illustration of a topology enforced during training of a machine-learned, deep metric network model, according to example embodiments.

FIG. 4A is a tabular illustration of an un-normalized data set having a target phenotype and six candidate phenotypes, according to example embodiments.

FIG. 4C is a tabular illustration of vector distances between candidate phenotypes and a target phenotype, according to example embodiments.

FIG. 4D is a tabular illustration of a normalized data set having a target phenotype and six candidate phenotypes, according to example embodiments.

FIG. 4F is a tabular illustration of vector distances between candidate phenotypes and a target phenotype, according to example embodiments.

DETAILED DESCRIPTION

Figure 1:
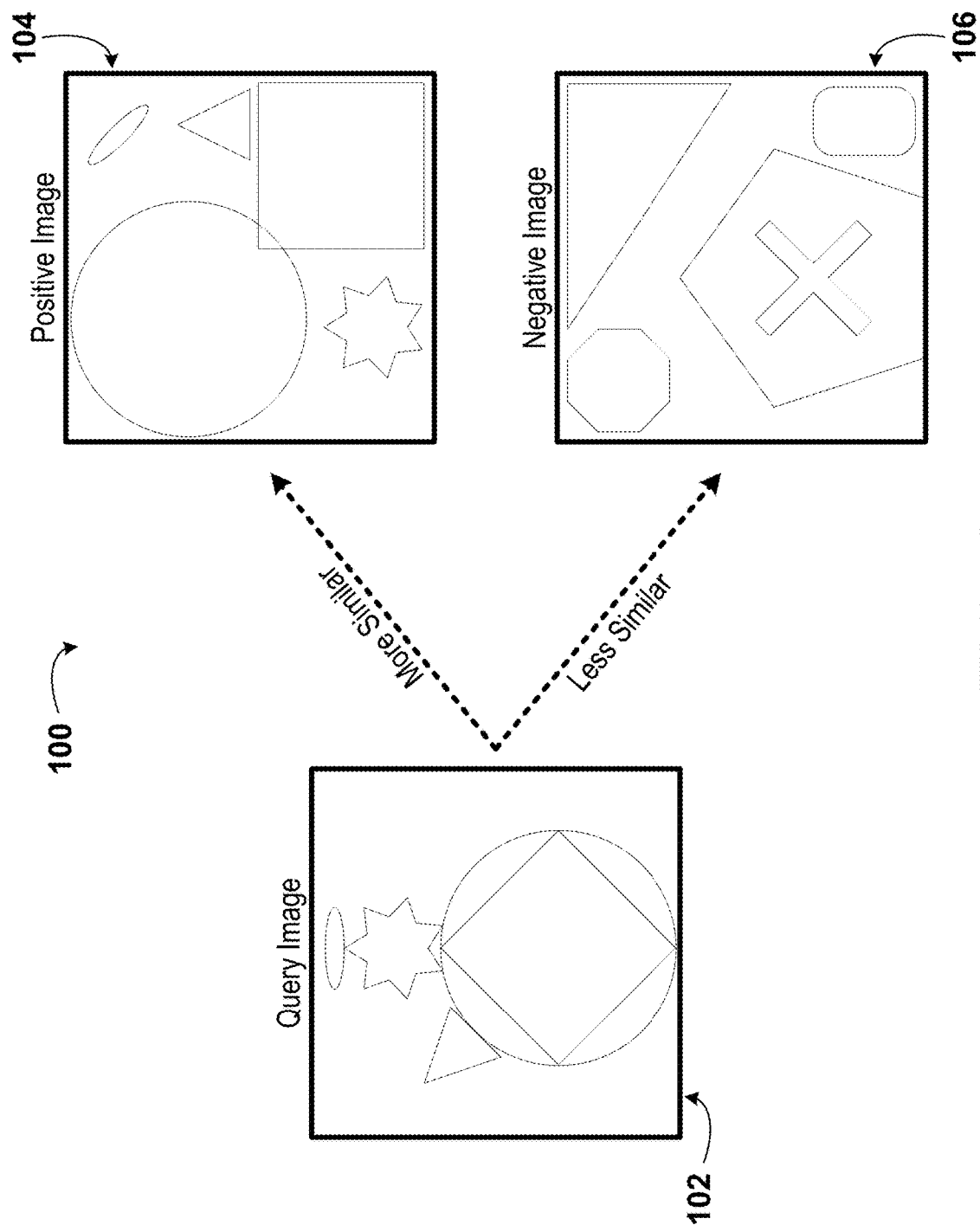
FIG. 1 is an illustration of a three-image set, according to example embodiments.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. In addition, some of the illustrated elements may be combined or omitted. Similarly, an example embodiment may include elements that are not illustrated in the figures.

I. OVERVIEW

Example embodiments may relate to analysis of perturbed subjects using semantic embeddings (e.g., semantic embeddings generated using a machine-learned, deep metric network model) generated based on visual representations of the perturbed subjects. The semantic embeddings may further be used to determine one or more qualities of the perturbed subjects and/or similarities/differences among the perturbed subjects.

In various embodiments, the subjects may be perturbed using one or more of a variety of techniques. The way in which the subjects are perturbed may be the same across all subjects or may vary across multiple subjects. Further, the perturbation applied to the subjects may also depend on the types of subjects being perturbed. For example, biological material (e.g., cells) may be perturbed chemically while semiconductor materials may be perturbed optically or thermally. Other types of perturbation are also possible and are contemplated herein.

Upon applying perturbations to the subjects, visual representations of the subjects may be produced. Visual representations may include captured images, recorded videos, or visual representations of otherwise non-visual data (e.g., a three-dimensional intensity plot where the x-position and y-position correspond to the $i^{th}$ and $j^{th}$ elements of a covariance matrix, respectively, and the intensity at a given x-y position corresponds to the value at the (i, j) position of the covariance matrix).

The visual representations may be produced using at least one imaging modality. For example, the visual representation may be captured by a sensor, such as a camera or a magnetic resonance imaging (MRI) sensor. Alternatively, the visual representation may be produced by a computing device based on a set of received data. In still other embodiments, a visual representation may not be produced, but data capable of visual representation may be used directly, without first producing a visual representation. For example, a covariance matrix may be analyzed without generating a three-dimensional intensity plot. Other types of data that are amenable to visual representation (e.g., data where a spatial location has some correlation to information about the underlying subject) besides covariance matrices may also be used.

Using the visual representations, semantic embeddings can be obtained for each of the respective visual representations. Such semantic embeddings may be obtained using a machine-learned, deep metric network model, in some embodiments. Then, using the semantic embeddings, each of the visual representations can be classified (e.g., into one or more groups). Based on the classification(s) of each of the visual representations, one or more features of the respective perturbed subjects may be determined. For example, the type of perturbation(s) applied, the degree of perturbation(s) applied, the effect of the perturbation(s) applied, and/or the type of subject may be determined based on the classifications identified for the visual representations.

In some embodiments, the subjects may be biological cells (other subjects are also possible). Visual representations of the biological cells may be produced and semantic embeddings can be obtained in order to compare the biological cells (e.g., to establish similarities between the biological cells). Establishing similarity between multiple phenotypes may allow for the study of biological pathways. For example, multiple candidate biological cells may be treated with various compounds. The time-evolution of the phenotypes of those candidate biological cells can then be compared to one another. This may allow for a study of mechanisms of action within the candidate biological cells.

In alternate embodiments, target cells having target phenotypes may be compared with candidate cells having candidate phenotypes to establish whether the candidate cells can be classified as healthy or unhealthy cells. For example, if the target cell is known to have a healthy (or unhealthy) phenotype, and it is determined that the candidate cells have a sufficiently similar phenotype to the target phenotype, the candidate cells may be deemed to have a healthy (or unhealthy) phenotype. Further, techniques as described herein may be used to compare cells acquired from various anatomical regions of a patient's body with one another (e.g., to determine if a disease has progressed from one anatomical region of a patient's body to another).

Even further, if candidate cells are known to initially have an unhealthy phenotype, the candidate cells may then be treated with various candidate treatment regimens (e.g., various candidate treatment compounds, various candidate concentrations of a candidate treatment compound, or various candidate treatment durations). After treatment, the similarity between the candidate cells and a target cell having a healthy phenotype may then be determined. The candidate treatment regimens may then be ranked in successfulness based on the corresponding candidate cells phenotypic similarity to the target cell. Such a technique can be used to develop treatment regimens for patients, for example.

Embodiments may use a machine-learned, deep metric network model (e.g., executed by a computing device) to facilitate image comparisons of biological cells having various cellular phenotypes. The machine-learned, deep metric network model may be trained, for example, using consumer photographic training data. The consumer photographic training data may include a number of three-image sets (e.g., 33 million three-image sets, 100 million three-image sets, 1 billion three-image sets, 10 billion three-image sets, or 33 billion three-image sets). The three-image sets may be generated based on query results (e.g., user internet search results). Additionally, the three-image sets may include images that depict a wide variety of scenes, not solely biological cells or even scientific data. For example, one three-image set may include three images of automobiles, a second three-image set may include three images of animals, and a third three-image set may include three images of cities.

Further, each three-image set may include a query image, a positive image, and a negative image. The query image may be an image that was searched by a user, for example, and the positive image may have been identified by the user as being more similar to the query image than the negative image was to the query image. Based on these three-image sets, a computing device may refine the machine-learned, deep metric network model. Refining the model may include developing one or more semantic embeddings that describe similarities between images. For example, a semantic embedding may have multiple dimensions (e.g., 64 dimensions) that correspond to various qualities of an image (e.g., shapes, textures, image content, relative sizes of objects, and perspective). The dimensions of the semantic embeddings could be either human-interpretable or non-human interpretable. In some embodiments, for example, one or more of the dimensions may be superpositions of human-interpretable features.

While the machine-learned, deep metric network may have been trained using consumer photographic data, the model can be applied to data which is not consumer photographic (e.g., images of cells or other scientific images). The use of a machine-learned, deep metric network model on types of data other than those on which it was trained is sometimes referred to as "transfer learning." In order to use the machine-learned, deep metric network model to compare scientific images, the scientific images may be converted or transformed to a format that is commensurate with the model. Converting the scientific images (e.g., target images of target biological cells or candidate images of candidate biological cells) may include scaling or cropping the respective scientific image (e.g., such that the respective scientific image has a size and/or an aspect ratio that can be compared using the model) or converting channels of the scientific images to grayscale. Additional pre-processing may occur prior to using the machine-learned, deep metric network model for phenotype comparison (e.g., the scientific image may be cropped around a nucleus, such that only one cell is within the scientific image).

Two scientific images may then be compared (e.g., by a computing device) by comparing semantic embeddings generated for the images using the machine-learned, deep metric network model. For example, one scientific image may be a candidate image of a candidate biological cell having a candidate phenotype and a second scientific image may be a target image of a target biological cell having a target phenotype. The two images may be compared, using their semantic embeddings, to determine a similarity score between the two images. The similarity score may represent how similar the cellular phenotypes depicted in the two images are.

To compare the two images, a semantic embedding may be obtained for each image using the machine-learned, deep metric network model (e.g., by a computing device). The semantic embeddings may have dimensions that correspond to dimensions associated with the machine-learned, deep metric network model developed during training. Obtaining a semantic embedding for each image may include, in some embodiments, obtaining a semantic embedding for each channel within the image and then concatenating the single-channel semantic embeddings into a unified semantic embedding for the entire image.

In embodiments where multiple images are recorded and analyzed using the machine-learned, deep metric network model, normalization (e.g., typical variation normalization) can be performed. Normalization may include scaling and/or shifting the values of one or more of the dimensions of the semantic embeddings in some or all of the images (e.g., the values may be scaled and/or shifted in a given dimension based on negative control groups). Further, the values may be scaled and/or shifted such that the distribution of values across all images for certain dimensions may have specified characteristics. For example, the values may be scaled and/or shifted such that the distribution for a given dimension has zero-mean and unit variance. In some embodiments, the normalization may be performed after using principal component analysis (PCA). Additionally, in some embodiments, all dimensions may be scaled and/or shifted to have zero-mean and unit variance (i.e., the dimensions may be "whitened").

After obtaining semantic embeddings for the images using the machine-learned, deep metric network model, similarity scores can be calculated. The similarity score for a candidate image/phenotype may correspond to the vector distance in n-dimensional space (e.g., where n is the number of dimensions defined within the semantic embeddings of the machine-learned, deep metric network model) between the candidate image/phenotype and the target image/phenotype. In alternate embodiments, the similarity score may correspond to an inverse of the vector distance in n-dimensional space. In still other embodiments, similarity scores may also be calculated between two candidate images or even between two channels within the same image.

After calculating one or more similarity scores, the similarity scores may be analyzed. For example, each of the similarity scores may be compared against a threshold similarity score, with similarity scores greater than (or less than) or equal to the threshold similarity score corresponding to candidate images of candidate cells having candidate phenotypes that are deemed to be the same as the target phenotype of the target biological cell in the target image. In other embodiments, the candidate images may be ranked by similarity score. In such embodiments, the highest similarity score may correspond to a candidate biological cell with a candidate phenotype that is most similar to the target phenotype. If the candidate biological cells were treated with various candidate treatment regimens, and the target phenotype represents a healthy phenotype, then the candidate treatment regimen used to produce the candidate phenotype corresponding to the highest similarity score may be identified as a potentially effective treatment regimen that could be applied to a patient.

Additionally, using semantic embeddings determined for target images of target biological cells and candidate images of candidate biological cells, biological cells may be grouped into a plurality of phenotypic strata. For example, candidate biological images that have values for one or more dimensions (e.g., within a respective semantic embedding) that are of a threshold similarity (e.g., based on the vector distance between the corresponding candidate phenotypes of the candidate biological images) with one another may be grouped into the same phenotypic stratum. Such a phenotypic stratum may be determined according to a predetermined threshold distance. Alternatively, such a phenotypic stratum may be based on a density of candidate phenotypes within a certain region of a corresponding multi-dimensional space (e.g., such a density indicating a similarity among phenotypes of the candidate biological cells in the corresponding candidate images).

Further, in some embodiments, some of the candidate biological cells in the candidate images may have had candidate treatment compounds applied or induced genetic mutations. By comparing the semantic embeddings of such candidate biological cells, one or more candidate treatment compounds can be identified as mimicking one or more genetic modifications (e.g., mutations). For example, if the same phenotypic stratum results after applying a candidate treatment compound as results after applying a given genetic mutation, the candidate treatment compound may effectively "mimic" the genetic modification. Similarly, if applying a candidate treatment compound results in a candidate biological cell moving from one phenotypic stratum (e.g., representing a first stage of a disease) to another phenotypic stratum (e.g., representing a second stage of a disease), and applying a genetic mutation results in the same movement between phenotypic strata, the candidate treatment compound may "mimic" the genetic modification.

II. EXAMPLE PROCESSES

The following description and accompanying drawings will elucidate features of various example embodiments. The embodiments provided are by way of example, and are not intended to be limiting. As such, the dimensions of the drawings are not necessarily to scale. Further, various subjects are described throughout as being perturbed and/or imaged. For example, one or more biological cells may be described as example subjects. It is understood that, throughout, whenever an operation is described as being performed on an example subject, (such as a biological cell) or an image or other visual representation of such an example subject, such an operation could be equally performed on other types of subjects (e.g., fibroblasts, malaria cells, yeast cells, yeast cultures, bacteria, bacterial cultures, fungus, fungal cultures, cancer cells, blood cells, malarial parasites, mitochondria, nuclei, axons, dendrites, induced pluripotent stem cells, biological cells from a given region of an organism, biological cells from a given tissue of an organism, biological cells from a given organ of an organism, biological cells from a given system of an organism, biological cell ensembles, tissues, organs, organoids, biological systems, organisms, groups of organisms, ecosystems, chemical compounds, crystals, metallic glasses, mixtures of metallic salts, semiconductors, metals, dielectrics, graphene, microelectromechanical systems (MEMS), or nanoelectromechanical systems (NEMS)).

FIG. 1 is an illustration of a three-image set 100, according to example embodiments. The three-image set 100 includes a query image 102, a positive image 104, and a negative image 106. The three-image set 100 may be an example of a three-image set used as training date for a machine-learned, deep metric network model (e.g., used during unsupervised training of the machine-learned, deep metric network). Each image in the three-image set 100 may be a three channel (e.g., with a red channel, a green channel, and a blue channel) consumer photograph. Further, each channel may have an 8-bit depth (e.g., may have a decimal value between 0 and 255, inclusive, for each pixel in each channel that indicates the intensity of the pixel). Other numbers of channels and bit depths are also possible, in various embodiments. In some embodiments, each image in a three-image set, or even each image across all three-image sets, may have a standardized size (e.g., 200 pixels by 200 pixels).

Further, the query image 102, the positive image 104, and the negative image 106 may be internet search results. In some embodiments, based on user feedback, the positive image 104 may be more similar to the query image 102 than the positive image 104 is to the negative image 106. In some embodiments, the three-image sets used as training data for the machine-learned, deep metric network may not depict biological cells/phenotypes. For example, the query image could be a car, the positive image could be a truck, and the negative image could be an airplane.

Various features of the query image 102, the positive image 104, and the negative image 106 may influence the user feedback. Some example features include shapes, textures, image content, relative sizes of objects, and perspective depicted in the query image 102, the positive image 104, and the negative image 106. Other features are also possible. In the example illustrated in FIG. 1, the positive image 104 includes the same set of shapes as the query image 102, but in a different arrangement. Conversely, the negative image 106 includes a different set of shapes from the query image 102.

In some embodiments, a computing device may use multiple three-image sets (e.g., about 100 million total images or about 100 million three-image sets) to define semantic embeddings within the machine-learned, deep metric network model. For example, the computing device may establish 64 dimensions within semantic embeddings of the machine-learned, deep metric network model for each channel of the images in the three-image sets. In other embodiments, other numbers of dimensions are also possible. The dimensions may contain information corresponding to the various features of the three-image sets used to train the machine-learned, deep metric network model. Further, for images assigned semantic embeddings according to the machine-learned, deep metric network model, the semantic embeddings can be used to analyze the degree of similarity between two images (e.g., based on a vector distance in a multi-dimensional space defined by the semantic embeddings between the two images, i.e., a similarity score).

Additionally, the features within the three-image sets used by a computing device to update the machine-learned, deep metric model may be selected based on the positive image 104, the query image 102, and the negative image 106 (as opposed to pre-identified by a programmer, for instance). In other words, the process used by a computing device to train the machine-learned, deep metric network model may include unsupervised learning. The features used to define various dimensions of the semantic embeddings may be human-interpretable (e.g., colors, sizes, textures, or shapes) or non-human-interpretable (e.g., superpositions of human-interpretable features), in various embodiments.

FIG. 2A is a graphical illustration of an un-normalized set of phenotypic data, according to example embodiments. For example, the phenotypic data may correspond to biological cells in candidate images, target images, and/or control group images being analyzed using a machine-learned, deep metric network model. The phenotypic data may represent the number ("counts") of biological cells from the group of biological cells (e.g., candidate biological cells) that have a given value for a given dimension ($X_1$) of a semantic embedding. As illustrated, the number of biological cells having a given value for the given dimension ($X_1$) of the semantic embedding may be pseudo-continuous (or approximated as a continuous function). In other words, any value of the dimension ($X_1$) within a given range is occupied by at least one of the biological cells in the group. However, in alternate embodiments, only discrete values of the dimension ($X_1$) may be possible, in which case the illustration of the distribution of the data may more closely resemble a bar graph.

The distribution illustrated in FIG. 2A may have a mean value ($<X_1>$) and a standard deviation ($\sigma_{X_1}$). As illustrated, the mean value ($<X_1>$) is positive. The distribution illustrated in FIG. 2A may represent a distribution that is not normalized. For example, the distribution illustrated in FIG. 2A may be a distribution as it is recorded from images of candidate biological cells after obtaining a semantic embedding, but prior to any other processing (e.g., normalization).

FIG. 2B is a graphical illustration of a normalized set of phenotypic data, according to example embodiments. The data set illustrated in FIG. 2B may be a modified equivalent of the data set illustrated in FIG. 2A (e.g., after normalization). Such a modification may be a result of scaling (e.g., by multiplication) and/or shifting (e.g., by addition) of the values of semantic embeddings of each image in the data set by a given amount (e.g., a scaling factor). In some embodiments, the phenotypic data may be normalized (e.g., scaled or shifted) based on phenotypic data from a negative control group (e.g., an unperturbed control group) or a positive control group (e.g., a control group treated with a candidate compound that yields a known response or a control group having phenotypes of a known disease state). For example, it may be known that a control group's phenotypic data has an expected mean and an expected standard deviation. If, after obtaining the semantic embeddings, the control group's phenotypic data does not have the expected mean and/or the expected standard deviation, the control groups phenotypic data may be normalized (e.g., scaled and/or shifted by one or more factors). Thereafter, phenotypic data for sets of cells other than the control group (e.g., from a candidate group of cells) may be normalized in a way corresponding to the normalization of the control group (e.g., scaled and/or shifted by the same one or more factors).

As illustrated, the data set in FIG. 2B may be normalized such that the mean value ($<X'_1>$) of the dimension ($X_1$) of the semantic embedding is zero (i.e., the distribution of data is zero-centered). Other mean values are also possible in alternate embodiments (e.g., a positive mean value, a negative mean value, a unity mean value, etc.). Further, the data set illustrated in FIG. 2B may be normalized such that the standard deviation ($\sigma'_{X_1}$) of the dimension ($X_1$) of the semantic embedding is 1.0. This may correspond to the data set also having a unit variance (i.e., $\sigma'^2_{X_1}=1.0$) for the dimension ($X_1$) of the semantic embedding.

A similar normalization to that illustrated in FIG. 2B may be applied to multiple dimensions of the semantic embedding. By normalizing values in each dimension to a standardized mean and variance, each dimension may have equal weighting (i.e., equal influence) on a distance between two phenotypes as each other dimension. Said another way, each dimension may equally impact a resulting similarity score. Further, the normalization illustrated in FIG. 2B may prevent aberrant or extraneous phenotypic results from overly influencing the impact score (e.g., a large variation with respect to a target phenotype in a single dimension of a candidate phenotype may not outweigh a series of relatively small variations with respect to the target phenotype in alternate dimensions of the candidate phenotype).

When comparing the normalized set of phenotypic data illustrated in FIG. 2B to the non-normalized set of phenotypic data illustrated in FIG. 2A, it is apparent that the normalized mean ($<X'_1>$) has a value of zero (as opposed to a positive value), and the standard deviation ($\sigma'_{X_1}$) was reduced (e.g., from 1.5 to 1.0). An analogous normalization is illustrated graphically in FIGS. 2C and 2D for a second dimension ($X_2$) of the semantic embedding. In FIG. 2C, an un-normalized set of the phenotypic data has a negative mean value ($<X_2>$) and a greater than unit standard deviation ($\sigma_{X_2}$) for the second dimension ($X_2$). Once normalized, as illustrated in FIG. 2D, the set of phenotypic data may have a mean of zero ($<X'_2>$) and a unit variance ($\sigma'^2_{X_2}$) of 1.0. In some embodiments, normalizing the phenotypic data illustrated in FIG. 2D may involve scaling the data by a value (i.e., a scaling factor) less than 1.0 and shifting the data by a positive value (i.e., a positive shifting value).

In some embodiments, a normalization process may include only adding a shift to the phenotypic data (e.g., to adjust the mean of the data). Alternatively, the normalization process may include only scaling the phenotypic data (e.g., to adjust the standard deviation of the data). In various embodiments, various dimensions of the phenotypic data for a given semantic embedding may be shifted and/or scaled differently from one another. Further, in some embodiments, one or more of the dimensions of the phenotypic data for a given semantic embedding may not be normalized at all. The data may not be normalized if the phenotypic data for one of the dimensions inherently has the desired statistical distribution to match with the other dimensions. Alternatively, the data may not be normalized so that the values of the phenotypic data for a given dimension either intentionally over-influence or intentionally under-influence similarity scores with respect to the rest of the dimensions of the semantic embedding.

As illustrated in FIGS. 2A-2D, both the un-normalized and the normalized distributions of the phenotypic data for a given dimension (e.g., $X_1$ or $X_2$) may be approximately Gaussian. In some embodiments, however, the un-normalized and the normalized distributions may be pseudo-Gaussian or non-Gaussian. In some embodiments, the phenotypic data for some dimensions may be Gaussian while the phenotypic data for other dimensions may be non-Gaussian. Further, in some embodiments, the un-normalized distributions for a given dimension may be non-Gaussian and may be normalized in such a way that the normalized distributions for the given dimension may be approximately or actually Gaussian. Various embodiments may have various graphical shapes for the phenotypic data in various dimensions.

In addition to the normalization illustrated in FIGS. 2A-2D, a transformation of the phenotypic data may be performed to ensure that the dimensions generated for a given semantic embedding are orthogonal to one another (i.e., to prevent certain dimensions from being linear combinations of other dimensions). This may prevent redundant data from influencing similarity scores, for example. In alternate embodiments, orthogonal transformations of the dimensions may occur during the training of the machine-learned, deep metric network (i.e., rather than during phenotypic data analysis).

The orthogonal transformations may include performing PCA, for example. PCA may include calculating eigenvectors and/or eigenvalues of a covariance matrix defined by the phenotypic data in each dimension. In some embodiments, the orthogonal transformation may also include a dimensionality reduction. Having fewer dimensions within a semantic embedding may conserve memory within a storage device of a computing device (e.g., within a volatile memory or a non-volatile memory) by preventing as much data from being stored to describe a phenotypic data set. Again, the above steps may be performed during the training of the machine-learned, deep metric network. Additionally or alternatively, normalizing the data may include performing a whitening transform on the phenotypic data (e.g., to transform the phenotypic data such that it has an identity covariance matrix).

Figures 3A, 3B:
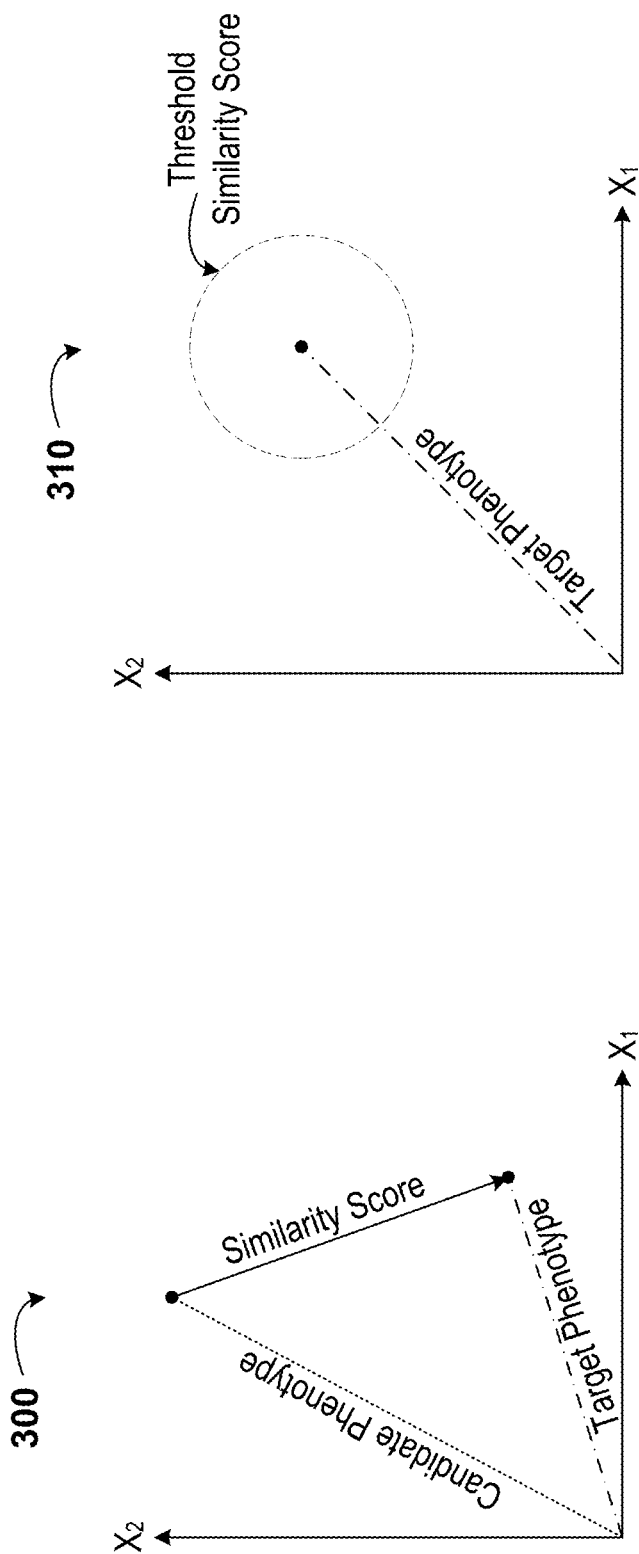
FIG. 3A is a graphical illustration of a data set having a candidate phenotype and a target phenotype, according to example embodiments.
FIG. 3B is a graphical illustration of a target phenotype and a threshold similarity score, according to example embodiments.

FIG. 3A is a graphical illustration of a data set 300 having a candidate phenotype and a target phenotype, according to example embodiments. The candidate phenotype may correspond to a candidate image of a candidate biological cell. Similarly, the target phenotype may correspond to a target image of a target biological cell. For both the candidate phenotype and the target phenotype, the values of each of the dimensions may be found by analyzing the candidate image and the target image, respectively, using the machine-learned, deep metric network model. Further, the values of each of the dimensions illustrated in FIG. 3A may be normalized or un-normalized. The candidate phenotype and the target phenotype are depicted as vectors, each having a respective first dimension ($X_1$) value and a respective second dimension ($X_2$) value.

As illustrated in FIG. 3A, the semantic embedding used to define the candidate phenotype and the target phenotype has two dimensions (namely, $X_1$ and $X_2$). FIG. 3A is provided to illustrate an example embodiment. In various other embodiments, other numbers of dimensions may also be possible. For example, in some embodiments, the semantic embeddings may include 16, 32, 64, 128, 192, or 256, or 320 dimensions.

Also illustrated in FIG. 3A is a vector representing the similarity score between the target phenotype vector and the candidate phenotype vector. The similarity score vector may be equal to the target phenotype vector minus the candidate phenotype vector. The magnitude (i.e., length) of the similarity score vector may correspond to a value of the similarity score. Said another way, the distance between the target phenotype vector and the candidate phenotype vector may be equal to the similarity score. The vector distance may be calculated using the following formula (where $X_1$ represents each dimension defined within the semantic embedding):

$$\text{Distance} = \sqrt{\sum_i \left(X_{i_{target}} - X_{i_{candidate}}\right)^2}$$

In such embodiments, the lower the value of the similarity score, the more similar two phenotypes may be.

In other embodiments, the value of the similarity score may correspond to the inverse of the magnitude of the similarity score vector. Said another way, the inverse of the distance between the target phenotype vector and the candidate phenotype vector is equal to the similarity score. In these alternate embodiments, the greater the value of the similarity score, the more similar two phenotypes may be. Methods of calculating similarity score other than distance and inverse distance are also possible (e.g., a cosine similarity may be calculated to determine similarity score).

FIG. 3B is a graphical illustration 310 of a target phenotype and a threshold similarity score, according to example embodiments. The target phenotype may correspond to a target image of a target biological cell. For the target phenotype, the values of each of the dimensions may be found by analyzing the target image using the machine-learned, deep metric network. Further, the values of each of the dimensions illustrated in FIG. 3B may be normalized or un-normalized. The target phenotype is depicted as a vector, having a respective first dimension ($X_1$) value and a respective second dimension ($X_2$) value.

Illustrated as a circle in FIG. 3B is a threshold similarity score. The threshold similarity score may define a maximum distance at which other phenotypes are considered to be substantially the same as the target phenotype. In some embodiments (e.g., embodiments where similarity score is defined as the inverse of the distance between the target phenotype and another phenotype), the threshold similarity score may define a minimum similarity score value at which other phenotypes are considered to be substantially the same as the target phenotype.

For example, if the target phenotype is an unhealthy phenotype, any candidate phenotype with a combination of values for each of the dimensions such that a vector representing the candidate phenotype resides within the circle defined by the threshold similarity score may be considered an unhealthy phenotype. Similarly, if the target phenotype is a healthy phenotype, any candidate phenotype with a combination of values for each of the dimensions such that a vector representing the candidate phenotype resides within the circle defined by the threshold similarity score may be considered a healthy phenotype. In alternate embodiments, where the semantic embeddings define a multi-dimensional space having n-dimensions (rather than two, as illustrated in FIG. 3B), the threshold similarity score may correspond to an n-dimensional surface. For example, in semantic embeddings having three dimensions, the threshold similarity score may correspond to a spherical shell, as opposed to a circle.

Figure 3D:
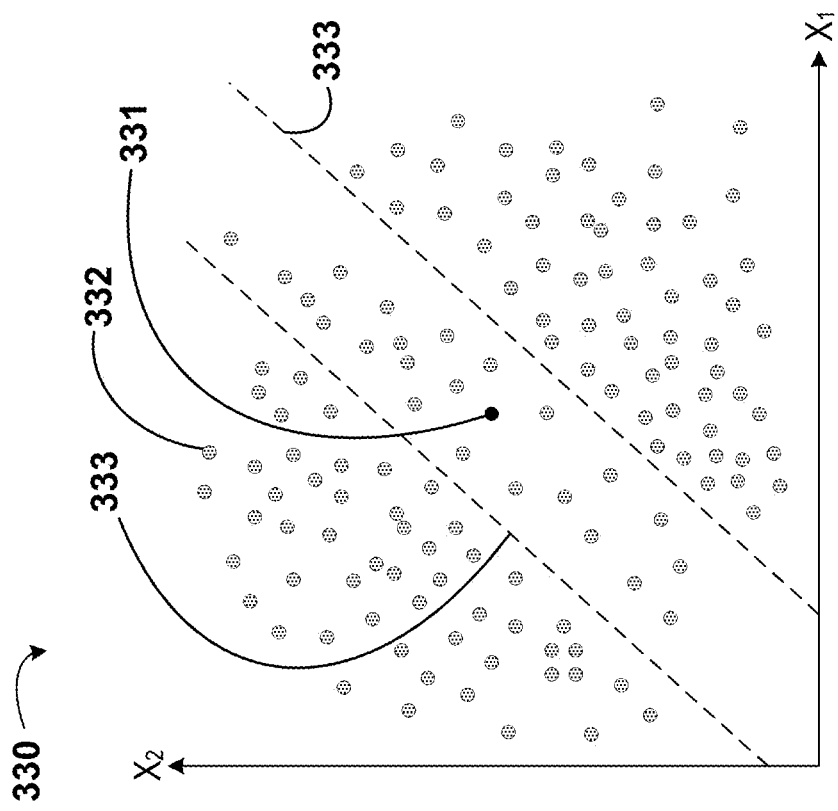
FIG. 3D is a graphical illustration of patient stratification, according to example embodiments.
Figure 3C:
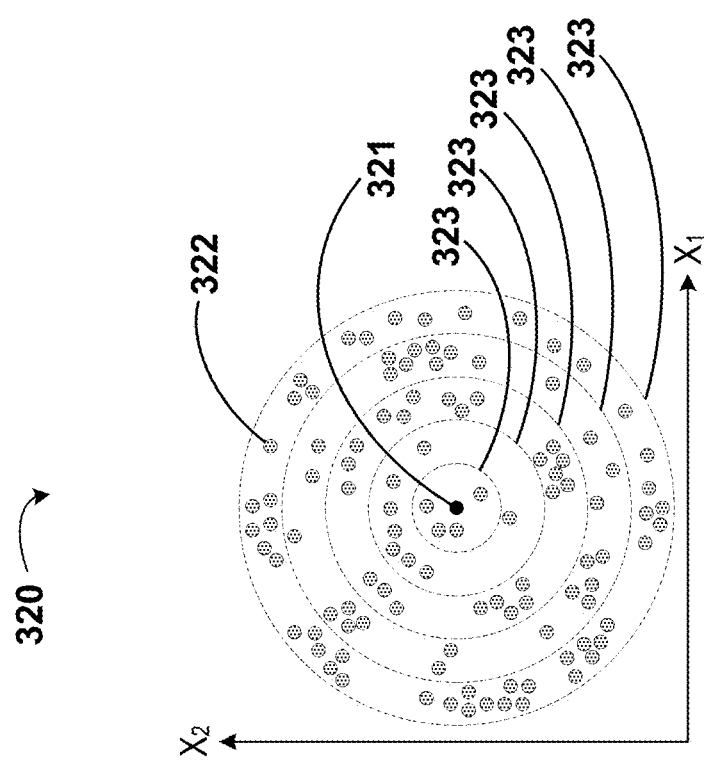
FIG. 3C is a graphical illustration of patient stratification, according to example embodiments.

FIG. 3C is a plot 320 of patient stratification, according to example embodiments. The plot 320 may illustrate semantic embeddings corresponding to a plurality of candidate phenotypes 322 (e.g., each corresponding to a candidate image of a candidate biological cell). Only one of the candidate phenotypes 322 is labelled in FIG. 3C, in order to avoid cluttering the figure. Each of the candidate phenotypes 322 in the plot 320 may have values corresponding to a plurality of dimensions that represent the respective semantic embedding. For example, the candidate phenotypes 322 in FIG. 3C may each have a value for a first dimension ($X_1$) and a second dimension ($X_2$). In alternate embodiments, semantic embeddings may include fewer than two dimensions or greater than two dimensions.

As illustrated in FIG. 3C, each of the candidate phenotypes 322 may fall within a phenotypic stratum 323 (the surfaces dividing the phenotypic strata 323 have been labeled in FIG. 3C, rather than the phenotypic strata themselves, which are the areas enclosed by the dividing surfaces). In alternate embodiments, only a subset of the candidate phenotypes 322 may fall within a phenotypic stratum 323 (e.g., some candidate phenotypes 322 may be outside of all phenotypic strata 323 bounds). In still other embodiments, one or more of the candidate phenotypes 322 may fall within multiple phenotypic strata 323 (as opposed to a single phenotypic stratum 323). In such embodiments, some of the phenotypic strata 323 may overlap. Also as illustrated in FIG. 3C, each of the phenotypic strata 323 may correspond to a contour surface relative to a target phenotype 321. In some embodiments, each of the contour surfaces corresponding to the phenotypic strata 323 may be spaced equidistantly from the target phenotype 321 (e.g., the contour surfaces may be represented by circles in two-dimensional embodiments or by spheres in three-dimensional embodiments). Alternatively, the contour surfaces may instead be shaped amorphously. Further, in some embodiments, each of the phenotypic strata 323 may correspond to different diseases, different states or phases of a single disease, or healthy states vs. diseased states.

Similar to FIG. 3C, FIG. 3D is a plot 330 of patient stratification that includes a target phenotype 331, candidate phenotypes 332, and phenotypic strata 333 (the surfaces dividing the phenotypic strata 333 have been labeled in FIG. 3D, rather than the phenotypic strata themselves, which are the areas between the dividing surfaces). Only one of the phenotypes 332 is labelled in FIG. 3D, in order to avoid cluttering the figure. Unlike the plot 320 of FIG. 3C, however, the phenotypic strata 333 do not correspond to contour surfaces relative to the target phenotype 331. As illustrated, the phenotypic strata 333 are defined by surfaces (e.g., which are defined by linear equations) that depend on values of the dimensions. As in FIG. 3D, in some embodiments, surfaces defining the phenotypic strata 333 may be non-intersecting. For example, the phenotypic strata 333 may be defined by surfaces that are parallel to one another (e.g., in the plot 330 of FIG. 3D, the phenotypic strata 333 are defined by parallel lines). Also as illustrated, the phenotypic strata 333 may not be defined by closed surfaces. Additionally or alternatively, phenotypic strata 333 may be defined based on groupings of candidate phenotypes 332. For example, the densities of candidate phenotypes 332 in the left-most phenotypic strata 333 and in the right-most phenotypic strata 333 are higher than the density of candidate phenotypes 332 in the middle phenotypic strata 333.

In some embodiments, the target phenotype 331 may not be used in the definition of the phenotypic strata 333. For example, the target phenotype 331 may be included simply as a reference point. For example, the target phenotype 331 may be a selected candidate phenotype 332 that is designated as the target phenotype 331 (e.g., the candidate phenotype 332 may be selected as the target phenotype 331 randomly or because it is the centermost candidate phenotype 332 in all dimensions). In yet other embodiments, there may be no target phenotype 331 at all (e.g., only a series of candidate phenotypes 332 grouped by phenotypic strata 333).

Figure 3E:
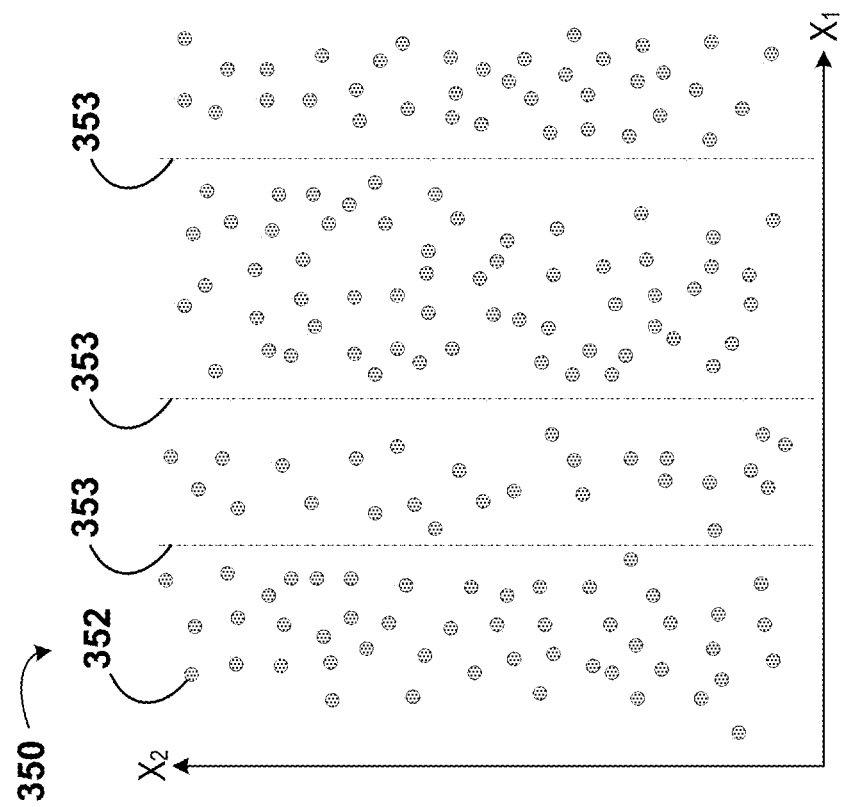
FIG. 3E is a graphical illustration of patient stratification, according to example embodiments.

Similar to FIGS. 3C and 3D, FIG. 3E is a plot 340 of patient stratification. The plot 340 includes a plurality of candidate phenotypes 342 and a plurality of phenotype strata 343 (the surfaces dividing the phenotypic strata 343 have been labeled in FIG. 3E, rather than the phenotypic strata themselves, which are the areas enclosed by the dividing surfaces). In the plot 340 of FIG. 3E, there is no target phenotype present. Only one of the candidate phenotypes 342 is labelled in FIG. 3E, in order to avoid cluttering the figure. As described above, the phenotypic strata 343 may be defined based on density variations of the candidate phenotypes 342. For example, based on such density variations, it may be inferred that regions of high densities of candidate phenotypes 342 correspond to a single phenotypic stratum 343. Alternatively, the phenotypic strata 343 may be defined based on various clustering techniques (e.g., spectral clustering, K-nearest neighbors clustering, machine-learned clustering, or according to a binomial classifier). As illustrated, the phenotypic strata 343 may correspond to surfaces of various shapes (e.g., circles, triangles, squares, and rectangles in two-dimensions and cubes, cylinders, cones, rectangular prisms, and pyramids in three-dimensions) and various sizes. Also as illustrated, the scale of a phenotypic stratum 343 in a first dimension ($X_1$) need not be the same as the scale of a phenotypic stratum 343 in a second dimension ($X_2$).

Figure 3F:
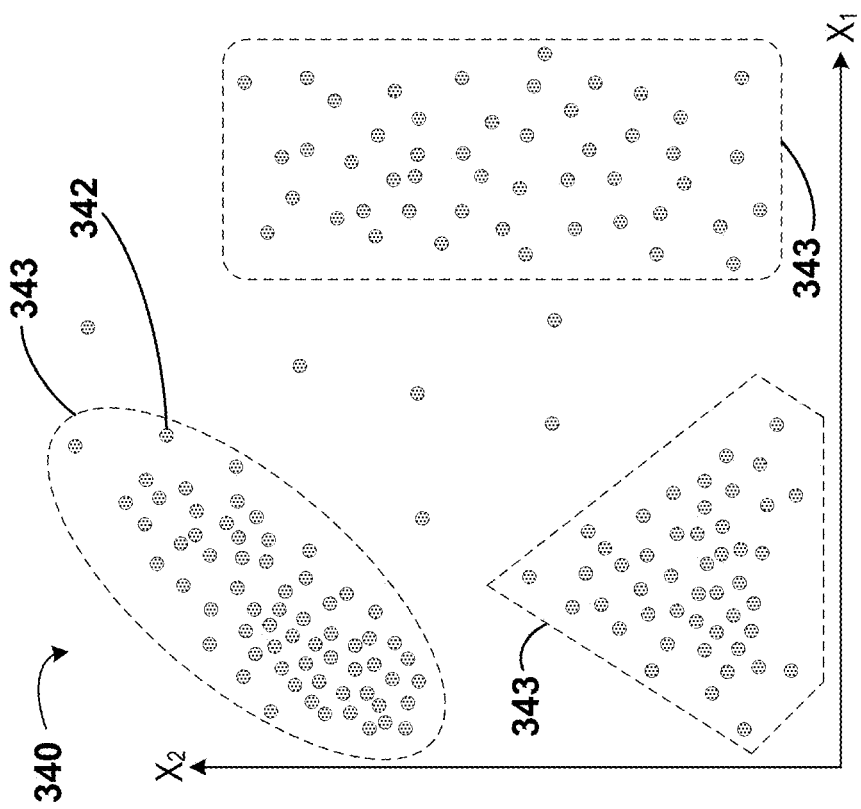
FIG. 3F is a graphical illustration of patient stratification, according to example embodiments.

Similar to FIGS. 3C-3E, FIG. 3F is a plot 350 of patient stratification. The plot 350 includes a plurality of candidate phenotypes 352. Only one of the candidate phenotypes 352 is labelled in FIG. 3F, in order to avoid cluttering the figure. The plot 350 also includes phenotypic strata 353 (the surfaces dividing the phenotypic strata 353 have been labeled in FIG. 3F, rather than the phenotypic strata themselves, which are the areas between the dividing surfaces). Further, the phenotypic strata 353 defined in FIG. 3F are only defined by their coordinate values in one dimension (e.g., only in $X_1$, because the phenotypic strata 353 are defined by vertical lines), rather than their coordinate values in a plurality of dimensions (e.g., as in FIG. 3D where the phenotypic strata 333 are defined by non-vertical, non-horizontal lines). In some embodiments, for example, the value of a given dimension (e.g., $X_1$) may directly correlate to the state of a disease (e.g., stage one or stage two).

Figure 3G:
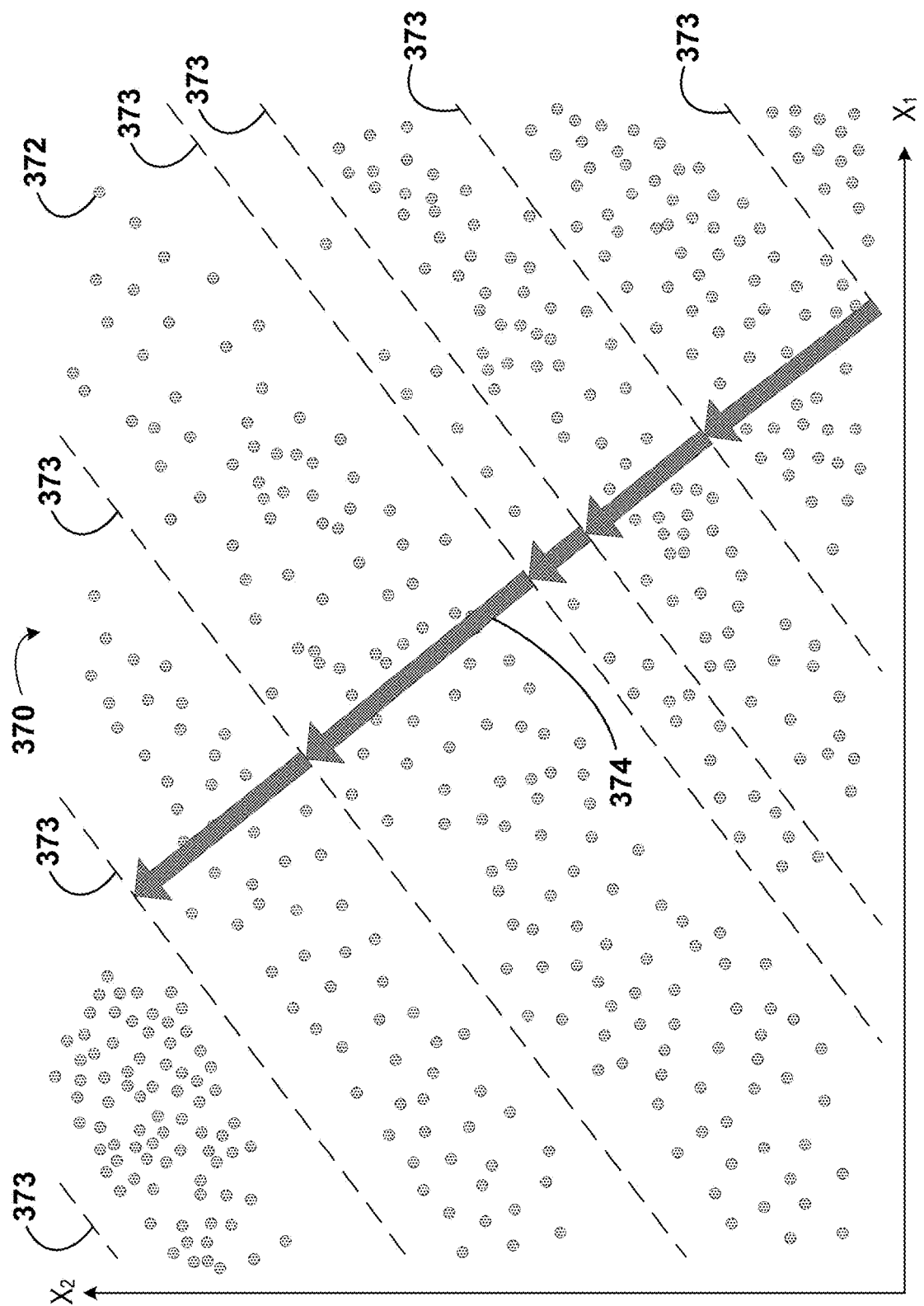
FIG. 3G is a graphical illustration of patient stratification, according to example embodiments.

FIG. 3G is a plot 370 of patient stratification for a series of candidate phenotypes 372. Only one of the candidate phenotypes 372 is labelled in FIG. 3G, in order to avoid cluttering the figure. The candidate phenotypes 372 may be divided into a plurality of phenotypic strata 373 (the surfaces dividing the phenotypic strata 373 have been labeled in FIG. 3D, rather than the phenotypic strata themselves, which are the areas between the dividing surfaces). The phenotypic strata 373 may be defined based on densities of the candidate phenotypes 372 in the plot 370.

Further illustrated in FIG. 3G are gradients 374. Each gradient 374 indicates the direction of greatest change (e.g., for each dimension ($X_1$ and $X_2$)) between adjacent phenotypic strata 373. In some embodiments, there may be gradients 374 even without identified phenotypic strata 373. For example, a gradient may correspond to a greatest rate of density change from a given point on the plot 370, even if phenotypic strata 373 have not been identified. Genetic mutations or applications of candidate treatment compounds, for example, may move a cell (e.g., along a gradient 374) from having a candidate phenotype 372 in one phenotypic stratum 373 to having a candidate phenotype 372 in another phenotypic stratum 373. Determining which candidate treatment compounds or genetic mutations will produce a movement of a biological cell along a gradient 374 (e.g., by reducing or increasing the values of one or more dimensions of the respective semantic embedding) may result in discovering a cure for a disease or a palliative treatment for a disease. Alternatively, discovering which genetic mutation will produce a movement of a biological cell along a gradient 374 may result in discovering a cause of a disease state or disease type.

Additionally or alternatively, candidate treatment compounds and genetic mutations may cause a biological cell to change dimensional values (e.g., change $X_1$ value and/or $X_2$ value), but not along a gradient. For example, applying a candidate treatment compound may result in a biological cell increasing or decreasing its values along one dimension (or a superposition of dimensions) in the respective semantic embedding. This can be used in the treatment or diagnosis of disease. For example, it may be discovered that a first candidate treatment compound increases a first dimension ($X_1$) value by 10 units/dose and a second candidate treatment compound increases a second dimension ($X_2$) value by 10 units/dose. If it is then desired to increase a candidate biological cell's first dimension ($X_1$) value by 20 units and to increase the candidate biological cell's second dimension ($X_2$) value by 30 units (e.g., to take the cell from an "unhealthy" phenotypic stratum 373 to a "healthy" phenotypic stratum 373), two doses of the first candidate treatment compound and three doses of the second candidate treatment compound may be applied to the candidate biological cell.

Figure 3H:
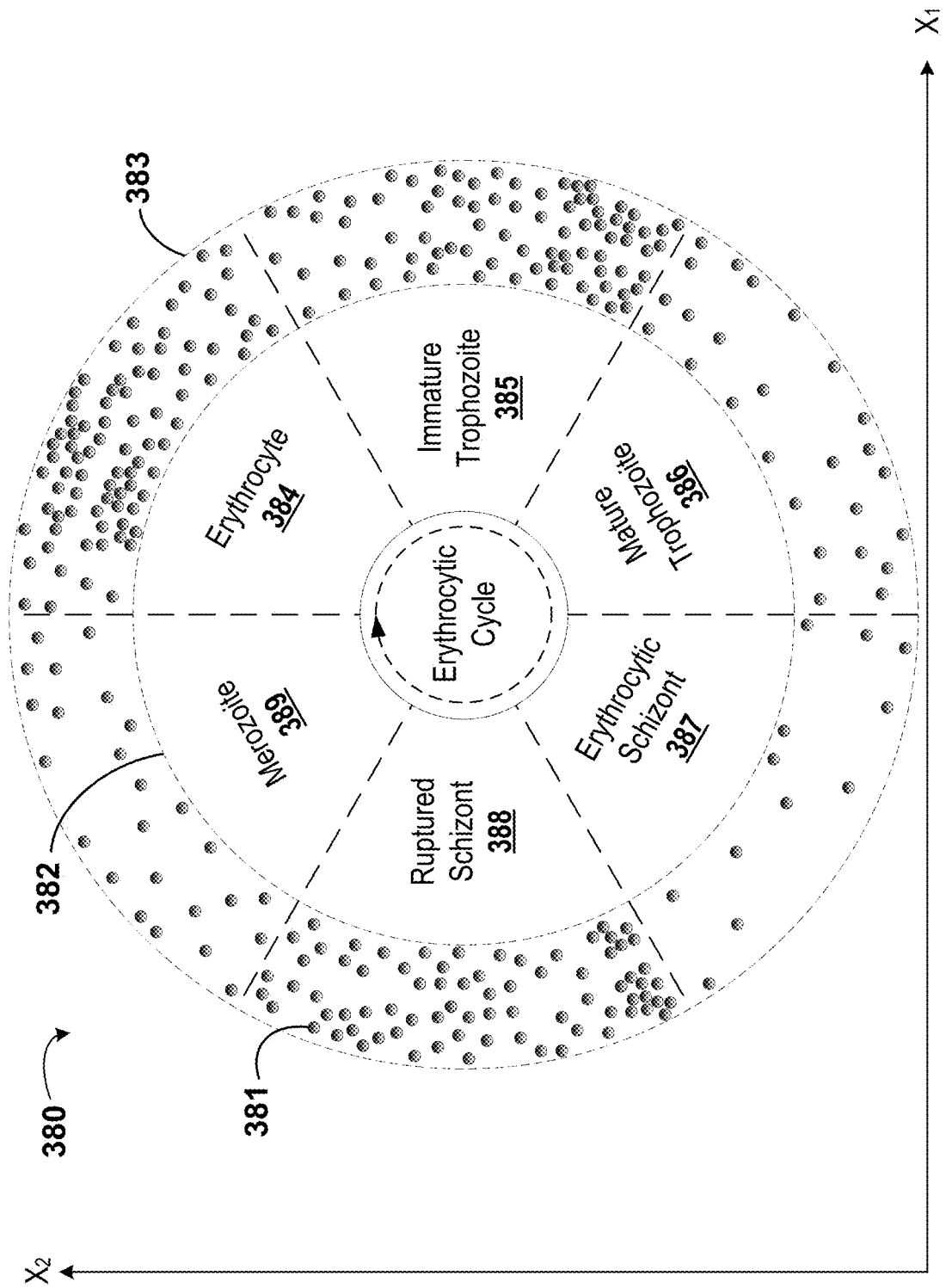
FIG. 3H is a graphical illustration of a topology enforced during training of a machine-learned, deep metric network model, according to example embodiments.

FIG. 3H is an illustration of a topology enforced during training of a machine-learned, deep metric network model, according to example embodiments. The topology may be a ring topology 380, as illustrated. Unlike any topologies in FIGS. 3A-3G (e.g., any shapes used to define phenotypic strata), the ring topology 380 may be enforced during training of the machine-learned, deep metric network (e.g., a constraint on the loss function may be imposed such that, during the training of the machine-learned, deep metric network model, a projection into a ring shape would result). For example, during training of the machine-learned, deep metric network, a constraint may be applied that indicates that a specific topology is naturally occurring within subjects of the type being studied, and should therefore be reflected in semantic embeddings generated by the machined-learned, deep metric network for subjects of the type being studied. The ring topology 380 may be defined by an inner-bounding ring 382 and an outer-bounding ring 383, with all semantic embeddings generated for the corresponding subjects being constrained such that they have dimensional values lying between the inner-bounding ring 382 and the outer-bounding ring 383.

As an example, the ring topology 380 illustrated in FIG. 3H may correspond to dimensional values within sematic embeddings of different malaria parasites 381 within a malaria population. Because malaria exhibits a lifecycle (e.g., an erythrocytic cycle), a ring topology 380 may correspond to different stages in the lifecycle. For example, different regions of the ring topology 380 may correspond to different combinations of values of a first dimension ($X_1$) and a second dimension ($X_2$). Semantic embeddings corresponding to different malaria parasites 381 generated using the machine-learned, deep metric network may be grouped based on their respective first dimension ($X_1$) and second dimension ($X_2$) values (e.g., into six stages of the erythrocytic cycle). For example, the semantic embeddings may be grouped into an erythrocyte stage 384, an immature trophozoite stage 385, a mature trophozoite stage 386, an erythrocytic schizont stage 387, a ruptured schizont stage 388, and a merozoite stage 389. Hence, by analyzing the combination of values for the first dimension ($X_1$) and the second dimension ($X_2$) for any semantic embedding generated for a respective malaria parasite 381 using the machine-learned, deep metric network, the stage of the erythrocytic cycle presently exhibited by the respective malaria parasite 381 can be determined.

It is understood that, while the ring topology 380 is depicted as two-dimensional in FIG. 3H, semantic embeddings generated using the machine-learned, deep metric model may be greater than two-dimensional, thereby resulting in topology that is greater than two-dimensional. For example, the ring topology 380 could instead be a toroidal topology in embodiments where the semantic embeddings are three-dimensional. In still other embodiments, where the semantic embeddings generated are n-dimensional, the ring topology 380 may instead be an n-dimensional ring.

In alternate embodiments (e.g., embodiments where different types of subjects are being perturbed, studied, and for which semantic embeddings are being generated), the topology may be a shape other than a ring. Some example alternate topologies are illustrated in FIGS. 3I-3L. It is understood that, while FIGS. 3I-3L illustrate two-dimensional topologies for two-dimensional semantic embeddings, other-dimensional topologies are possible for other-dimensional semantic embeddings (e.g., three-dimensional topology for three-dimensional semantic embeddings, two-dimensional topology for three-dimensional semantic embeddings, two-dimensional topology for four-dimensional semantic embeddings, three-dimensional topology for four-dimensional semantic embeddings, four-dimensional topology for four-dimensional semantic embeddings, n-dimensional topology for n-dimensional semantic embeddings, (n−1)-dimensional topology for n-dimensional semantic embeddings, etc.).

FIG. 3I is an illustration of a topology enforced during training of a machine-learned, deep metric network, according to example embodiments. The topology may be a linear topology 391, as illustrated. In some embodiments, during training of the machine-learned, deep metric network, a linear topology 391 may attempt to be enforced. Then, only if the linear topology 391 is found to be unenforceable based on the training data, may other types of topologies attempt to be enforced. The linear topology 391 may have upper and lower bounds that are defined when training the machine-learned, deep metric network, for example. Depending on a corresponding semantic embedding's location along the linear topology 391 (e.g., depending on values of the first dimension ($X_1$) and the second dimension ($X_2$)), subjects 390 may exhibit certain qualities (e.g., may exhibit qualities inherently or may correspond to certain perturbations applied to the respective subject 390). Further, the slope and/or intercepts of upper and/or lower bounds may of the linear topology 391 may correspond to features of the subjects 390 extracted during training of the machine-learned, deep metric network.

FIG. 3J is an illustration of a topology enforced during training of a machine-learned, deep metric network model, according to example embodiments. The topology may be an elliptical topology 392, as illustrated. The elliptical topology 392 may be enforced when training the machine-learned, deep metric network, for example. Depending on a corresponding semantic embedding's location within (or in other embodiments, outside of) the elliptical topology 392 (e.g., depending on values of the first dimension ($X_1$) and the second dimension ($X_2$)), subjects 390 may exhibit certain qualities (e.g., may exhibit qualities inherently or may correspond to certain perturbations applied to the respective subject 390). Further, the foci and/or major/minor axes of the elliptical topology 392 may correspond to features of the subjects 390 extracted during training of the machine-learned, deep metric network.

FIG. 3K is an illustration of a topology enforced during training of a machine-learned, deep metric network model, according to example embodiments. The topology may be a hexagonal topology 393, as illustrated. The hexagonal topology 393 may be enforced when training the machine-learned, deep metric network, for example. Depending on a corresponding semantic embedding's location within (or in other embodiments, outside of) the hexagonal topology 393 (e.g., depending on values of the first dimension ($X_1$) and the second dimension ($X_2$)), subjects 390 may exhibit certain qualities (e.g., may exhibit qualities inherently or may correspond to certain perturbations applied to the respective subject 390). Further, the interior angles and/or side lengths of the hexagonal topology 393 may correspond to features of the subjects 390 extracted during training of the machine-learned, deep metric network.

FIG. 3L is an illustration of a topology enforced during training of a machine-learned, deep metric network model, according to example embodiments. The topology may be a cruciform topology 394, as illustrated. The cruciform topology 394 may be enforced when training the machine-learned, deep metric network, for example. Depending on a corresponding semantic embedding's location within (or in other embodiments, outside of) the cruciform topology 394 (e.g., depending on values of the first dimension ($X_1$) and the second dimension ($X_2$)), subjects 390 may exhibit certain qualities (e.g., may exhibit qualities inherently or may correspond to certain perturbations applied to the respective subject 390). Further, the side lengths and/or location of intersection of the arms of the cruciform topology 394 may correspond to features of the subjects 390 extracted during training of the machine-learned, deep metric network.

In other embodiments, additional or alternative topologies may also be enforced during training of the machine-learned, deep metric network. For example, circular topologies, polygonal topologies, spherical topologies, ellipsoidal topologies, cylindrical topologies, conical topologies, hyperboloidal topologies, paraboloidal topologies, toroidal topologies, pyramidal topologies, polyhedral topologies, and/or topologies defined in a dimensional space having greater than three dimensions may also be enforced during training of the machine-learned, deep metric network. Still other topologies are also possible.

As described above, identification of a phenotypic stratum or a position relative to a given topology of a semantic embedding corresponding to a visual representation may provide information regarding the corresponding perturbed subject in the visual representation. For example, if the corresponding semantic embedding has values for its respective dimensions that place it within a given phenotypic stratum or within a given portion of a topology (e.g., a given portion of a ring topology corresponding to a given stage within a cycle), the perturbed subject may be classified as belonging to one or more groups (e.g., an unhealthy phenotype group or an erythrocytic schizont stage 387 group).

Additionally or alternatively, in some embodiments (e.g., embodiments having various types of subjects, biological and/or non-biological), classifying semantic embeddings/visual representations (and, therefore, ultimately classifying corresponding subjects), may include performing vector arithmetic on the semantic embeddings to determine to which of one or more groups the respective semantic embeddings/visual representations belong. Similar to above, as described with respect to similarity scores in FIGS. 3A and 3B, performing vector arithmetic may include determining a vector distance between a given point in n-dimensional embedding space and a respective semantic embedding. Further, performing vector arithmetic may include scaling, normalizing, translating, projecting onto a predetermined plane or axis, etc. one or more dimensions of a given semantic embedding to determine to which of one or more groups the semantic embedding belongs. The possible groups to which a semantic embedding/visual representation may belong may be enumerated in a list of groups, for example.

In still other embodiments, classifying the visual representations/semantic embeddings into one or more groups may include applying a classification model (e.g., a machine-learned classification model) to each of the semantic embeddings. The classification model may be trained to specifically pinpoint responses to any applied perturbation and/or to disregard any statistical variations inherently present across a population of subjects. For example, the classification model may be trained to ignore naturally occurring variations across biological cell subjects and to instead zero in on those variations that are induced by applied perturbations (e.g., applied candidate treatment compounds).

Additionally or alternatively, in some embodiments, the classification model may be trained using a human-in-the-loop procedure. Such a human-in-the-loop procedure may identify which variations (e.g., among visual representation training data and/or among generated semantic embeddings) correspond to notable differences (e.g., differences induced by applied perturbations) and which variations are attributable to randomness (e.g., naturally occurring variations and/or measurement noise). In still other embodiments, the classification model may be trained using isolation forests (e.g., based on an assumption that perturbation-induced anomalies should not have the same path lengths through random forests as ordinary variations) to identify which variations correspond to perturbation-induced differences and which variations are attributable to randomness. Additional or alternative types of classification models may also be used.

Based on the one or more groups into which a semantic embedding/visual representation is classified, one or more perturbations applied to the corresponding subject may be determined. For example, based on values of particular dimensions of a semantic embedding corresponding to a visual representation of a subject, the semantic embedding/visual representation may be classified into a certain group (e.g., because a semantic embedding has a value for a first dimension ($X_1$) of 27.2 and a value for a second dimension ($X_2$) of 18.6, the semantic embedding may correspond to an erythrocyte stage 384 of an erythrocytic cycle). Thus, the subject represented in the visual representation might also correspond to the certain group (e.g., the subject may be a malaria parasite in the erythrocyte stage 384). Using the group to which the subject belongs, effects, if any, of any perturbations applied to the subject can be determined. For example, if a specific wavelength of light at a certain intensity illuminated a subject, the effect of such a perturbation may be reflected in the group to which the subject belongs. By observing various perturbations applied to a variety of subjects within a population and the corresponding groups to which the visual representations/semantic embeddings of the subjects are assigned thereafter, a preferred perturbation from among the various perturbations may be identified. For example, if an erythrocyte stage 384 of an erythrocytic cycle is preferred for clinical reasons, an applied perturbation that promotes membership in the erythrocyte stage 384 among subjects to which the perturbation was applied may be preferred. Other perturbations that promote membership in non-desired groups may be disfavored.

FIG. 4A is a tabular illustration of an un-normalized data set 400 having a target phenotype and six candidate phenotypes, according to example embodiments. The use of a single target phenotype and six candidate phenotypes is purely by way of example. In various alternate embodiments, there may be greater or fewer target phenotypes and/or candidate phenotypes.

The target phenotype may correspond to a healthy phenotype or an unhealthy phenotype of a target biological cell of a target image, in various embodiments. In other embodiments, the target phenotype may correspond to a known disease state or mutation type. Alternatively, in some embodiments, the target phenotype may be defined based on optimized and/or desired values for each of the dimensions, as opposed to an actual target image of a target biological cell. For example, if $Y_1$ corresponded to a cellular size, the target phenotype may have a value of $Y_1$ such that a corresponding biological cell having the target phenotype has a specified surface area (e.g., 50 $\mu m^2$).

Further, the candidate phenotypes may correspond to candidate images of candidate biological cells acquired from various anatomical regions of a patient during a biopsy, treated with various concentrations of a candidate treatment compound, and/or treated with various candidate treatment compounds. The candidate images of such candidate biological cells may have been recorded from images of a multi-well sample plate. As illustrated, each phenotype in the un-normalized data set 400 may have values corresponding to various dimensions (e.g., $Y_1$ and $Y_2$) of a semantic embedding. In some embodiments, the various dimensions may correspond to human interpretable or non-human interpretable features of the semantic embeddings.

Figure 4B:
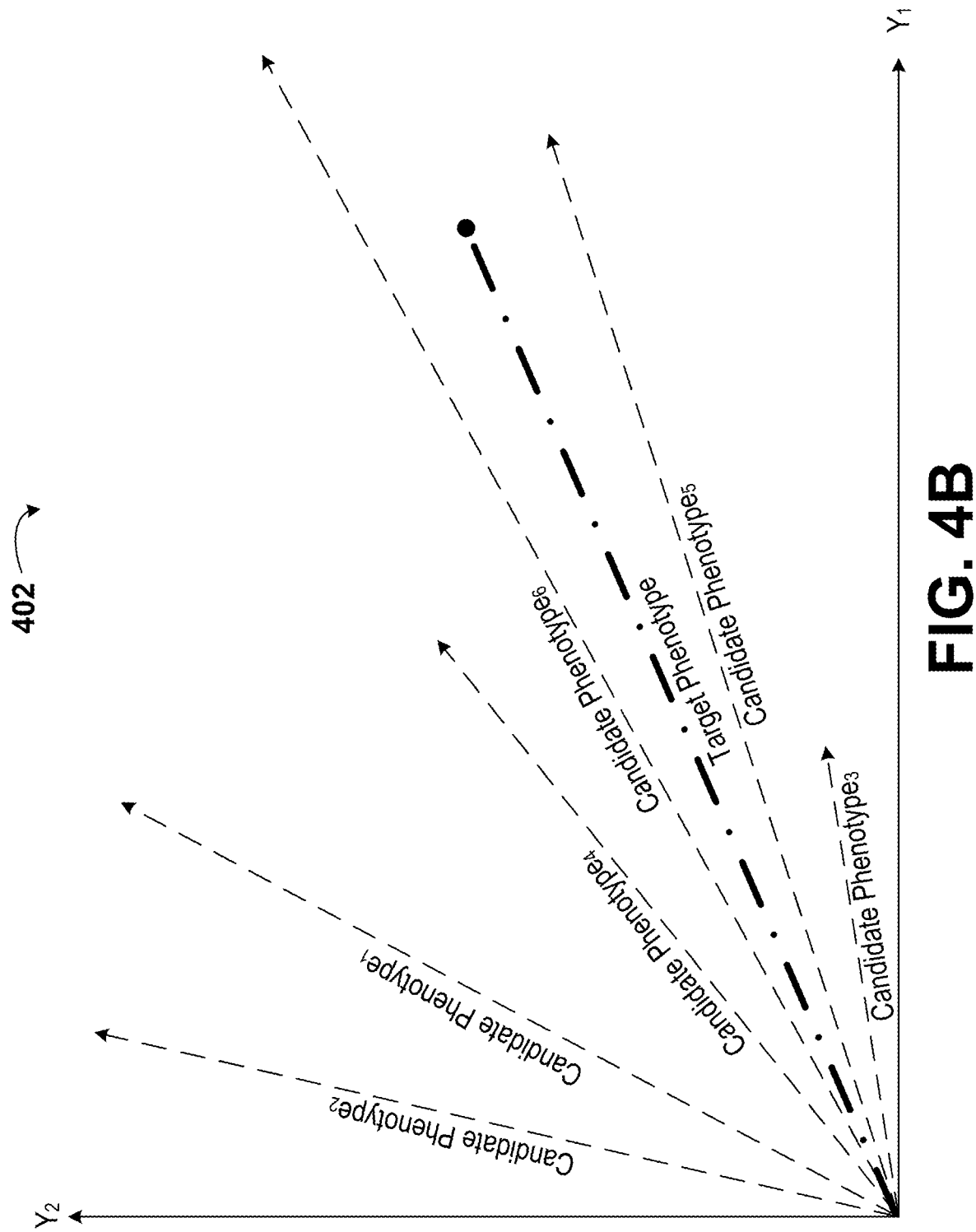
FIG. 4B is a graphical illustration of an un-normalized data set having a target phenotype and six candidate phenotypes, according to example embodiments.

FIG. 4B is a graphical illustration 402 of the un-normalized data set 400 having the target phenotype and the six candidate phenotypes (as illustrated in FIG. 4A), according to example embodiments. As illustrated, each of the target phenotype and the candidate phenotypes are represented as vectors in the two-dimensional space defined by the orthogonal dimensions $Y_2$ and $Y_1$. The phenotypes in FIG. 4B that are nearer to one another (i.e., those phenotypes whose vector endpoints are shorter distances away from one another) may be more similar to one another. For example, as illustrated in FIG. 4B, Candidate Phenotype$_2$ may be more similar to Candidate Phenotype$_1$ than it is to Candidate Phenotype$_4$. As another example, as illustrated in FIG. 4B, the Target Phenotype may be more similar to Candidate Phenotype$_5$ than it is to Candidate Phenotype$_3$.

FIG. 4C is a tabular illustration 404 of vector distances 405 between candidate phenotypes and a target phenotype of the un-normalized data set 400 illustrated in FIGS. 4A and 4B, according to example embodiments. The vector distances 405 may be calculated using the formula described with respect to FIG. 3A, for example. In some embodiments, the vector distances 405 may correspond to the similarity score between the candidate phenotypes and the target phenotype. In other embodiments, the vector distances 405 may correspond to the inverse of the similarity score between the candidate phenotypes and the target phenotype.

In some embodiments, the vector distances 405 between the target phenotype and the candidate phenotypes may be ranked (e.g., ordered ascendingly or decreasingly) to determine which of the candidate phenotypes is nearest to the target phenotype. Such a ranking may allow for a determination to be made regarding which of the candidate phenotypes is most similar to the target phenotype. Additionally or alternatively, the candidate phenotypes may be grouped into similarity sets based on one or more threshold distances or threshold similarity scores. For example, using the vector distances 405 illustrated in FIG. 4C, the candidate phenotypes may be grouped into three groups (e.g., one group whose vector distances to the target phenotype are between 0.00 and 3.00, a second group whose vector distances to the target phenotype are between 3.00 and 6.00, and a third group whose vector distances to the target phenotype are greater than 6.00). In such an example embodiment, there may be two threshold vector distances (one at 3.00 and one at 6.00). In other embodiments there may be greater or fewer numbers of threshold vector distances (e.g., 0, 1, 3, 4, 5, 6, 7, 8, 9, 10, 20, 50, 100, etc.).

In some embodiments, distances between candidate phenotypes may be calculated in addition to distances between the candidate phenotypes and the target phenotype. Such additional distance calculations may allow for further similarity analysis among candidate phenotypes.

FIG. 4D is a tabular illustration of a normalized data set 406 having a target phenotype and six candidate phenotypes, according to example embodiments. The normalized data set 406 may correspond to the un-normalized data set 400 illustrated in FIGS. 4A-4C after normalization. As illustrated, the normalized dimensions ($Y'_1$ and $Y'_2$) may correspond to the un-normalized dimensions ($Y_1$ and $Y_2$) after a normalization that includes scaling $Y_1$ by a scaling factor of 0.5. Also as illustrated, the normalization of the $Y_2$ components of the un-normalized data set 400 yielded equivalent values for the $Y'_2$ components of the normalized data set 406.

In some embodiments, the values of the second dimension ($Y_2$) may be multiplied by a non-unity scaling factor as well, in order to produce the normalized data set. Additionally or alternatively, in alternate embodiments, one or both of the dimensions of the normalized data set may be shifted by a certain amount with respect to the un-normalized data set. In alternate embodiments having additional dimensions (e.g., 64, 128, 192, or 256 dimensions), additional values for additional dimensions of the target phenotype and/or the candidate phenotypes may also be normalized to achieve a normalized data set.

The un-normalized data set 400 may be normalized to achieve the normalized data set 406 for multiple reasons. In some embodiments, one reason for normalization may be to generate a set of dimensions that have a mean of zero and a unit-variance (i.e., the normalization may include "whitening"). If all dimensions within a data set exhibit such a normalized quality, they may not be as prone to outliers strongly influencing the similarity scores.

Additionally or alternatively, another reason for normalization may be to account for typical variation within biological cells (e.g., based on the phenotypes of negative control groups or positive control groups). Because unperturbed biological cell populations may include a range of values across all or most of the dimensions of morphological variation, it may be important to identify those variations that indicate similarity between the candidate phenotypes and the target phenotype and those variations that arise due to common morphological variation. Accounting for typical variation may include finding dimensions of common morphological variation among the candidate phenotypes and then reducing the effect of "nuisances" (e.g., false positives) by normalizing those dimensions. Such a normalization process may increase or reduce the similarity score of candidate phenotypes that are relatively abnormal with respect to the similarity score of candidate phenotypes that are relatively common. Accounting for typical variation may include finding the eigenvalues and the eigenvectors of a covariance matrix of the dimensions using PCA, for example. Further, the transforms used during PCA may be applied to the values of the dimensions of the candidate phenotypes and the target phenotype to further normalize the dimensions.

Figure 4E:
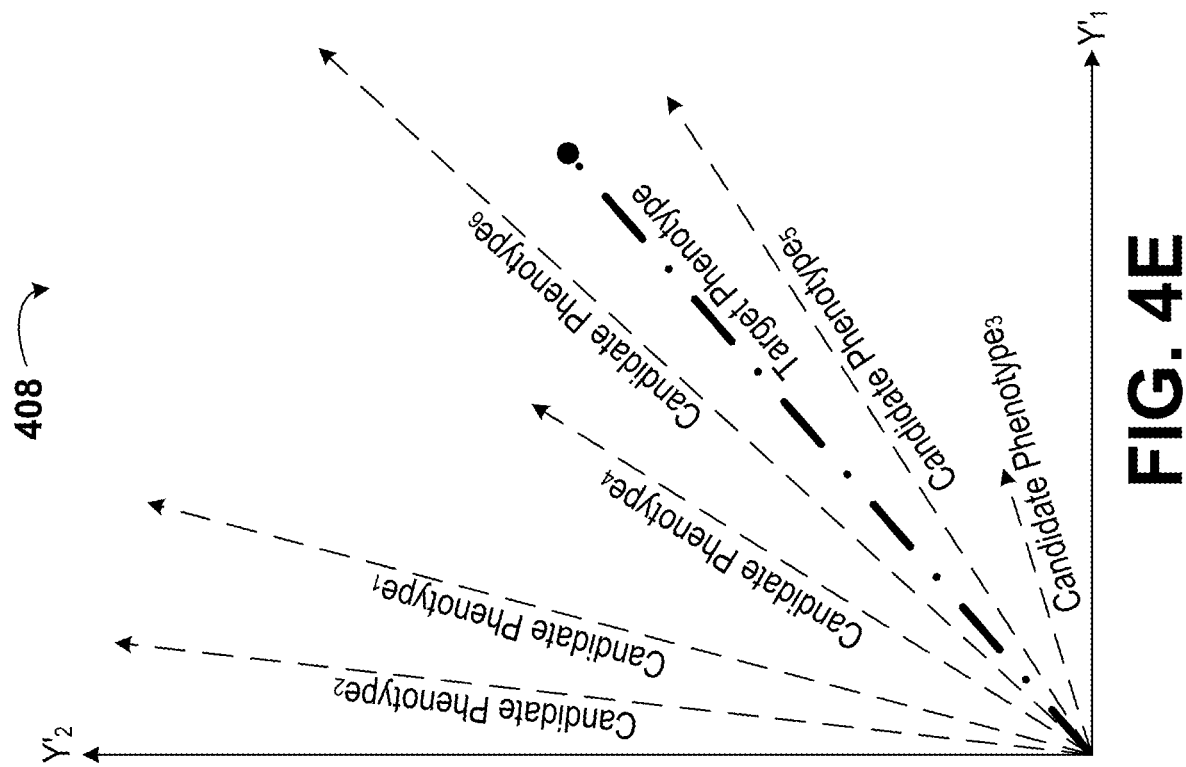
FIG. 4E is a graphical illustration of a normalized data set having a target phenotype and six candidate phenotypes, according to example embodiments.

FIG. 4E is a graphical illustration 408 of the normalized data set 406 having the target phenotype and the six candidate phenotypes, according to example embodiments. As illustrated, the phenotypes of the normalized data set 406 are closer to one another in the $Y'_1$ direction than the phenotypes of the un-normalized data set 400 are to one another in the $Y_1$ direction. Similar to FIG. 4B, the phenotypes in FIG. 4E that are nearer to one another (i.e., those phenotypes whose vector endpoints are shorter distances away from one another) may be more similar to one another.

FIG. 4F is a tabular illustration 410 of vector distances 411 between candidate phenotypes and a target phenotype of the normalized data set 406 illustrated in FIGS. 4D and 4E, according to example embodiments. Similar to the vector distances 405 illustrated in FIG. 4C, the vector distances 411 may be calculated using the formula described with respect to FIG. 3A, for example. Also similar to FIG. 4C, the vector distances 411 may correspond to the similarity scores or inverses of similarity scores and the vector distances 411 may additionally be ranked or grouped.

Figure 5A:
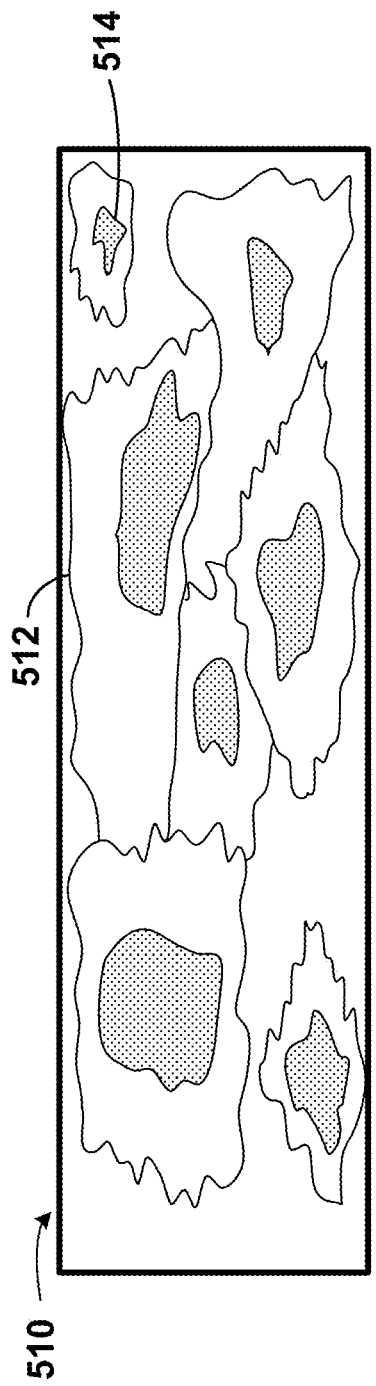
FIG. 5A is an illustration of an unscaled image of multiple cells, according to example embodiments.

FIG. 5A is an illustration of an unscaled image 510 of multiple cells 512, according to example embodiments. As described above, in other embodiments, other subjects may be analyzed using the processes described herein. For example, fibroblasts, malaria cells, yeast cells, yeast cultures, bacteria, bacterial cultures, fungus, fungal cultures, cancer cells, blood cells, malarial parasites, mitochondria, nuclei, axons, dendrites, induced pluripotent stem cells, biological cells from a given region of an organism, biological cells from a given tissue of an organism, biological cells from a given organ of an organism, biological cells from a given system of an organism, biological cell ensembles, tissues, organs, organoids, biological systems, organisms, groups of organisms, ecosystems, chemical compounds, crystals, metallic glasses, mixtures of metallic salts, semiconductors, metals, dielectrics, graphene, microelectromechanical systems (MEMS), and/or nanoelectromechanical systems (NEMS) may be analyzed using the processes described herein. Other subjects are also possible.

As illustrated in FIG. 5A, each cell 512 may have an identifiable nucleus 514. The cells 512 may include candidate biological cells and/or target biological cells. Further, the cells 512 may have healthy and/or unhealthy phenotypes. In addition, the cells 512 may be from different anatomical regions of a patient, from different patients, treated with different candidate treatment compounds, treated with different concentrations of the same candidate treatment compound, treated with different candidate treatment durations, or have a variety of mechanisms of action. Alternatively, the cells 512 in the unscaled image 510 may be in a negative control group or a positive control group.

The unscaled image 510 may be recorded photographically using one or more cameras (e.g., from above one or more wells of a multi-well sample plate), in some embodiments. Additionally, the cameras may include one or more optical filters to observe specific targeted regions of the cells 512. For example, the cells 512, or part of the cells 512, such as the nuclei 514, may be dyed with a fluorescent compound that fluoresces at a specific wavelength range. The optical filters may be configured to filter out light outside of the specific wavelength range. In such a way, the unscaled image 510 may be an image of only the targeted regions of the cells 512. In other embodiments, the unscaled image 510 may be a composite image that includes multiple channels (e.g., 1, 2, 3, 4, or 5 channels), each channel corresponding to a different section of the cells 512 and/or a different wavelength range.

The unscaled image 510 may be various sizes and have various aspect ratios in various embodiments. For example, the unscaled image 510 may be a standardized image size (e.g., 640 pixels by 480 pixels, 256 pixels by 256 pixels, 128 pixels by 128 pixels, or 100 pixels by 100 pixels) or have a standardized aspect ratio (e.g., width to height ratio of 4:3, 1:1, 2:1, 1:2, etc.). Alternatively, the unscaled image 510 may have an irregular image size and/or aspect ratio. For example, the image size and/or aspect ratio may depend on the device (e.g., camera or charge-coupled device, CCD) used to record the unscaled image 510.

In some embodiments, other types of visual representations of a subject may be captured and/or created (e.g., visual representations other than images like the unscaled image 510). Such visual representations may be generated using one or more imaging modalities. For example, three-dimensional visual representations or videographic representations may be captured of the subject. Further, in various embodiments (e.g., embodiments having various subjects), various imaging modalities may be used to capture a visual representation of a subject. For example, computed tomography, magnetic resonance imaging, positron emission tomography, ultrasound, x-ray computed tomography, x-ray diffraction, fluoroscopy, projectional radiography, single-photon emission computed tomography, scintigraphy, elastography, photoacoustic imaging, near-infrared spectroscopy, magnetic particle imaging, optoacoustic imaging, diffuse optical tomography, Raman spectroscopy, fluorescent microscopy, confocal microscopy, two-photon microscopy, hyperspectral analysis, transmission microscopy, electromagnetic scanning, differential interference contrast microscopy, multiphoton microscopy, dark-field microscopy, quantitative phase-contrast microscopy, near-field scanning optical microscopy, photo-activated localization microscopy, second harmonic imaging, holography, scanning electron microscopy, and/or tunneling electron microscopy may be used to capture a visual representation of a subject. Other imaging modalities or combinations of imaging modalities are also possible.

In some embodiments, the imaging modality used to generate the visual representation may perform background correction(s). For example, if photobleaching of one or more subjects occurs while imaging the subjects, that effect may be removed by the imaging modality when capturing the image (e.g., an image sensor used to capture the visual representation can have a coloration filter and/or neutral-density filter applied to compensate for the degree to which coloration and/or brightness would otherwise be affected by photobleaching when capturing the visual representation). Additionally or alternatively, background correction may be performed after obtaining a semantic embedding for the corresponding visual representation. For example, if a given background effect is understood to modify the value of a given dimension (e.g., the first dimension $X_1$) of a semantic embedding by a predetermined amount (e.g., increase the value of the first dimension $X_1$ by an amount of 10.0), the given background effect can be detected among semantic embeddings generated for visual representations and/or can be negated from such semantic embeddings (e.g., by subtracting 10.0 from the first dimension $X_1$ for the respective semantic embeddings). Other techniques of accounting for background correction are also possible.

Further, the unscaled image 510 may be received by a computing device to perform image analysis and comparison (e.g., using a machine-learned, deep metric network). Prior to performing image analysis, the unsealed image 510 may be transformed in one or more ways. Alternatively, in some embodiments, the computing device may analyze the unsealed image 510 in the format it is received, without manipulating or transforming the unsealed image 510 (e.g., because the unsealed image 510 is already an appropriate size/scale for interpretation using a machine-learned, deep metric network model or because the machine-learned, deep metric network model can be used to interpret images of any size or scale).

Figure 5B:
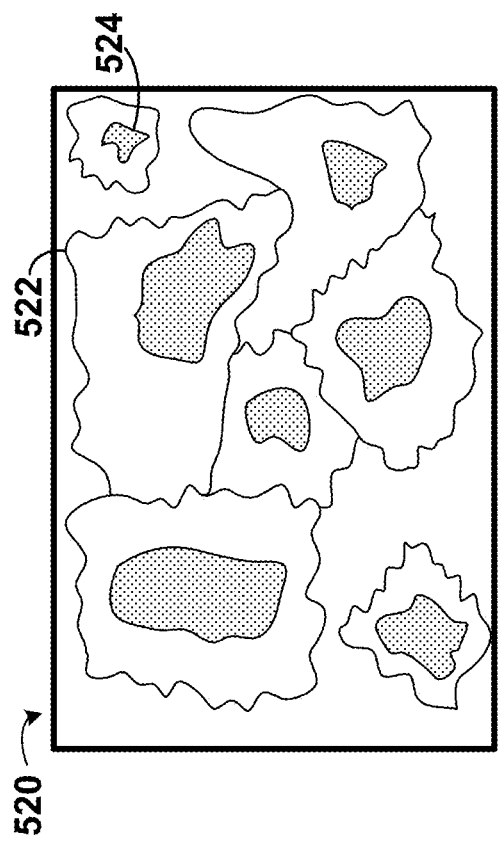
FIG. 5B is an illustration of a scaled image of multiple cells, according to example embodiments.

FIG. 5B is an illustration of a scaled image 520 of multiple cells 522, according to example embodiments. As illustrated, each cell 522 may have an identifiable nucleus 524. The scaled image 520 may be a scaled version of the unsealed image 510, for example. As illustrated, the unsealed image 510 of FIG. 5A may be transformed into the scaled image 520 of FIG. 5B by scaling the horizontal direction of the image by a factor between 0.0 and 1.0 (e.g., 0.5). The scaled image 520 may have an appropriate size (e.g., 640 pixels by 480 pixels, 256 pixels by 256 pixels, 128 pixels by 128 pixels, or 100 pixels by 100 pixels) or aspect ratio (e.g., width to height ratio of 4:3, 1:1, 2:1, 1:2, etc.) to be interpretable using the machine-learned, deep metric network.

The scaling illustrated in FIG. 5B may be one of a number of transformations performed on the unsealed image 510 prior to analysis, by a computing device, of the image using a machine-learned, deep metric network model.

Figure 5C:
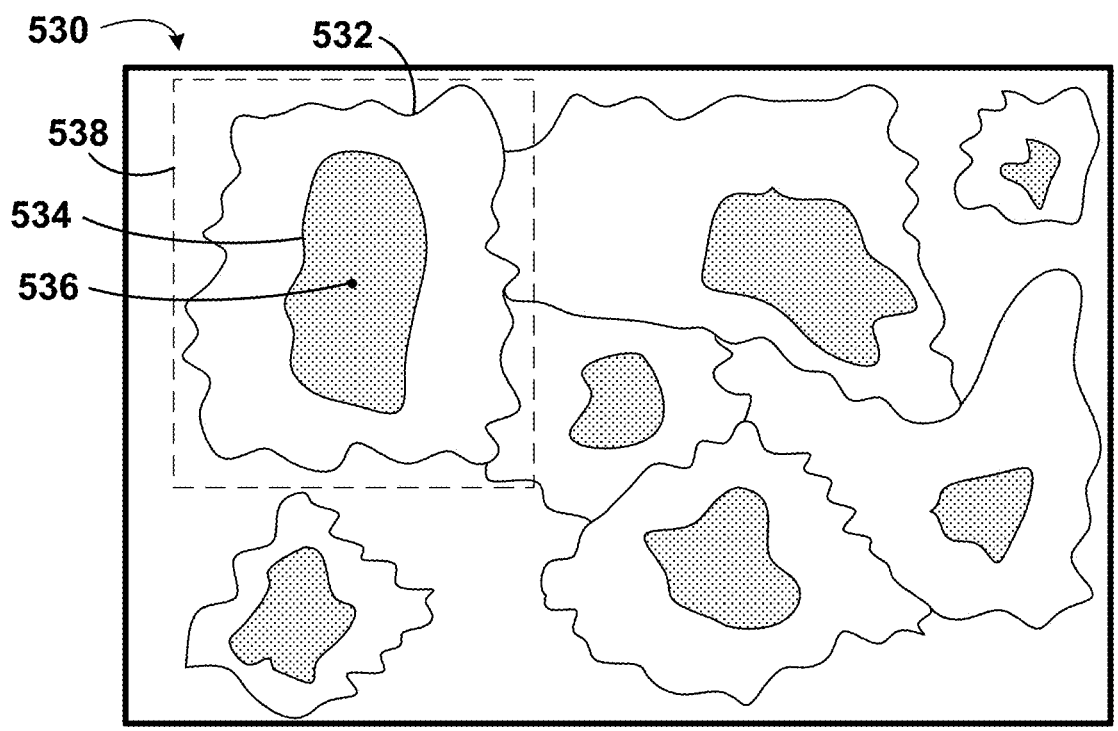
FIG. 5C is an illustration of a single-cell selection process in an image, according to example embodiments.

FIG. 5C is an illustration of a single-cell selection process 530 in an image, according to example embodiments. The single-cell selection process 530 may be an additional method used to transform an unsealed image (e.g., the unsealed image 510 illustrated in FIG. 5A) prior to analysis using a machine-learned, deep metric network model. The image originally received by a computing device may include multiple biological cells 532. Each cell may have identifiable features, such as a nucleus 534, for example. As illustrated, the single-cell selection process 530 may include determining a center 536 of one of the cells 532. In embodiments where multiple cells 532 are included in the image (e.g., the embodiment illustrated in FIG. 5C), the single cell that is selected out of the group of cells 532 may be selected at random. Alternatively, the cell closest to a certain location of the image may be selected (e.g., the top-leftmost cell, the top-rightmost cell, the bottom-leftmost cell, the bottom-rightmost cell, or the cell closest to the center of the image). In other embodiments, a user of a computing device may manually select one of the cells 532.

Determining the center 536 of one of the cells 532 may include determining the location of the nucleus 534 of the respective cell 532. Additionally or alternatively, determining the center 536 of one of the cells 532 may include determining a horizontal center and/or a vertical center of the nucleus 534. Finding the nucleus 534 and/or horizontal and/or vertical centers of the nucleus 534 may include a computing device scanning the image for regions of a specific color and/or shape that corresponds to the shape of the nucleus 534. The color may be defined by a dye that targets the nucleus 534 (e.g., 4',6-diamidino-2-phenylindole, DAPI, which targets adenine-thymine pairs within deoxyribonucleic acid, DNA), for example. Determining the location of the nucleus 534 and/or the center 536 of the cell 532 may be completed using a computing device performing alternative image processing techniques in alternate embodiments.

Further, the single-cell selection process 530 may include selecting a region 538 of the image surrounding the center 536 of the nucleus 534. The region may be selected based on a typical shape (e.g., circular, rectangular, or elliptical), size (e.g., 128 pixels by 128 pixels), and/or orientation (e.g., vertical, horizontal, or at a 45 degree angle with respect to the orientation of the image) of biological cells within the image. The typical shape, size, and/or orientation of the biological cells may be based on a predetermined type of cell (e.g., skin cell, blood cell, cancer cell, nerve cell, muscle cell, pluripotent stem cell, etc.) within the image and/or a predetermined expected phenotype of the cell (e.g., healthy phenotype, unhealthy phenotype, etc.) within the image. For example, if the cells in the image were expected to be red blood cells having a healthy phenotype, a size and shape of the selected region 538 may be based on typical sizes and shapes of healthy red blood cells at a magnification level corresponding to the magnification level used to record the image.

The single-cell selection process 530 may select a region that is slightly larger or smaller than a region of the image occupied by one cell (e.g., if the expected size/shape/orientation of the cell does not match the actual size/shape/orientation of the cell being analyzed). For example, the region 538 selected in FIG. 5C encompasses a region slightly larger than the cell 532, thereby also encompassing portions of neighboring cells. Alternatively, in some embodiments, the region selected by the process may intentionally include multiple cells. For example, the shape and size of the region may be based on typical sizes and shapes of regions having multiple cells (e.g., 2, 3, 4, 5, 10, 20, etc. cells). Further, the process for selecting a region having multiple cells may include selecting multiple nuclei or finding the horizontal and/or vertical centers of multiple nuclei.

Figure 5D:
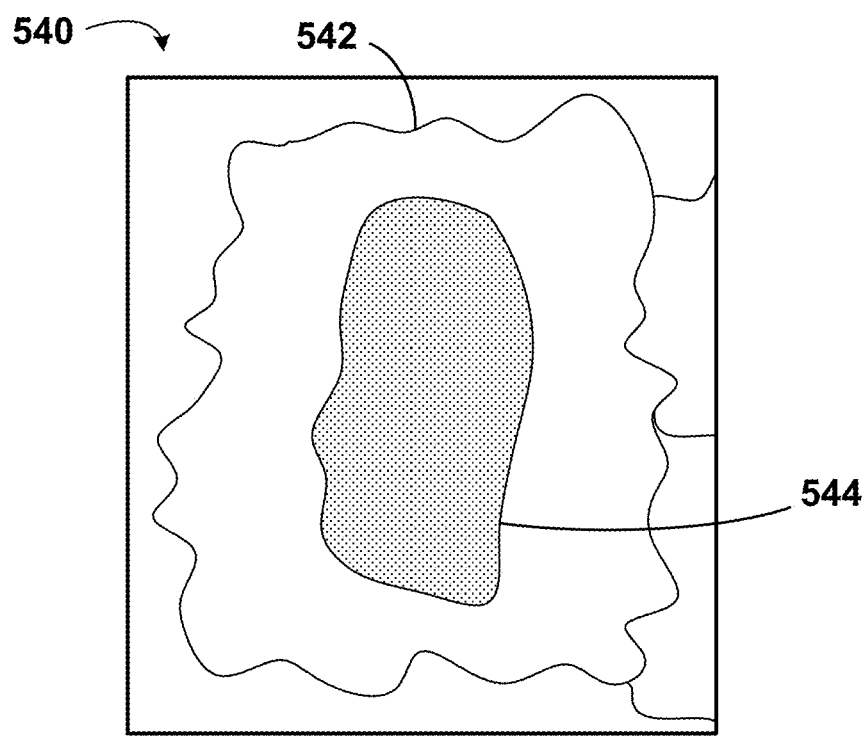
FIG. 5D is an illustration of a single-cell image, according to example embodiments.

FIG. 5D is an illustration of a single-cell image 540, according to example embodiments. The single-cell image 540 may have been generated by performing the single-cell selection process 530 illustrated in FIG. 5C, for example. Additionally, the single-cell image 540 may be extracted from an unscaled image (e.g., the unscaled image 510 illustrated in FIG. 5A) or a transformed version of an unscaled image (e.g., the scaled image 520 illustrated in FIG. 5B). As illustrated, the single-cell image 540 may include a cell 542 having a nucleus 544. The cell 542 and the nucleus 544 may be scaled or unscaled versions of the cell 532 and the nucleus 534 illustrated in FIG. 5C, for example. Further, the single-cell image 540 may be compared with other single-cell images using a machine-learned, deep metric network model in order to determine phenotypic similarity, in some embodiments.

Figure 5E:
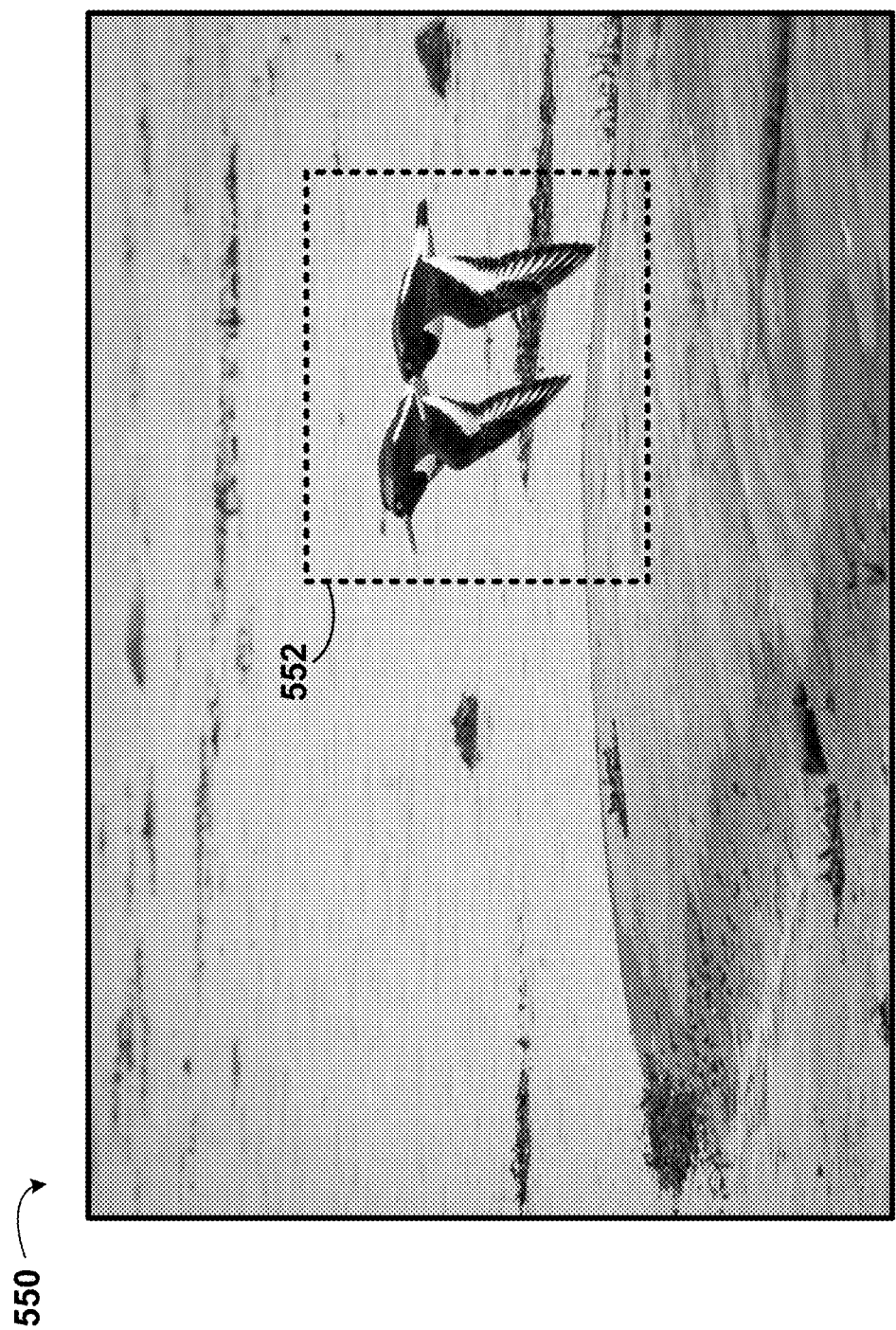
FIG. 5E is an illustration of a patch selection, according to example embodiments.

The single-cell selection process 530 illustrated in FIG. 5C is an example of a broad class of techniques referred to as "patch selection techniques" used to identify subsets of images (or subsets of other types of visual representations) upon which image analysis (e.g., generation of a corresponding semantic embedding using the machine-learned, deep metric network) will be performed. FIG. 5E is an illustration of another patch selection technique 550, according to example embodiments. The patch selection technique 550 may be used to select a patch 552 of the visual representation (e.g., the image) for analysis using the machine-learned, deep metric network model.

The patch selection technique 550, itself, may be performed using a machine-learned process, in some embodiments. For example, the patch selection technique 550 may be performed using a machine-learned process that includes an attention mechanism used to define regions of the visual representation that are of threshold interest level to be selected. For example, as illustrated, the birds in the patch 552 may correspond to types of subjects to be analyzed using semantic embeddings, so the attention mechanism may be trained to only select those regions of the visual representation that include subjects. As such, the attention mechanism may be used to define which regions of a preliminary visual representation are of threshold interest level to be selected by the patch selection. In other embodiments, the patch selection technique 550 may be performed using a set of heuristics (e.g., hard-coded rules to select the location of highest intensity within an image; to select a center-region of an image; to select the location of an image with the largest red, green, and/or blue value; etc.).

In embodiments where the visual representations are n-dimensional visual representations, the selected patch 552 may, likewise, be n-dimensional. Further, in embodiments where the visual representations are videographic representations, the selected patch 552 may include multiple regions of multiple frames of the videographic representation. The regions in the various frames may not necessarily be the same geometric regions of each frame. For example, if a subject of interest (e.g., pedestrian) is moving through a scene of the videographic representation, the regions of the various frames may move geometrically across the scene as well to track the motion of the subject.

Figure 6B:
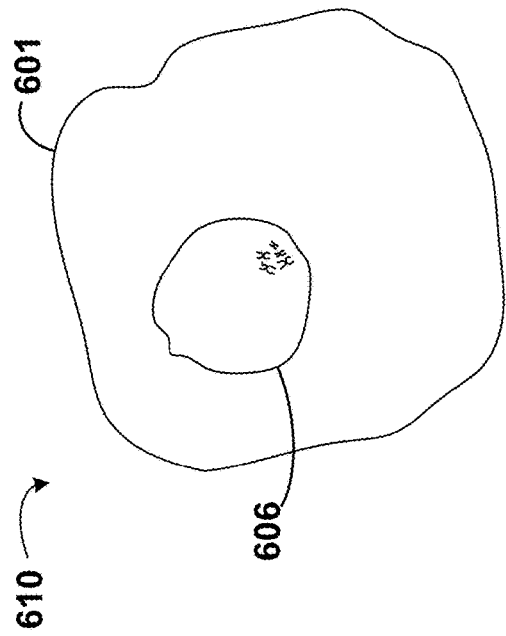
FIG. 6B is an illustration of a channel that is part of a scientific image, according to example embodiments.
Figure 6D:
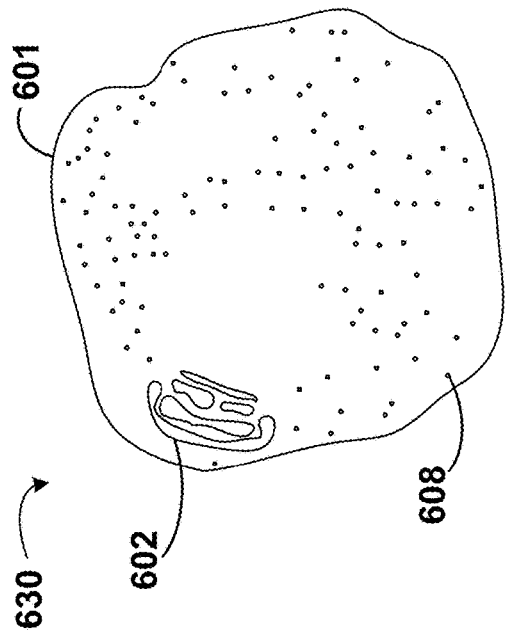
FIG. 6D is an illustration of a channel that is part of a scientific image, according to example embodiments.
Figure 6A:
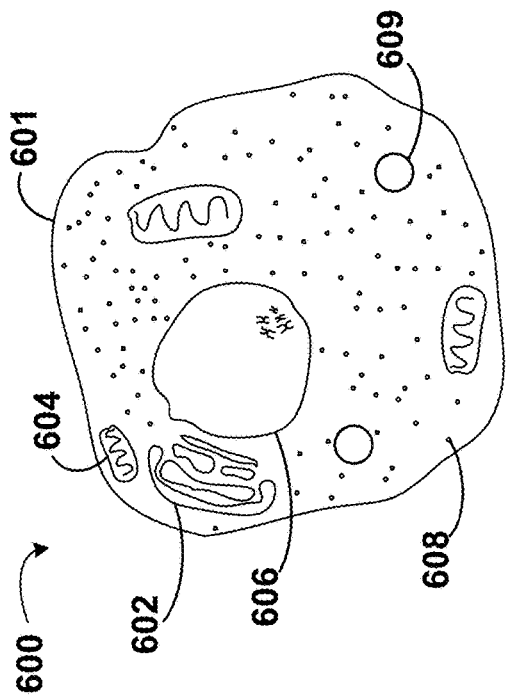
FIG. 6A is an illustration of a composite scientific image, according to example embodiments.

FIG. 6A is an illustration of a composite scientific image 600, according to example embodiments. The composite scientific image 600 may include one or multiple channels (e.g., 2, 3, 4, 5, 10, 15, or 20 channels) in various embodiments. The composite scientific image 600 illustrated in FIG. 6A includes a biological cell 601 having multiple organelles. As illustrated, the composite scientific image 600 of the cell 601 includes a golgi body 602, mitochondria 604, a nucleus 606 (e.g., contain DNA), ribosomes 608, and vacuoles 609. In alternate embodiments, the composite scientific image may show additional or alternative regions of the cell (e.g., a nucleolus, a cytoskeleton, a cellular membrane, an endoplasmic reticulum, a vesicle, a lysosome, or a centrosome).

The composite scientific image 600 may be a target image of a target biological cell having a target phenotype, for example. In some embodiments, target images may include pixel data. Additionally or alternatively, target images may include an image identification (ID) and a reference. In alternate embodiments, the composite scientific image 600 may be a candidate image of a candidate biological cell having a candidate phenotype. Candidate images, similarly, may include pixel data and/or an image ID/reference. In some embodiments, the composite scientific image 600 may be a scaled or cropped version of a raw image recorded by a camera. Further, the composite scientific image 600, either as a whole or individually by channel, may be compared to other scientific images using a machine-learned, deep metric network.

Each of the channels may represent different target regions of the cell 601 or different target components of the cell 601, in some embodiments. The channels may be separated based on wavelength. For example, a dye may be used to target different components of the cell 601, and each channel may be recorded by one or more cameras with selective filters that only record light within a given wavelength band, such that only the targeted components emitting light within the given wavelength band may be measured. In alternate embodiments, various channels of the composite scientific image 600 may be distinguished based on other factors. For example, in some embodiments, the composite scientific image may be defined such that the composite scientific image has three channels, with the first channel being a region defined to be the top third of the image, the second channel being a region defined to be the middle third of the image, and the third channel being a region defined to be the bottom third of the image. Other delineations of channels within the composite scientific image are also possible.

FIG. 6B is an illustration of a channel 610 that is part of a scientific image, according to example embodiments. For example, the channel 610 may be a component of the composite scientific image 600 illustrated in FIG. 6A. The channel 610 illustrated in FIG. 6B may only show targeted regions or components of the cell 601 based on a fluorescent compound that is excited by an electromagnetic source, a chemical dye, or a chemiluminescent compound. The targeted regions or components illustrated in FIG. 6B may be those regions that are to be investigated according to a given study, for example. As illustrated, the channel 610 of FIG. 6B shows the nucleus 606 of the cell 601.

Figure 6C:
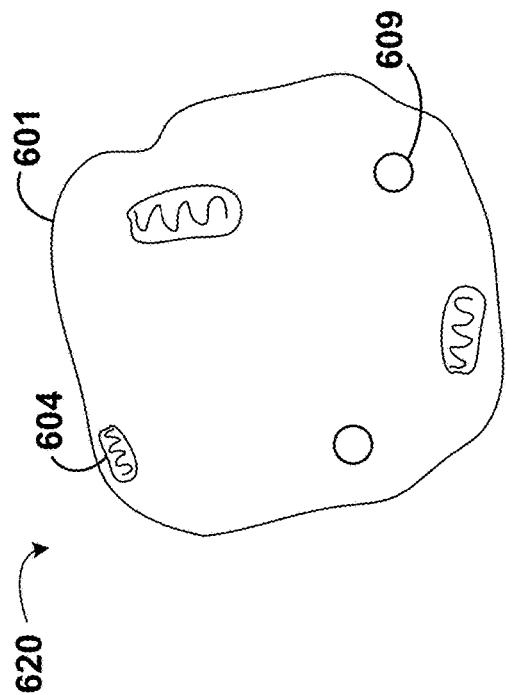
FIG. 6C is an illustration of a channel that is part of a scientific image, according to example embodiments.

Similar to FIG. 6B, FIG. 6C is an illustration of a channel 620 that is part of a scientific image (e.g., the composite scientific image 600 illustrated in FIG. 6A), according to example embodiments. As illustrated, the channel 620 of FIG. 6C shows the mitochondria 604 and the vacuoles 609 of the cell 601.

Similar to FIG. 6B, FIG. 6D is an illustration of a channel 630 that is part of a scientific image (e.g., the composite scientific image 600 illustrated in FIG. 6A), according to example embodiments. As illustrated, the channel 630 of FIG. 6D shows the golgi body 602 and the ribosomes 608 of the cell 601.

Figure 7A:
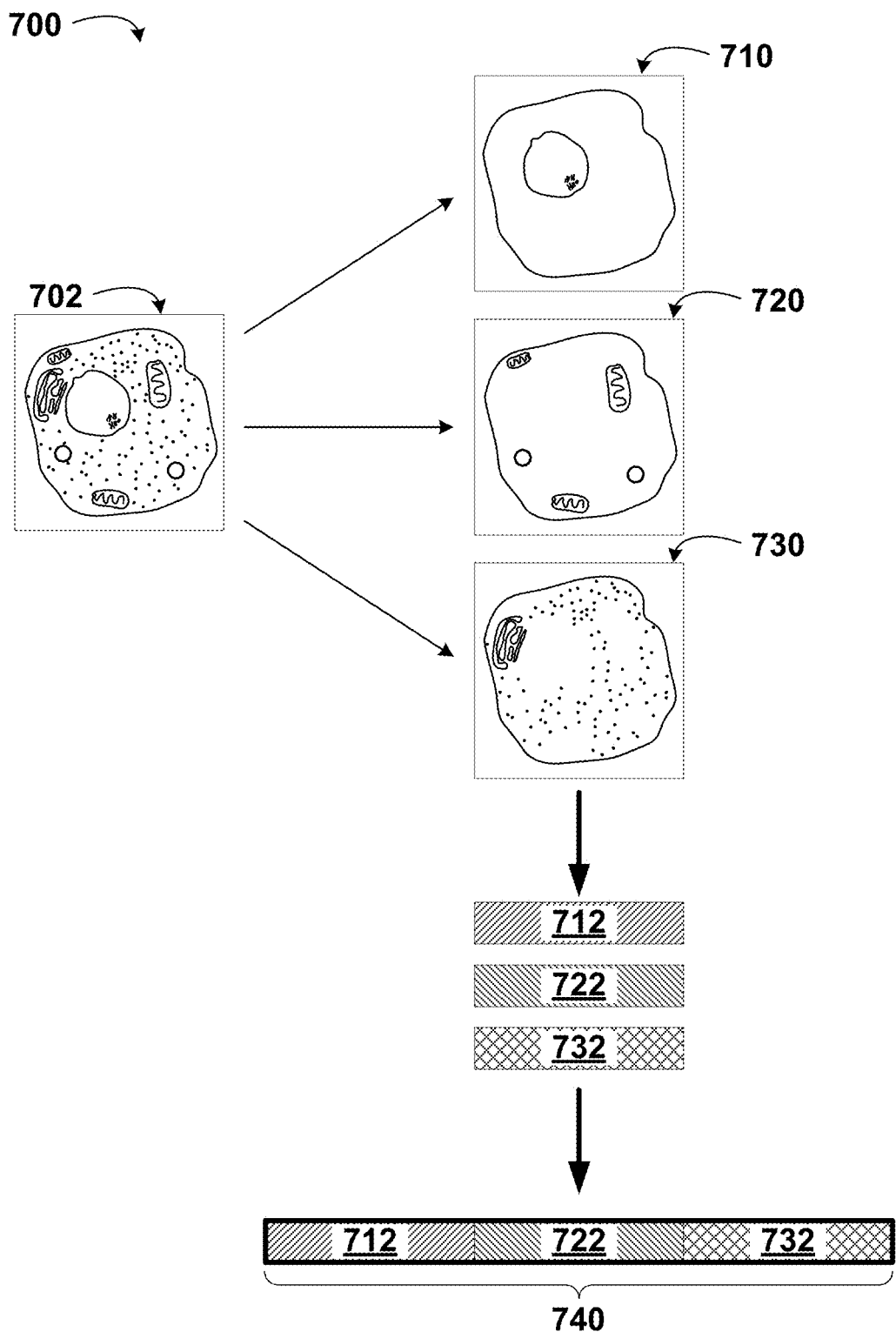
FIG. 7A is an illustration of a process, according to example embodiments.

FIG. 7A is an illustration of a process 700, according to example embodiments. The process 700 may generate a semantic embedding for a composite scientific image 702, for example, using a machine-learned, deep metric network model. The semantic embedding may then allow the composite scientific image 702 to be compared to other images. The composite scientific image 702 may be a scientific image of one or more cells, for example. Further, the scientific image 702 may be a target image of a target biological cell having a target phenotype or a candidate image of a candidate biological cell having a candidate phenotype, in various embodiments. The composite scientific image 702, as illustrated, may be similar to the composite scientific image 600 illustrated in FIG. 6A (e.g., may be a scaled version of the composite scientific image 600 illustrated in FIG. 6A).

A composite scientific image may include one or more channels (e.g., 1, 2, 3, 4, 5, 10, 15, or 20 channels). By way of example, the composite scientific image 702 illustrated in FIG. 7A includes three channels (a first channel 710, a second channel 720, and a third channel 730). Each channel in a composite scientific image may have a given bit depth (e.g., 4, 8, 16, 32, 64, or 128 bit depth). The bit depth of each channel of a composite scientific image may be the same as one another or different, depending on embodiment.

One step in the process 700 of obtaining a semantic embedding (e.g., by a computing device) for the composite scientific image 702 may include separating the channels within the composite scientific image 702. In some embodiments, each of the individual channels from the composite scientific image 702 may be individually stored in volatile and/or non-volatile memory (e.g., in a random access memory, RAM, and/or in a read-only memory, ROM, such as a hard drive).

An additional step of the process 700 of obtaining a semantic embedding for the composite scientific image 702 may include obtaining a semantic embedding for each respective channel 710, 720, 730 of the composite scientific image 702. As illustrated, a first semantic embedding 712 may be obtained that corresponds to the first channel 710, a second semantic embedding 722 may be obtained that corresponds to the second channel 720, and a third semantic embedding 732 may be obtained that corresponds to the third channel 730.

The semantic embeddings obtained for each channel may correspond to semantic embeddings that are interpretable using a machine-learned, deep metric network. For example, each semantic embedding obtained for each channel may include equivalent dimensions to those of the machine-learned, deep metric network that were previously learned using training data (e.g., consumer photographic training data arranged into three-image sets). In addition to including equivalent dimensions (i.e., dimensions defining corresponding image qualities), the semantic embeddings obtained for each channel may include an equivalent number of dimensions to those of the machine-learned, deep metric network model. In some embodiments, the semantic embeddings 712, 722, 732 obtained for each channel may have 16, 32, 64, 96, or 128 dimensions, for example.

In addition, the process 700 of obtaining a semantic embedding for the composite scientific image 702 may include concatenating the first semantic embedding 712, the second semantic embedding 722, and the third semantic embedding 732 into a unified semantic embedding 740. In other embodiments where the composite scientific image 702 includes greater or fewer than three channels, the number of semantic embeddings concatenated to form a unified semantic embedding may vary. Because the unified semantic embedding 740 is a composite of multiple single-channel semantic embeddings, the unified semantic embedding 740 may have additional dimensionality. For example, if each of the single-channel semantic embeddings includes 64 dimensions, the unified semantic embedding 740 may have 192 dimensions (3×64). If instead there were one channel having a single-channel semantic embedding with 64 dimensions, the unified semantic embedding may have 64 dimensions. Further, if there were five channels having single-channel semantic embeddings with 96 dimensions, the unified semantic embedding may have 480 dimensions (5×96), and so on and so forth.

In some embodiments, additional dimensionality reduction may be performed. For example, dimensionality reduction may be performed individually on each of the single-channel semantic embeddings. Additionally or alternatively, dimensionality reduction may be performed on the concatenated semantic embedding. Further, in some embodiments, additional dimensions could be defined by comparing the single-channel semantic embeddings 712, 722, 732 to one another. Such additional dimensions may be used to analyze information based on inter-channel relationships, thus ensuring that such information is not lost.

The composite scientific image 702 illustrated in FIG. 7A may correspond to one possible visual representation of a subject (e.g., a perturbed subject). Additionally or alternatively, the three channels (the first channel 710, the second channel 720, and the third channel 730) may each, individually, correspond to other types of visual representations of the subject (e.g., each captured by different imaging modalities). In other embodiments, the subject may additionally or alternatively be represented in other types of visual representations.

In some embodiments, a single-channel semantic embedding for a visual representation of a respective subject (e.g., the first semantic embedding 712, the second semantic embedding 722, or the third semantic embedding 732) or a combined semantic embedding for a composite visual representation of a subject (e.g., the unified semantic embedding 740) may be integrated with side data to enhance the respective semantic embedding and improve data analysis performed using the respective semantic embedding. The side data may correspond to one or more supplemental measurements that were performed on the respective subjects. Such side data may be represented in the form of supplemental visual representations. Additionally or alternatively, side data may correspond to additional numerical data to be used in conjunction with the original visual representation. For example, the side data may correspond to information accessible only by supplemental measurements (e.g., information that is not accessible simply by analyzing the visual representation generated of the respective perturbed subject). In various embodiments, the side data may include experimental metadata (e.g., information about how the experiment was performed, in what spatial location the experiment was performed, subject provenance for subjects of the experiment, or preparation history for the experiment), transcriptomic data, genomic data, proteomic data, metabolomic data, lipidomic data, bulk semiconductor material properties, and/or patient diagnostic data. Other types of side data are also possible.

Figure 7B:
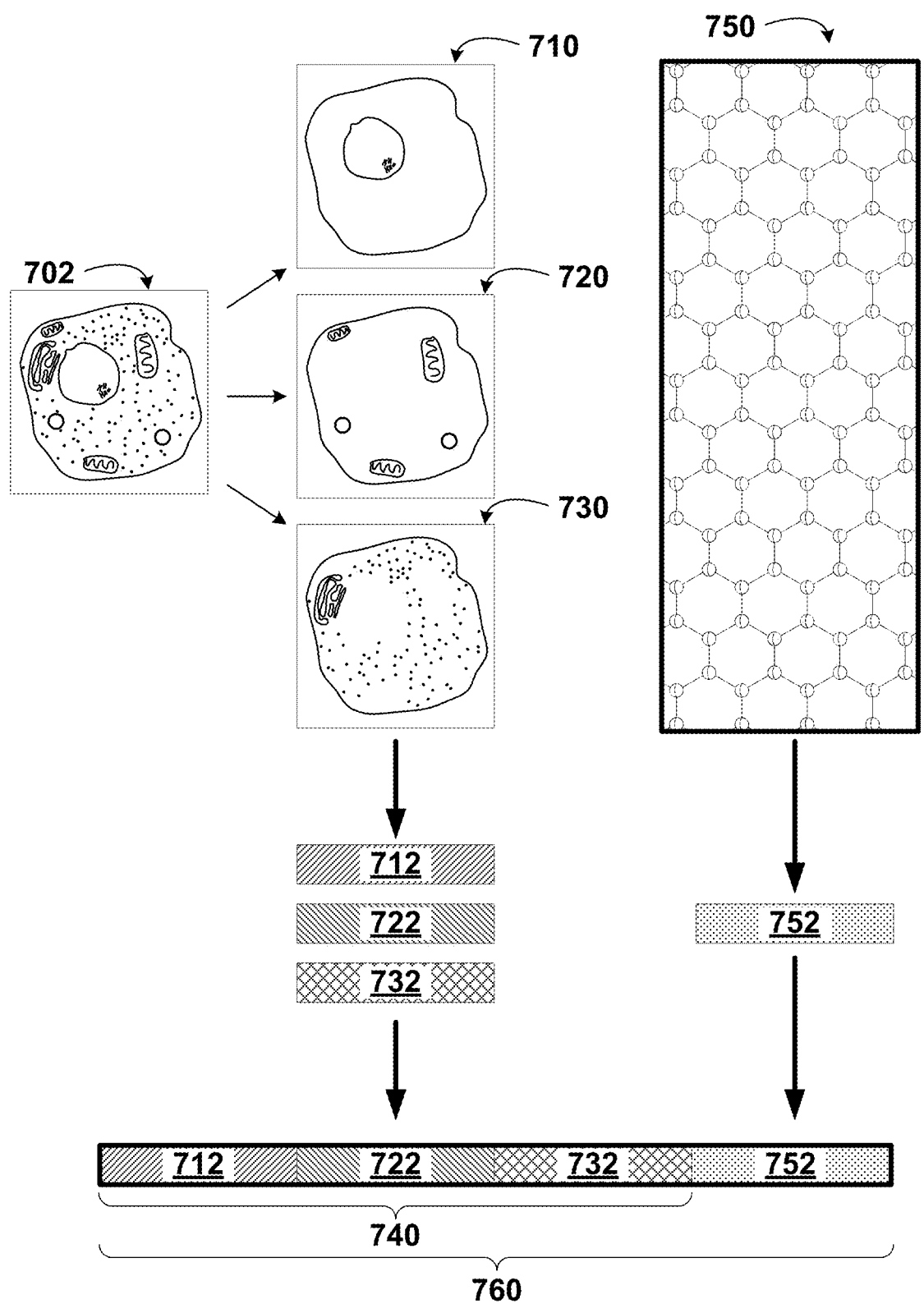
FIG. 7B is an illustration of a process, according to example embodiments.

FIG. 7B is an illustration of a process, according to example embodiments. The process corresponds to an integration of side data with visual representations to arrive at a combined semantic embedding 760. The side data illustrated in FIG. 7B may be metabolomic data 750, for example. The metabolomic data 750 may correspond to metabolites in and/or around the biological cell illustrated in the composite scientific image 702, for example. Further, the metabolomic data 750 may correspond to repeated measurements of metabolites over a period of time and/or a single measurement of metabolites at a single point in time.

As illustrated in FIG. 7B, one technique by which the side data (e.g., the metabolomic data 750) may be integrated with the visual representations includes generating one or more additional single-channel semantic embeddings 752 for the side data (e.g., using the machine-learned, deep metric network model) and then concatenating the additional single-channel sematic embeddings 752 with the single-channel semantic emeddings for each channel of the visual representation. For example, similar to FIG. 7A, the visual representation may include three channels, and, correspondingly, may then have three single-channel semantic embeddings generated (e.g., the first semantic embedding 712, the second semantic embedding 722, and the third semantic embedding 732). Also as illustrated in FIG. 7A, the concatenation of the first semantic embedding 712, the second semantic embedding 722, and the third semantic embedding 732 may correspond to the unified semantic embedding 740. A concatenation of the additional single-channel semantic embedding 752 with the first semantic embedding 712, the second semantic embedding 722, and the third semantic embedding 732 may result in an integrated multi-channel semantic embedding 760, as illustrated. The integrated multi-channel semantic embedding 760 may contain more information than the unified semantic embedding 740, for example, and thereby provide more information about a given subject (e.g., provide more data about similarities and differences among subjects when comparing the integrated multi-channel semantic embeddings 760 for the respective subjects).

Figure 7C:
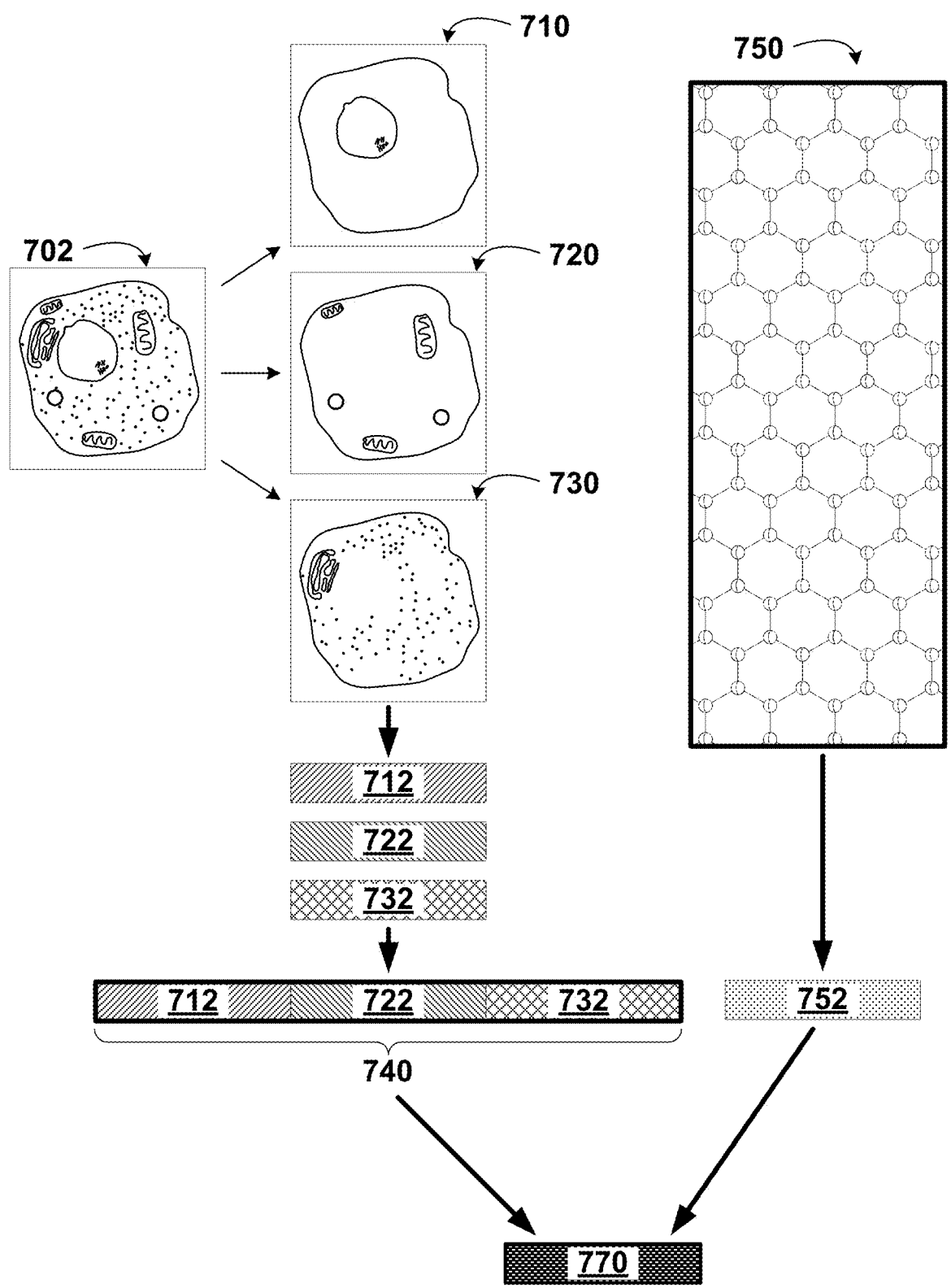
FIG. 7C is an illustration of a process, according to example embodiments.

FIG. 7C is an illustration of a process, according to example embodiments. In some embodiments, as illustrated in FIG. 7C, in addition to or instead of concatenating single-channel semantic embeddings (as in FIG. 7B), integrating the side data (e.g., the metabolomic data 750) with the visual representations of a subject may include producing a hybrid semantic embedding 770.

Similar to FIG. 7B, the process illustrated in FIG. 7C may include generating the additional single-channel semantic embedding 752 (e.g., using the machine-learned, deep metric network model) from the metabolomic data 750. Then, using the first semantic embedding 712, the second semantic embedding 722, and the third semantic embedding 732 (e.g., individually or in the form of the unified semantic embedding 740, as illustrated) in conjunction with the additional single-channel semantic embedding 752, the hybrid semantic embedding 770 may be generated. In other embodiments (e.g., embodiments where the visual representation of the subject only contains a single channel), the hybrid semantic embedding 770 may be generated using the additional single-channel semantic embedding 752 and only one single-channel semantic embedding generated for the visual representation.

In some embodiments, the hybrid semantic embedding 770 may be generated using the machine-learned, deep metric network. In other embodiments, the hybrid semantic embedding 770 may be generated using a different machine-learned model (e.g., an autoencoder or a machine-learned model trained to combine dimensional values from previously generated semantic embeddings). In various embodiments, the hybrid semantic embedding 770 may be single-channel or multi-channel (e.g., but not generated using concatenation).

Figure 7D:
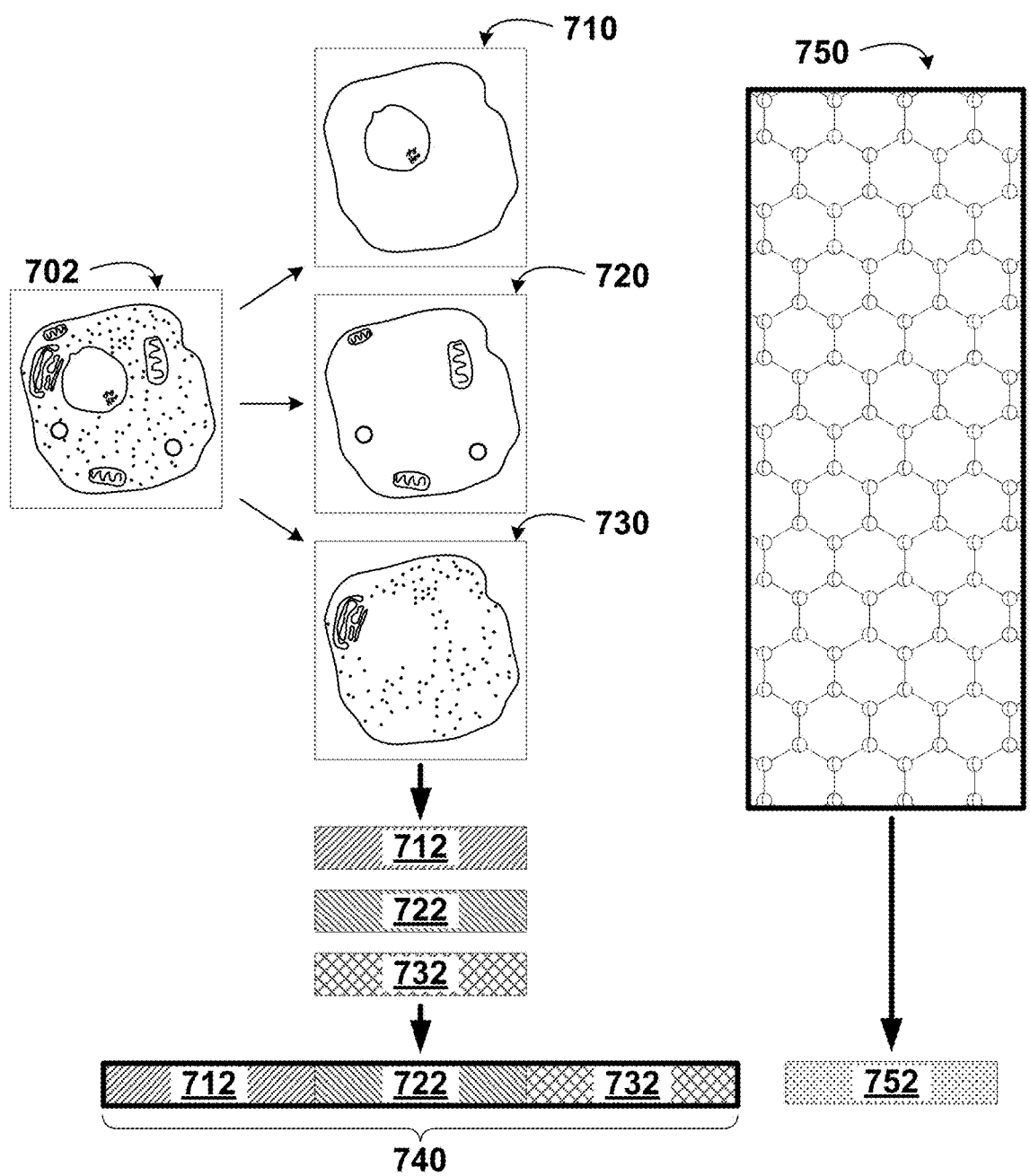
FIG. 7D is an illustration of a process, according to example embodiments.

FIG. 7D is an illustration of a process, according to example embodiments. In some embodiments, as illustrated in FIG. 7D, in addition to or instead of concatenating single-channel semantic embeddings (as in FIG. 7B) or producing a hybrid semantic embedding 770 using a machine-learned model (as in FIG. 7C), integrating the side data (e.g., the metabolomic data 750) with the visual representations of a subject may include producing a composite semantic embedding 780 by applying a mathematical operation to corresponding dimensions of the semantic embeddings generated for the visual representation and the side data.

Similar to FIGS. 7B and 7C, the process illustrated in FIG. 7D may include generating the additional single-channel semantic embedding 752 (e.g., using the machine-learned, deep metric network model) from the metabolomic data 750. Then, by applying one or more mathematical operations to the generated first semantic embedding 712, the second semantic embedding 722, the third semantic embedding 732 (e.g., in the form of the unified semantic embedding 740 or individually, as illustrated), and the additional single-channel semantic embedding 752, the composite semantic embedding 780 may be generated. In other embodiments (e.g., embodiments where the visual representation of the subject only contains a single channel), the composite semantic embedding 780 may be generated using the additional single-channel semantic embedding 752 and only one single-channel semantic embedding generated for the visual representation.

As illustrated, the composite semantic embedding 780 may represent an average of the first semantic embedding 712, the second semantic embedding 722, the third semantic embedding 732, and the additional single-channel semantic embedding 752. For example, the value for a respective dimension within the composite semantic embedding 780 may be an average of the values for that respective dimension from each of the first semantic embedding 712, the second semantic embedding 722, the third semantic embedding 732, and the additional single-channel semantic embedding 752. In other embodiments, other mathematical operations may be used in addition to or instead of averaging. For example, weighted averages, summations, weighted summations, differences, weighted differences, products, weighted products, quotients, weighted quotients, geometric averages, weighted geometric averages, and/or medians may be used to generate the composite semantic embedding 780. Other mathematical operations are also possible.

Figure 8:
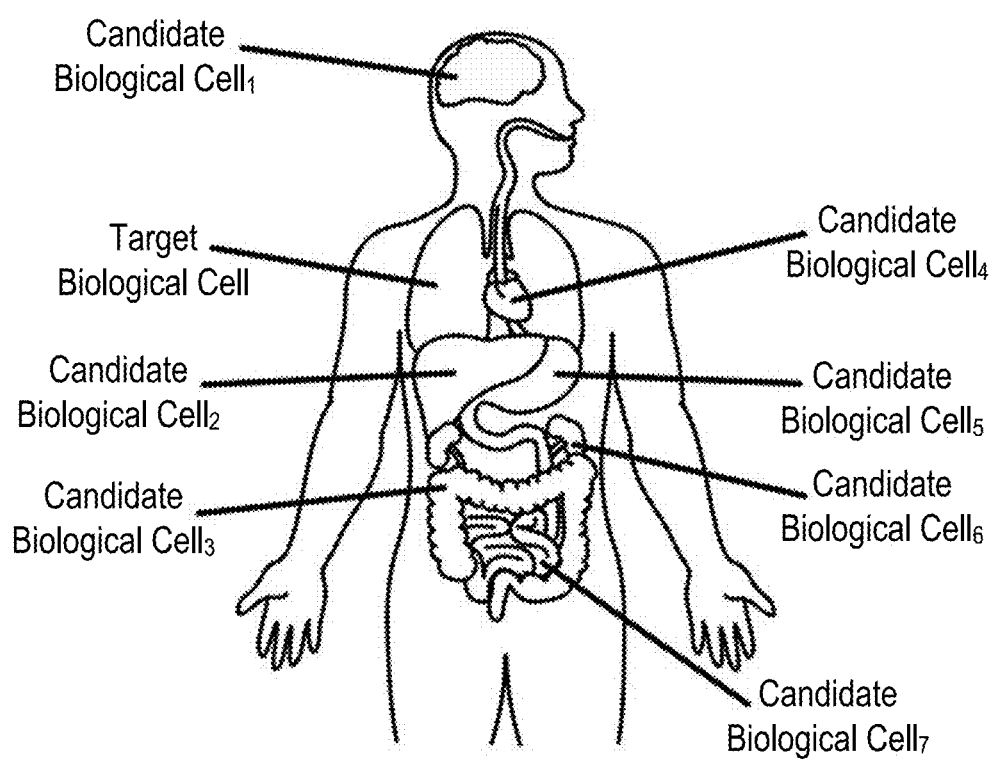
FIG. 8 is an illustration of anatomical regions of a patient from which candidate biological cells and a target biological cell may be acquired, according to example embodiments.

FIG. 8 is an illustration 800 of anatomical regions of a patient from which candidate biological cells and a target biological cell may be acquired, according to example embodiments. For example, in some embodiments, it may be known that a patient has a disease in one location of their body (e.g., lung cancer). During a biopsy, a sample of cells from the anatomical region with the known disease may be acquired. These cells may thus be indicated to have an unhealthy phenotype and may be indicated to be target biological cells. Also during the biopsy, samples of cells may be acquired from other anatomical regions of the body. For example, samples may also be acquired from the brain, the liver, the large intestine, the heart, the stomach, the kidneys, and the small intestine. Samples may also be taken from other anatomical regions of the body in various embodiments (e.g., the skin to study fibroblasts or the blood to study leukocytes). These additional samples may be labelled as candidate biological cells having candidate phenotypes.

Upon retrieving the target biological cells and the candidate biological cells, a target image and several candidate images may then be recorded. The images may then be compared by a computing device using a machine-learned, deep metric network, in some embodiments. If any of the candidate images have a similarity score with the target image that is above a threshold similarity score, for example, those candidate images may then be determined to correspond to candidate biological cells that have a similar phenotype to the target phenotype (an unhealthy phenotype, for example). This may indicate, as in the example of lung cancer, that the cancer has metastasized to another anatomical region of the patient (e.g., the anatomical region from which the candidate biological cells having a similar phenotype to the target phenotype were acquired). The converse is also possible, in alternate embodiments. For example, an anatomical region of the patient may include target cells that are known to have a healthy phenotype, and a diagnostic may be run (e.g., using a computing device that uses a machine-learned, deep metric network to perform image comparisons) to evaluate whether candidate cells from other anatomical regions also have healthy phenotypes (e.g., if the candidate cells have a similarity score with the target cells that is greater than a threshold similarity score).

In still other embodiments, target cells within certain anatomical regions of the body may be known to exhibit certain mechanisms of action or respond to certain stimuli in certain ways, based on their phenotype. Again, candidate cells in other anatomical regions of the body could be compared and contrasted with the target cells, to establish if their phenotypes are similar to the target phenotype of the target cells.

Figure 9:
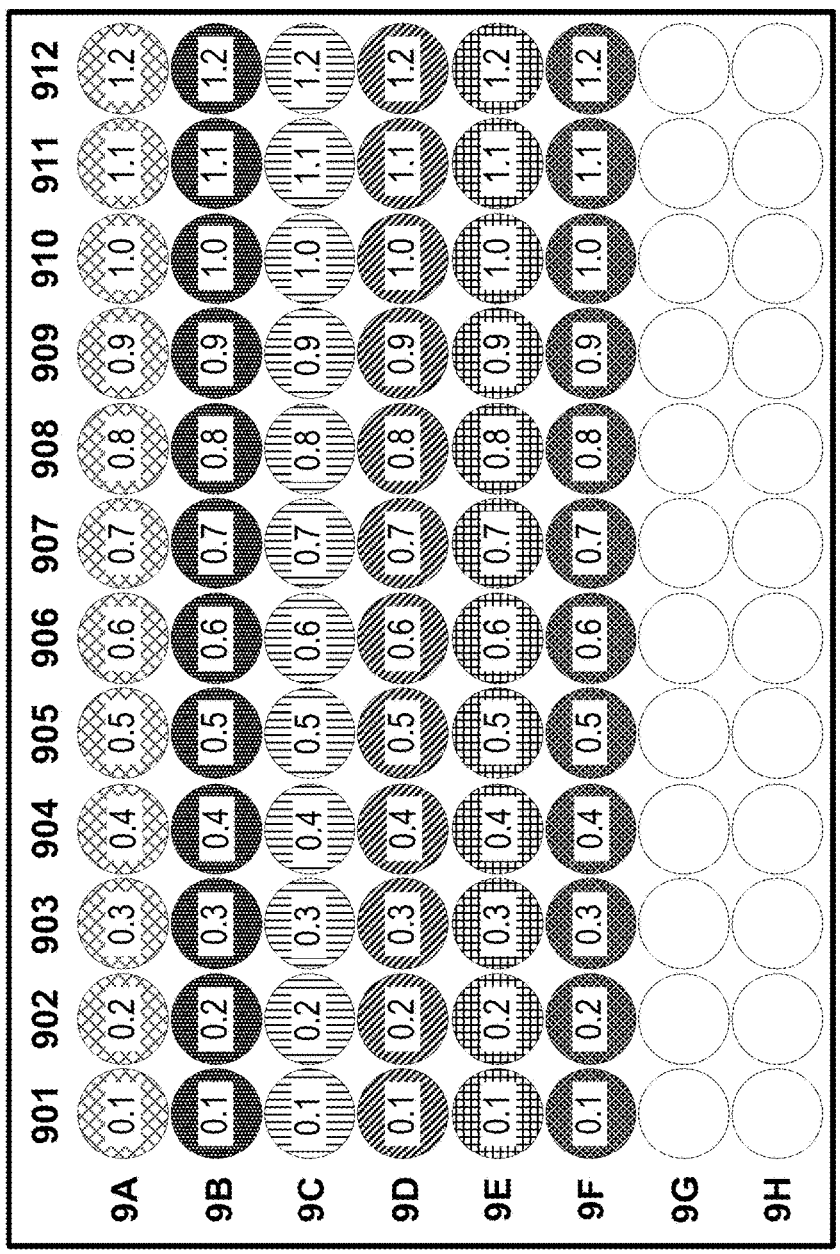
FIG. 9 is an illustration of a multi-well sample plate, according to example embodiments.

FIG. 9 is an illustration of a multi-well sample plate 900, according to example embodiments. The multi-well sample plate 900 may include various numbers of rows and columns, in various embodiments. As illustrated in FIG. 9, the multi-well sample plate 900 includes eight rows (row 9A, row 9B, row 9C, row 9D, row 9E, row 9F, row 9G, and row 9H) and twelve columns (column 901, column 902, column 903, column 904, column 905, column 906, column 907, column 908, column 909, column 910, column 911, and column 912). Other numbers of rows and/or columns may be used in alternate embodiments. The multi-well sample plate 900 may be loaded with various samples in various wells in order to generate data analyzable using a computing device that uses a machine-learned, deep metric network model, for example.

In one embodiment, one subset of the wells of the multi-well sample plate 900 (e.g., row 9G) may be loaded with biological cells from a negative control group. This group of cells may be equivalent to a group of candidate biological cells initially, but may not receive any treatment. Another subset of the wells of the multi-well sample plate 900 (e.g., row 9H) may be loaded with target biological cells having a known target phenotype (e.g., a healthy phenotype). The remaining rows of wells of the multi-well sample plate 900 may be loaded with candidate biological cells.

The candidate biological cells may be known to initially have a given phenotype (e.g., an unhealthy phenotype). Thereafter, the candidate biological cells may be treated with various candidate treatment compounds at various concentrations. For example, all candidate biological cells in row 9A may be treated with candidate treated compound one, all candidate biological cells in row 9B may be treated with candidate treatment compound two, all candidate biological cells in row 9C may be treated with candidate treatment compound three, and so on. In addition, all candidate biological cells in column 901 (excluding the negative control biological cells and target biological cells in column 901, row 9G and column 901, row 9H, respectively) may be treated with the respective candidate treatment compound of their row at a concentration of 0.1 molar. Similarly, all candidate biological cells in column 902 may be treated with the respective candidate treatment compound of their row at a concentration of 0.2 molar, and so on for the rest of the columns through 1.2 molar.

As an example, row 9C may be treated with candidate treatment compound three in concentrations of 0.1 molar in column 901, 0.2 molar in column 902, 0.3 molar in column 903, 0.4 molar in column 904, 0.5 molar in column 905, 0.6 molar in column 906, 0.7 molar in column 907, 0.8 molar in column 908, 0.9 molar in column 909, 1.0 molar in column 910, 1.1 molar in column 911, and 1.2 molar in column 912. As an additional example, column 905 may be treated with concentrations of 0.5 molar using candidate treatment compound one in row 9A, candidate treatment compound two in row 9B, candidate treatment compound three in row 9C, candidate treatment compound four in row 9D, candidate treatment compound five in row 9E, and candidate treatment compound six in row 9F.

In other embodiments (e.g., embodiments where the subjects are not biological cells), multi-well sample plates may not be used. Further, a different perturbation (e.g., a perturbation other than applying a candidate treatment compound) may be applied to the subjects in other embodiments. For example, applying a perturbation may include selectively mixing two or more metal salts (e.g., Iron, Mn, and Mg) using predefined ratios and then heating the metal salts to allow them to oxidize. Visual representations of the oxidized, mixed metal salts may then be generated using one or more imaging modalities. For example, colors (e.g., imaged using different wavelengths, either within the visible spectrum or outside of the visual spectrum) within the visual representation and/or textures within the visual representation may correspond to what the chemical composition of the perturbed subject is. Thereafter, the visual representations of the oxidized, mixed metal salts may be used to generate semantic embeddings and then the semantic embeddings may be compared/analyzed to determine specific characteristics of the oxides (e.g., to back out chemical compositions of the oxides and/or to identify desired characteristics of one or more oxides, thereby identifying desired ratios of the two or more metal salts). In embodiments using other types of perturbations, other material properties may additionally or alternatively be analyzed using semantic embeddings generated for visual representations of materials (e.g., wetting properties, electrical surface properties, optical surface properties, coefficients of friction, hardness, ductility, elasticity, viscosity, porosity, tensile strength, compressive strength, packing fraction, capacitance, inductance, dielectric constant, relative magnetic permeability, absorbance, reflectivity, transmittance, coefficient of thermal expansion, melting point, boiling point, flammability, emissivity, flash point, specific heat, thermal conductivity, etc. may be analyzed).

In various embodiments (e.g., depending on the subjects to be perturbed), applying a perturbation to a plurality of subjects may include adding one or more small molecule compounds to at least one of the plurality of subjects; applying a genetic modification to at least one of the plurality of subjects; allowing a predetermined amount of time to elapse for at least one of the plurality of subjects; illuminating at least one of the plurality of subjects with light of a predetermined wavelength; heating or cooling at least one of the plurality of subjects to a predetermined temperature; exposing at least one of the plurality of subjects to another subject of the plurality of subjects; introducing at least one of the plurality of subjects to a different environment; and/or applying a predetermined force to one or more regions of at least one of the plurality of subjects. In other embodiments, applying a perturbation to a subject may include alternate perturbations or a combination of the above-described perturbations.

Negative control images of the negative control group biological cells, target images of the target biological cells, and candidate images of the candidate biological cells may then be recorded of the biological cells from the different wells of the multi-well sample plate 900. The negative control images, the candidate images, and the target images may then be compared to one another (e.g., by a computing device using a machine-learned, deep metric network model).

In other embodiments, other delineations may be drawn between samples within different wells of the multi-well sample plate 900. For example, in some embodiments, negative control group samples, candidate samples, or target samples may correspond to various healthy phenotype(s), various unhealthy phenotype(s), various candidate compounds, various candidate compound concentrations, various candidate treatment durations, various anatomical regions of a single patient, a common anatomical region across various patients, various anatomical regions across various patients, various mechanisms of action (e.g., analyzed by providing specific wells of the multi-well sample plate 900 with various inhibitors), and/or various compounds for illuminating specific cellular regions (e.g., fluorescent compounds, chemical dyes, or chemiluminescent compounds). Other candidate variations for similarity study among various cells are also possible.

For example, in alternate embodiments, one subset of the wells of the multi-well sample plate 900 (e.g., row 9G) may be loaded with biological cells from a negative control group. This group of cells may be equivalent to a group of candidate biological cells initially, but may not receive any treatment and/or genetic modifications (e.g., targeted mutations). Another subset of the wells of the multi-well sample plate 900 (e.g., row 9H) may be loaded with a first set of candidate biological cells (e.g., somatic cells, fibroblasts, or induced pluripotent stem cells) having a known genetic mutation (e.g., a genetic mutation whose presence prevents the occurrence of a disease, such as by coding for the production of a particular protein; whose presence increases or decreases cellular and organismal growth rate; whose presence leads to a disorder or disease; etc.). Such a genetic mutation may be naturally occurring or may be the result of targeted genetic modifications (e.g., using a clustered regularly interspaced short palindromic repeats (CRISPR) screen), in various embodiments. The remaining rows of wells of the multi-well sample plate 900 may be loaded with a second set of candidate biological cells (e.g., somatic cells, fibroblasts, or induced pluripotent stem cells).

The first set of candidate biological cells and the second set of candidate biological cells may be known to initially have a given phenotype (e.g., a healthy phenotype). Thereafter, the second set of candidate biological cells may be given various candidate treatment compounds at various concentrations. For example, all of the second set of candidate biological cells in row 9A may be treated with candidate treated compound one, all of the second set of candidate biological cells in row 9B may be treated with candidate treatment compound two, all of the second set of candidate biological cells in row 9C may be treated with candidate treatment compound three, and so on. In addition, all of the second set of candidate biological cells in column 901 (excluding the negative control biological cells and target biological cells in column 901, row 9G and column 901, row 9H, respectively) may be treated with the respective candidate treatment compound of their row at a concentration of 0.1 molar. Similarly, all of the second set of candidate biological cells in column 902 may be treated with the respective candidate treatment compound of their row at a concentration of 0.2 molar, and so on for the rest of the columns through 1.2 molar.

As an example, row 9C may be treated with candidate treatment compound three in concentrations of 0.1 molar in column 901, 0.2 molar in column 902, 0.3 molar in column 903, 0.4 molar in column 904, 0.5 molar in column 905, 0.6 molar in column 906, 0.7 molar in column 907, 0.8 molar in column 908, 0.9 molar in column 909, 1.0 molar in column 910, 1.1 molar in column 911, and 1.2 molar in column 912. As an additional example, column 905 may be treated with concentrations of 0.5 molar using candidate treatment compound one in row 9A, candidate treatment compound two in row 9B, candidate treatment compound three in row 9C, candidate treatment compound four in row 9D, candidate treatment compound five in row 9E, and candidate treatment compound six in row 9F.

After treating the second set of candidate biological cells, a time-evolution of the first set of candidate biological cells and the second set of candidate biological cells may be monitored. In some embodiments, prior to the time-evolution being monitored, a parasite, bacterium, virus, etc. may be introduced to each of the wells having the first set of candidate biological cells and/or the second set of biological cells (e.g., to test for a resistance to the parasite, bacterium, virus, etc.). Further, in some embodiments, the first set and/or the second set of candidate biological cells may be infected with one or more diseases (e.g., Parkinson's disease, amyotrophic lateral sclerosis, or Alzheimer's disease). In such embodiments, the negative control biological cells may also be infected with the disease.

Negative control images of the negative control group biological cells and candidate images of the candidate biological cells may then be recorded of the biological cells from the different wells of the multi-well sample plate 900. The negative control images and the candidate images may then be compared to one another (e.g., by a computing device using a machine-learned, deep metric network model). Comparing the candidate images of the first set of candidate biological cells to the candidate images of the second set of candidate biological cells (e.g., using a machine-learned, deep metric network model) may allow for an identification of which, if any, of the candidate treatment compounds mirrors or mimics the results of the genetic mutations (e.g., after introduction of the parasite, bacterium, virus, or disease). Such an identification of one or more candidate treatment compounds that mimics one or more of the genetic modifications may be based on vector distances in a multi-dimensional space described by semantic embeddings between candidate images (e.g., between a candidate image recorded of the first set of candidate biological cells and a candidate image recorded of the second set of candidate biological cells).

As described above with reference to FIG. 3G, identifying molecular mimetics of genetic perturbations (e.g., mutations) may include identifying a plurality of phenotypic strata (e.g., phenotypic strata representing various subpopulations). Then, based on the phenotypic strata, one or more gradients may be determined (e.g., gradients between strata). One or more of these gradients may represent certain genetic perturbations. Additionally or alternatively, one or more of these gradients may represent an applied candidate treatment compound (e.g., in a given concentration). If there is a threshold level of similarity (e.g., in slope or intercept) between one of the gradients corresponding to a genetic perturbation and one of the gradients corresponding to an applied candidate treatment compound, a computing device (e.g., using a machine-learned, deep-metric network) may determine that the respective applied candidate treatment compound mimics the genetic perturbation. Identifying such a mimicking could later be used for diagnosing and/or treating patients. For example, such an identification may be used in the development of a therapeutic drug that mimics a genetic modification.

Alternatively, in some embodiments, it may be determined (e.g., based on semantic embeddings) that a given genetic mutation corresponds to a given rate of change (e.g., per unit time) in a first dimension of a semantic embedding. If it is determined that a given candidate treatment compound corresponds to a given rate of change (e.g., per unit time) in a first dimension of a semantic embedding that is of threshold similarity to the given rate of change corresponding to the genetic mutation, a computing device (e.g., using a machine-learned, deep-metric network) may determine that the respective candidate treatment compound mimics the genetic perturbation. In such embodiments, both the genetic perturbation and the application of the respective candidate treatment compound may move a biological cell along the first dimension. In other embodiments, the genetic perturbations and/or the candidate treatment compounds may correspond to a superposition of rates of change (e.g., per unit time) in multiple dimensions of a semantic embedding.

Figure 10:
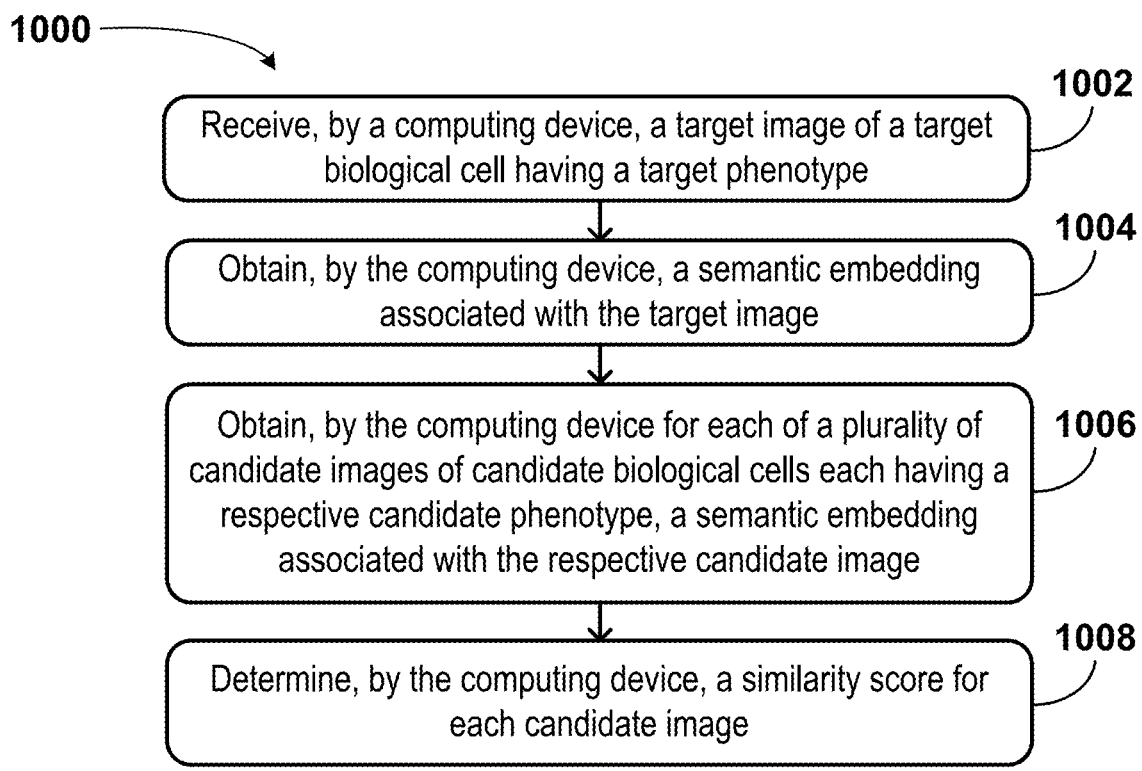
FIG. 10 is an illustration of a method, according to example embodiments.

FIG. 10 is an illustration of a method 1000, according to example embodiments. In some embodiments, each block may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and compact-disc read-only memory (CD-ROM), for example. In addition, one or more blocks in FIG. 10 may represent circuitry that is wired to perform the specific logical operations.

In some embodiments, the method 1000 may include additional blocks occurring before, in between, or after the blocks illustrated in FIG. 10. Further, in some embodiments, one or more of the blocks illustrated in FIG. 10 may be repeated one or more times. In alternate embodiments, the order of various blocks within the method may be rearranged without departing from the scope of the method.

At block 1002, the method 1000 includes receiving, by a computing device, a target image of a target biological cell having a target phenotype. The target image may include image data (e.g., the pixel values used to generate the image) and/or a reference value associated with a location of an associated semantic embedding (e.g., a memory address associated with the associated semantic embedding). The target image may have been recorded by a camera, for example. Further, in some embodiments, the camera may have one or more associated optical filters configured to allow the transmission of only a range of wavelengths to the camera. Additionally, the camera may transmit the target image to the computing device. For example, the camera may communicate with the computing device over WiFi (IEEE 802.11 standards), over Bluetooth®, or via wireline interface (e.g., a universal serial bus, USB, cable).

In alternate embodiments, the computing device may receive the target image through communication with another computing device. For example, the computing device may receive the target image from a mobile computing device (e.g., a mobile phone equipped with a camera that recorded the target image), a tablet computing device, or a personal computing device (e.g., a laptop computing device). The computing device may receive the target image via an application (app) or through electronic mail (email), in various embodiments.

In some embodiments, the target image received by the computing device may be accompanied by target image metadata. For example, the target image metadata may include when the target image was recorded, the number of channels in the target image, the bit-depth of each channel in the target image, to which wavelength ranges or cellular components each channel in the target image corresponds, a predetermined target phenotype associated with the target cells in the target image, a treatment regimen provided to the target cells in the target image, the mechanisms of action occurring in the target cells of the target image, a row of a multi-well sample plate from which the target image was recorded, a column of a multi-well sample plate from which the target image was recorded, or an anatomical region of a patient from which the target cells in the target image were acquired.

At block 1004, the method 1000 includes obtaining, by the computing device, a semantic embedding associated with the target image. The semantic embedding associated with the target image may be generated using a machine-learned, deep metric network model. The machine-learned, deep metric network model may have been previously trained using consumer photographic training data. For example, the consumer photographic training data may include three-image sets (e.g., similar to the three-image set illustrated in FIG. 1). The three-image sets may be based upon internet search results and selections (e.g., by internet users). The internet search results and selections may allow the computing device to train the machine-learned, deep metric network model to identify similarities and differences between images. In some embodiments, particular features of images will be separated into dimensions (e.g., 64 dimensions) of the semantic embedding during the training of the machine-learned, deep metric network.

Further, in some embodiments, obtaining the semantic embedding associated with the target image may include a similar process to the process illustrated in FIG. 7A. For example, obtaining the semantic embedding associated with the target image may include retrieving the channels of the target image, obtaining a semantic embedding for each channel of the target image, and concatenating each channel of the target image into a single semantic embedding. In some embodiments, each of the channels may correspond to a predetermined range of wavelengths detectable by one or more cameras (e.g., to investigate one or more regions of the target biological cell). The concatenated semantic embedding may have more dimensions than the single-channel semantic embeddings (e.g., 192 dimensions for a concatenated semantic embedding of a target image having three channels, each channel having a 64 dimension single-channel semantic embedding).

In alternate embodiments, alternate processes of obtaining a semantic embedding associated with the target image may additionally or alternatively be used. For example, an autoencoder may generate a semantic embedding associated with the target image. In other embodiments, a classification model other than the machine-learned, deep metric network model may be used to obtain the semantic embedding. For example, an output or a hidden layer of another artificial neural network may generate the semantic embedding for the target image. In still other embodiments, variations of the machine-learned, deep metric network model trained on three-image sets may be used to obtain the semantic embedding of the target image. For example, the machine-learned, deep metric network model may be trained with images that more closely resemble the target image and the candidate images (e.g., the model is not trained on consumer photographic query results), such as only scientific images or only images of biological cells.

At block 1006, the method 1000 includes obtaining, by the computing device for each of a plurality of candidate images of candidate biological cells (e.g., each corresponding to a candidate mechanism of action) each having a respective candidate phenotype, a semantic embedding associated with the respective candidate image. The candidate images may include image data (e.g., the pixel values used to generate the image) and/or a reference value associated with a location of an associated semantic embedding (e.g., a memory address associated with the associated semantic embedding). Analogous to block 1002, the candidate images may have been recorded by a camera. Likewise, in some embodiments, the camera may have one or more associated optical filters configured to allow the transmission of only a range of wavelengths to the camera. Additionally, the camera may transmit the candidate images to the computing device. For example, the camera may communicate with the computing device over WiFi, over Bluetooth®, or via wireline interface (e.g., a USB cable).

In alternate embodiments, the computing device may receive the candidate images through communication with another computing device. For example, the computing device may receive the candidate images from a mobile computing device (e.g., a mobile phone equipped with a camera that recorded the candidate image), a tablet computing device, or a personal computing device (e.g., a laptop computing device). The computing device may receive the candidate images via an app or through email, in various embodiments.

In some embodiments, the candidate images received by the computing device may be accompanied by candidate image metadata. For example, the candidate image metadata may include when the candidate images were recorded, the number of channels in the candidate images, the bit-depth of each channel in the candidate images, to which wavelength ranges or cellular components each channel in the candidate images corresponds, treatment regimens provided to the candidate cells in the candidate images, the mechanisms of action occurring in the candidate cells of the candidate images, a row of a multi-well sample plate from which the candidate images were recorded, a column of a multi-well sample plate from which the candidate images were recorded, or an anatomical region of a patient from which the candidate cells in the candidate images were acquired.

Similar to block 1004, the semantic embeddings associated with the candidate images may be generated using a machine-learned, deep metric network model. The machine-learned, deep metric network model may be the same model as in block 1004 (i.e., may have been previously trained using consumer photographic training data). Also similar to block 1004, in some embodiments, obtaining the semantic embeddings associated with the candidate images may include a similar process to the process illustrated in FIG. 7A. Also similar to block 1004, alternate processes of obtaining the semantic embeddings associated with the respective candidate images may be used (e.g., semantic embeddings generated by an autoencoder or semantic embeddings obtained using a variation on the machine-learned, deep metric network model).

At block 1008, the method 1000 includes determining, by the computing device, a similarity score for each candidate image. Determining the similarity score for a respective candidate image includes computing, by the computing device, a vector distance in a multi-dimensional space described by the semantic embeddings between the respective candidate image and the target image. The similarity score for each candidate image represents a degree of similarity between the target phenotype and the respective candidate phenotype.

In some embodiments, the method 1000 may also include training the machine-learned, deep metric network model. Training the machine-learned, deep metric network model may include receiving, by the computing device, a series of three-image sets as training data. Each three-image set may include a query image, a positive image, and a negative image. The query image, the positive image, and the negative image may be photographic internet search results ranked in comparison with another based on selections by internet users, for example. In addition, based on the selections by internet users, it is determined (e.g., by the computing device) that a similarity between the query image and the positive image is greater than a similarity between the query image and the negative image. The method 1000 may additionally include refining, by the computing device, the machine-learned, deep metric network model based on each three-image set to account for image components of the query image, the positive image, and/or the negative image.

Further, in some embodiments, the method 1000 may include receiving, by the computing device, a plurality of control group images of control group biological cells having control group phenotypes. In such embodiments, the method 1000 may also include obtaining, by the computing device for each control group image, a semantic embedding associated with the respective control group image. Further, in such embodiments, the method 1000 may also include normalizing, by the computing device, the semantic embeddings associated with the candidate images. Normalizing may include computing, by the computing device, eigenvalues and eigenvectors of a covariance matrix defined by the values of each dimension of the semantic embeddings associated with the control group images using principal component analysis. Normalizing may also include scaling, by the computing device, values of each dimension of the semantic embeddings associated with the control group images by a respective dimensional scaling factor such that each dimension is zero-centered and has unit variance. Further, normalization may include scaling, by the computing device, values of each corresponding dimension of the semantic embeddings associated with the candidate images by the respective dimensional scaling factor. Such normalization of the semantic embeddings associated with the candidate images may negate an influence of common morphological variations (e.g., variations in cellular size, in nuclear size, in cellular shape, in nuclear shape, in nuclear color, in nuclear size relative to cellular size, or in nuclear location within a respective cell) among the candidate biological cells on the similarity scores. In some embodiments, normalizing may further include shifting, by the computing device, values of each corresponding dimension of the semantic embeddings associated with the candidate images by a dimensional shifting factor.

Even further, in some embodiments, the method 1000 may include additional analysis of the similarity scores. As described with respect to FIGS. 4C and 4F, the similarity scores may be ranked to determine which candidate image has the greatest similarity score (i.e., the maximum similarity score) among the candidate images. The candidate image with the greatest similarity score may be determined to be most similar to the target image. Thus, the candidate image with the greatest similarity score may be determined to correspond to a candidate biological cell that has a candidate phenotype that is most similar to the target phenotype of the target biological cell associated with the target image. In some embodiments (e.g., where the target phenotype is a healthy phenotype), the method 1000 may also include determining, by the computing device, a treatment regimen for a patient based on the candidate biological cell having the candidate phenotype that is most similar to the target phenotype. The treatment regimen determined may be a treatment regimen applied to the candidate biological cell corresponding to the greatest similarity score, for example.

Additionally or alternatively, the similarity scores may be compared to a single threshold similarity score to determine which of the corresponding candidate images exhibits a threshold level of similarity with the target image (e.g., those similarity scores that are greater than or equal to the threshold similarity score exhibit the threshold level of similarity with the target image). In still other embodiments, the similarity scores may be grouped into multiple groups of candidate images based on multiple threshold similarity scores (e.g., defined such that each group of candidate images has the same number of candidate images in the group or defined such that certain sets of similarity characteristics between the candidate images and the target image are minimally shared by all members of a group). The candidate images may additionally be group in other ways based on their semantic embeddings that do not include the calculation of a similarity score with the target image. For example, all candidate images having a value of dimension $Z_1$ that is greater than $\varepsilon$ may be put into a group. In this way, candidate images having a given characteristic may be placed into a common group, even if those candidate images do not have comparable similarity scores with one another.

In alternate embodiments, the method 1000 may also include scaling, by the computing device, the target image and each of the candidate images such that an image size of the target image and image sizes of each of the candidate images match an image size (e.g., a standardized size) interpretable using the machine-learned, deep metric network model. Scaling the target image and each of the candidate images may include determining, by the computing device, a location of a cellular nucleus within the respective image. Scaling the target image may also include cropping, by the computing device, the respective image based on a rectangular box centered on the cellular nucleus.

Figure 11:
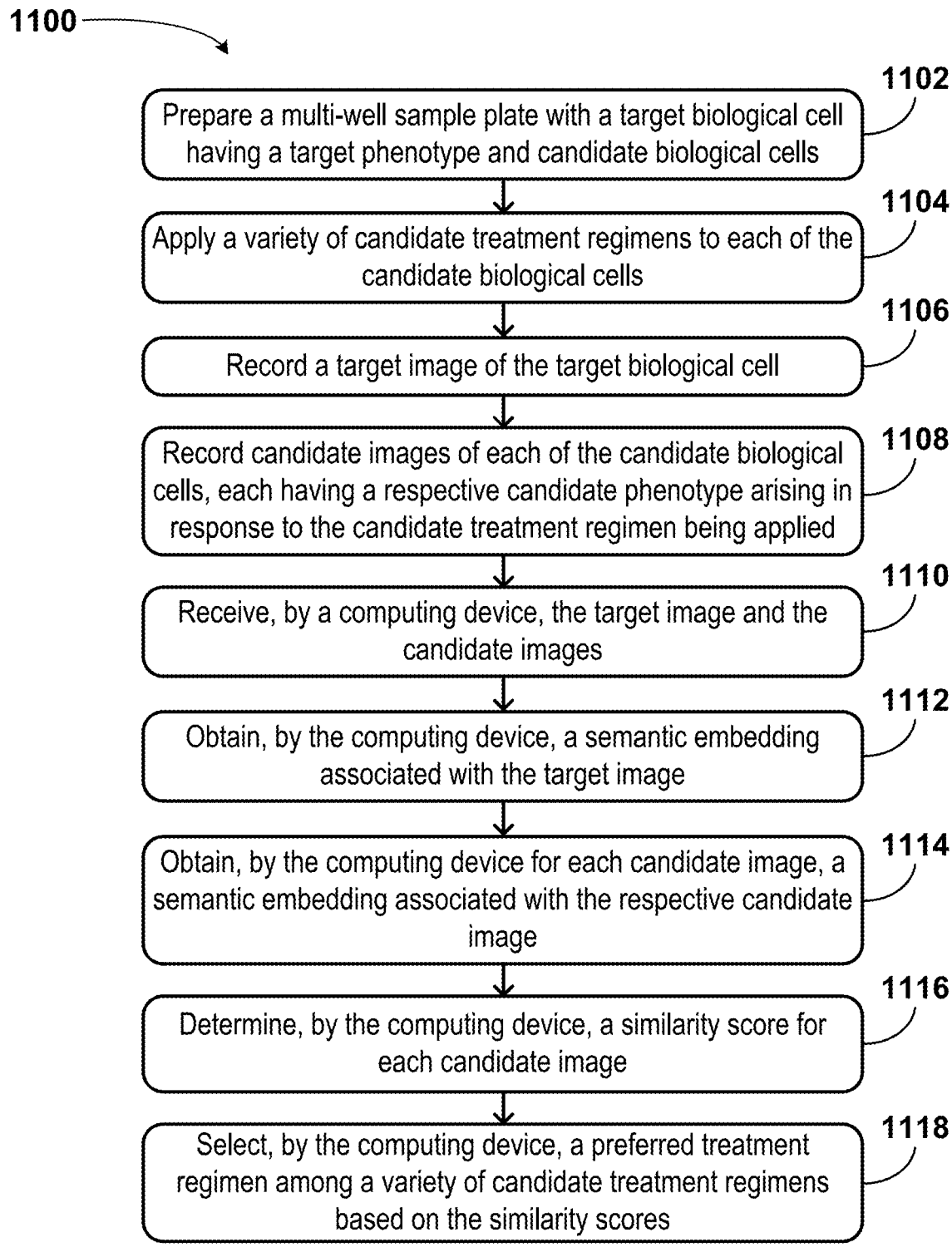
FIG. 11 is an illustration of a method, according to example embodiments.

FIG. 11 is an illustration of a method 1100, according to example embodiments. In some embodiments, various blocks may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and CD-ROM, for example. In addition, one or more blocks in FIG. 11 may represent circuitry that is wired to perform the specific logical operations.

In some embodiments, the method 1100 may include additional blocks occurring before, in between, or after the blocks illustrated in FIG. 11. Further, in some embodiments, one or more of the blocks illustrated in FIG. 11 may be repeated one or more times. In alternate embodiments, the order of various blocks within the method may be rearranged without departing from the scope of the method.

At block 1102, the method 1100 includes preparing a multi-well sample plate with a target biological cell having a target phenotype (e.g., a healthy phenotype) and candidate biological cells. Preparing the multi-well sample plate may include loading specific numbers, concentrations, or volume of target biological cells and/or candidate biological cells into wells of the multi-well sample plate. This may include apportioning aliquots of a target sample and/or of a candidate sample into wells of the multi-well sample plate. Further, preparing the multi-well sample plate may include loading the target biological cell(s) and the candidate biological cell(s) into specified wells of the multi-well sample plate. For example, the target biological cell(s) may be loaded into all wells occupying a first column of the multi-well sample plate. Additionally, the candidate biological cell(s) may be loaded into all wells occupying the remaining columns of the multi-well sample plate. Other loading schemata are also possible in various embodiments.

The multi-well sample plate may be a microtiter plate, in some example embodiments. The multi-well sample plate may also have a variety of numbers of wells in various embodiments. For example, the multi-well sample plate may have 8, 16, 24, 64, 96, 384, or 1536 wells, in various embodiments. Other numbers of wells are also possible. In some embodiments, other containers may be used to hold the samples (e.g., the target biological cells and/or the candidate biological cells). For example, in some embodiments, the samples may be held in centrifuge tubes, beakers, test tubes, petri dishes, vials, flasks, graduated cylinders, burets, and/or microscope slides. Alternative sample containers are also possible in various embodiments.

At block 1104, the method 1100 includes applying a variety of candidate treatment regimens to each of the candidate biological cells. Applying the candidate treatment regimens may include applying any superposition of various candidate treatment compounds, various candidate treatment concentrations, various candidate treatment durations, or various candidate treatment conditions (e.g., temperatures) to various candidate biological cells. In some embodiments, the various candidate treatment regimens may be separated by location on the multi-well sample plate. For example, candidate biological cells in a first row on a multi-well sample plate may be treated with a first candidate treatment compound and candidate biological cells in a second row on the multi-well sample plate may be treated with a second candidate treatment compound. Other alternative treatment arrangements, such as those described with respect to FIG. 9, are also possible.

At block 1106, the method 1100 includes recording a target image of the target biological cell. Recording the target image may include using a camera or a CCD to record an image of a well, or wells, of the multi-well sample plate containing target biological cells. Further, in some embodiments, the camera may have one or more associated optical filters configured to allow the transmission of only a range of wavelengths to the camera. In some embodiments, recording the target image may include storing the target image within a memory (e.g., a non-volatile memory, such as an external hard drive or a secure digital, SD, card).

At block 1108, the method 1100 includes recording candidate images of each of the candidate biological cells, each having a respective candidate phenotype arising in response to the candidate treatment regimen being applied. One or more of the candidate phenotypes may be different from a phenotype exhibited by the respective candidate biological cell prior to treatment. For example, a candidate biological cell may have initially exhibited an unhealthy phenotype, but after treatment using a candidate treatment regimen has a candidate phenotype closer to a healthy phenotype.

Similar to block 1106, recording the images of each of the candidate biological cells may include using a camera or a CCD to record an image of a well, or wells, of the multi-well sample plate containing candidate biological cells. Further, in some embodiments, the camera may have one or more associated optical filters configured to allow the transmission of only a range of wavelengths to the camera. Also, recording the candidate image may include storing the candidate image within a memory.

At block 1110, the method 1100 includes receiving, by the computing device, the target image and the candidate images. The target image or the candidate images may be transmitted directly from a camera to the computing device, in some embodiments (e.g., over WiFi, over Bluetooth®, or via a USB cable).

In alternate embodiments, the computing device may receive the target image and/or the candidate images through communication with another computing device. For example, the computing device may receive the target image and/or the candidate images from a mobile computing device (e.g., a mobile phone equipped with a camera that recorded the target image or the candidate images), a tablet computing device, or a personal computing device (e.g., a laptop computing device). The images may be received by the computing device via transmission using the public Internet, in some embodiments. The computing device may receive the target image or the candidate images via an app or through email, in various embodiments.

In some embodiments, one or more of the images received by the computing device may be accompanied by image metadata. For example, image metadata may include when the image was recorded, the number of channels in the image, the bit-depth of each channel in the image, to which wavelength ranges or cellular components each channel in the image corresponds, a predetermined phenotype associated with the cells in the image, a treatment regimen provided to the cells in the target image, the mechanisms of action occurring in the cells of the target image, a row of a multi-well sample plate from which the image was recorded, a column of a multi-well sample plate from which the image was recorded, or an anatomical region of a patient from which the cells in the image were acquired.

At block 1112, the method 1100 includes obtaining, by the computing device, a semantic embedding associated with the target image. Likewise, at block 1114, the method 1100 includes obtaining, by the computing device for each candidate image, a semantic embedding associated with the respective candidate image. The semantic embeddings associated with the target image or a respective candidate image may be generated using a machine-learned, deep metric network model. The machine-learned, deep metric network model may have been previously trained using consumer photographic training data. For example, the consumer photographic training data may include three-image sets (e.g., similar to the three-image set illustrated in FIG. 1). The three-image sets may be based upon internet search results and selections (e.g., by internet users). The internet search results and selections may allow the computing device to train the machine-learned, deep metric network model to identify similarities and differences between images. In some embodiments, particular features of images will be separated into dimensions (e.g., 64 dimensions) of the semantic embedding during the training of the machine-learned, deep metric network.

Further, in some embodiments, obtaining the semantic embedding associated with the target image or the respective candidate image may include a similar process to the process illustrated in FIG. 7A. For example, obtaining the semantic embedding associated with the target image may include separating the channels of the target image, obtaining a semantic embedding for each channel of the target image, and concatenating each channel of the target image into a single semantic embedding. The concatenated semantic embedding may have more dimensions than the single-channel semantic embeddings (e.g., 192 dimensions for a concatenated semantic embedding of a candidate image having three channels, each channel having a 64 dimension single-channel semantic embedding).

At block 1116, the method 1100 includes determining, by the computing device, a similarity score for each candidate image. Determining the similarity score for a respective candidate image includes computing, by the computing device, a vector distance in a multi-dimensional space described by the semantic embeddings between the respective candidate image and the target image. The similarity score for each candidate image represents a degree of similarity between the target phenotype and the respective candidate phenotype. Similar to method 1000 of FIG. 10, in some embodiments, the method 1100 may include further analysis of the similarity scores.

At block 1118, the method 1100 includes selecting, by the computing device, a preferred treatment regimen among a variety of candidate treatment regimens based on the similarity scores. For example, the candidate image having the similarity score with the largest value (or, in some embodiments, the smallest value) may be selected. The candidate image having the similarity score with the largest value may correspond to a candidate biological cell that has a candidate phenotype that is most similar to the target phenotype. If, for example, the target phenotype is healthy, and the candidate biological cells were unhealthy, the resulting greatest similarity score may correspond to a biological cell that received a candidate treatment regimen that made the cell closest to a healthy phenotype among the candidate biological cells. In another example, if the target phenotype was an unhealthy phenotype, the candidate image having the lowest similarity score may be selected, which would then correspond to a preferred treatment regimen which yields a candidate phenotype that is most dissimilar from the target phenotype.

In alternate embodiments, the method 1100 may include additional blocks. In some embodiments, for example, the method 1100 may additionally include administering the preferred treatment regimen to a patient. Administering the preferred treatment regimen to the patient may include providing an anatomical region of a patient with a treatment compound at a given concentration and/or for a given duration. The treatment compound, concentration, and/or duration may correspond to the treatment compound, concentration, and/or duration applied to the candidate biological cells in block 1104 that ultimately corresponded to the candidate image with the highest similarity score, as determined in block 1116.

III. EXAMPLE SYSTEMS

Figure 12:
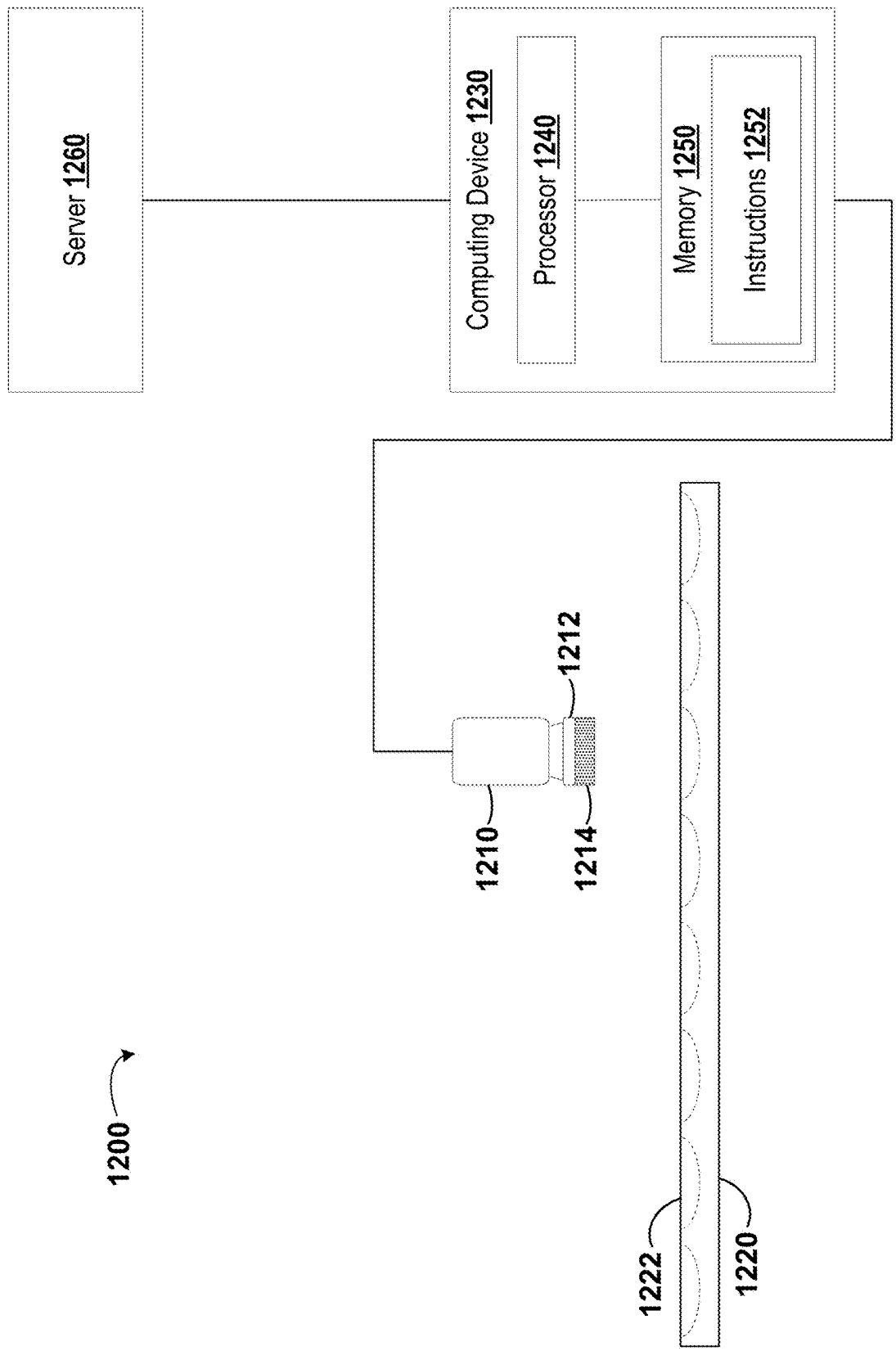
FIG. 12 is an illustration of a system, according to example embodiments.

FIG. 12 is an illustration of a system 1200, according to example embodiments. The system 1200 may include a camera 1210, a multi-well sample plate 1220, a computing device 1230 (including a processor 1240 and a memory 1250), and a server 1260. The multi-well plate 1220 may include multiple wells 1222. Further, the multi-well sample plate 1220 may be analogous to the multi-well sample plate 900 illustrated in FIG. 9.

The camera 1210 may include one or more image sensors (e.g., CCDs). The camera 1210 may also include a lens 1212 and one or more optical filters 1214. The optical filter may only pass light through to the lens 1212 within a certain wavelength range. The wavelength range may correspond to one or more targeted regions of one or more biological cells within one or more wells 1222 in the multi-well sample plate 1220. For example, a nucleus of the biological cells within one of the sample plates may be dyed using a dye of a particular color. The optical filter 1214 may then permit only wavelengths corresponding to the dye to pass to the lens 1212 of the camera 1210. In this way, only those regions of the biological cell being targeted may be recorded by the camera 1210, thereby reducing noise or unnecessary image content.

In another example embodiment, certain cellular organelles may be targeted by one or more fluorophores. The fluorophores may emit light within a first specific wavelength range when excited by radiation within a second wavelength range. Thus, in such embodiments, the system 1200 may additionally include an excitation source (e.g., a laser) that emits light within the second wavelength range to excite the fluorophores.

In some embodiments, multiple optical filters 1214 may be cascaded to absorb and/or reflect light of various wavelength ranges. Additionally or alternatively, the optical filter 1214 may be interchangeable. For example, as the camera 1210 is scanned over various wells 1222 of the multi-well sample plate 1220, the optical filter 1214 may be removed or swapped for various alternate optical filters (e.g., to analyze various targeted regions within various wells 1222 corresponding to various wavelength ranges).

As illustrated, the camera 1210 is communicatively coupled to the computing device 1230. Such a communicative coupling may be implemented using WiFi, over Bluetooth®, or via wireline interface (e.g., a USB cable), in various embodiments. Alternatively, in some embodiments, the camera 1210 may be coupled to the computing device 1230 over the public Internet. For example, the camera 1210 may be a camera attached to or integrated in a mobile computing device (e.g., a cellular phone). The mobile computing device may access the public Internet to transmit images (e.g., candidate images or target images of biological cells) to the computing device 1230. In some embodiments, the camera 1210 may additionally or alternatively be communicatively coupled to the server 1260. For example, in some embodiments, the camera 1210 may transmit images to the server 1260, the server 1260 may perform image processing (e.g., a creation of semantic embeddings using a machine-learned, deep metric network model and a comparison of the semantic embeddings to obtain similarity scores), and the server 1260 may then transmit the resulting similarity scores to the computing device 1230.

The computing device 1230, as illustrated, includes a processor 1240 and a memory 1250. The memory 1250 includes instructions 1252 stored thereon. The memory 1250 may include volatile memory (e.g., RAM) and/or non-volatile memory (e.g., a hard drive). The memory 1250 may also be internally communicatively coupled to the processor 1240 (e.g., over a system bus). The processor 1240 may be configured to execute the instructions 1252 stored in the memory 1250 (e.g., to perform various computing tasks). Additionally or alternatively, the memory 1250 may store images (e.g., recorded by the camera 1210) and semantic embeddings associated with the images. The memory 1250 may further store a machine-learned, deep metric network model used to generate semantic embeddings from images.

The computing device 1230, as illustrated, may also be communicatively coupled to the server 1260 (e.g., over the public Internet). In some embodiments, the server 1260 (alternative to or in addition to the memory 1250) may store the machine-learned, deep metric network model used to generate semantic embeddings. In such embodiments, the machine-learned, deep metric network model may be accessed by the computing device 1230 in order for the processor 1240 to generate semantic embeddings. Further, the server 1260 may store semantic embeddings generated from images (e.g., target images or candidate images). Such semantic embeddings may be generated by the server 1260, itself, or by the processor 1240 using the machine-learned, deep metric network model. The semantic embeddings may be transmitted from the server 1260 to the computing device 1230 such that the processor 1240 can perform comparisons of the semantic embeddings to obtain similarity scores. The server 1260 may also store similarity scores from previous image comparisons (e.g., comparisons performed by the processor 1240).

IV. ADDITIONAL PROCESSES

Figure 13:
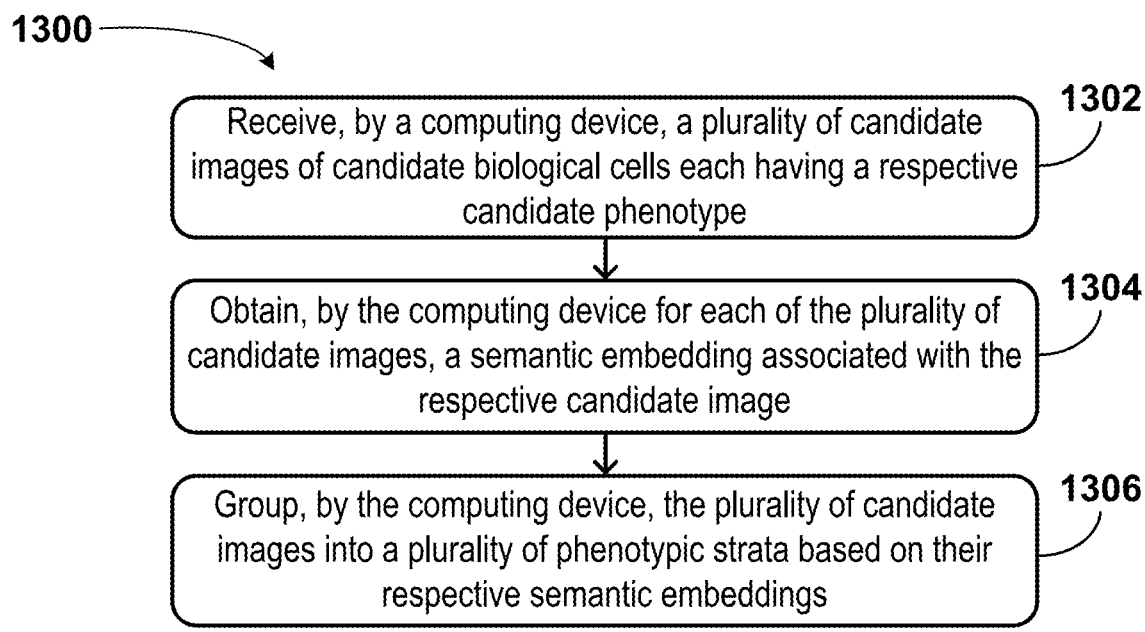
FIG. 13 is an illustration of a method, according to example embodiments.

FIG. 13 is an illustration of a method 1300, according to example embodiments. In some embodiments, various blocks may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and CD-ROM, for example. In addition, one or more blocks in FIG. 13 may represent circuitry that is wired to perform the specific logical operations.

In some embodiments, the method 1300 may include additional blocks occurring before, in between, or after the blocks illustrated in FIG. 13. Further, in some embodiments, one or more of the blocks illustrated in FIG. 13 may be repeated one or more times. In alternate embodiments, the order of various blocks within the method may be rearranged without departing from the scope of the method.

At block 1302, the method 1300 includes receiving, by a computing device, a plurality of candidate images of candidate biological cells each having a respective candidate phenotype.

At block 1304, the method 1300 includes obtaining, by the computing device for each of the plurality of candidate images, a semantic embedding associated with the respective candidate image. The semantic embedding associated with the respective candidate image is generated using a machine-learned, deep metric network model.

At block 1306, the method 1300 includes grouping, by the computing device, the plurality of candidate images into a plurality of phenotypic strata based on their respective semantic embeddings. Grouping the plurality of candidate images into the plurality of phenotypic strata based on their respective semantic embeddings includes computing, by the computing device for each candidate image, values for one or more dimensions in a multi-dimensional space described by the semantic embeddings. Grouping the plurality of candidate images into the plurality of phenotypic strata based on their respective semantic embeddings also includes comparing, by the computing device, the values for at least one of the one or more dimensions of each candidate image.

In some embodiments, the plurality of phenotypic strata may include a first phenotypic stratum and a second phenotypic stratum. Further, the first phenotypic stratum may correspond to a first stage of a disease (e.g., first stage of Parkinson's disease) and the second phenotypic stratum may correspond to a second stage of the disease (e.g., second stage of Parkinson's disease). Alternatively, in some embodiments, the first phenotypic stratum may correspond to a first type of a disease (e.g., Hemoglobin SS form of sickle cell disease (i.e., sickle cell anemia) or sporadic Parkinson's disease) and the second phenotypic stratum may correspond to a second type of the disease (e.g., Hemoglobin SC form of sickle cell disease or familial genetic Parkinson's disease).

Additionally or alternatively, in some embodiments, grouping the plurality of candidate images into the plurality of phenotypic strata based on their respective semantic embeddings may include determining, based on the values for at least one of the one or more dimensions, a threshold value for the at least one dimension. The threshold value may delineate between a first phenotypic stratum and a second phenotypic stratum.

Figure 14:
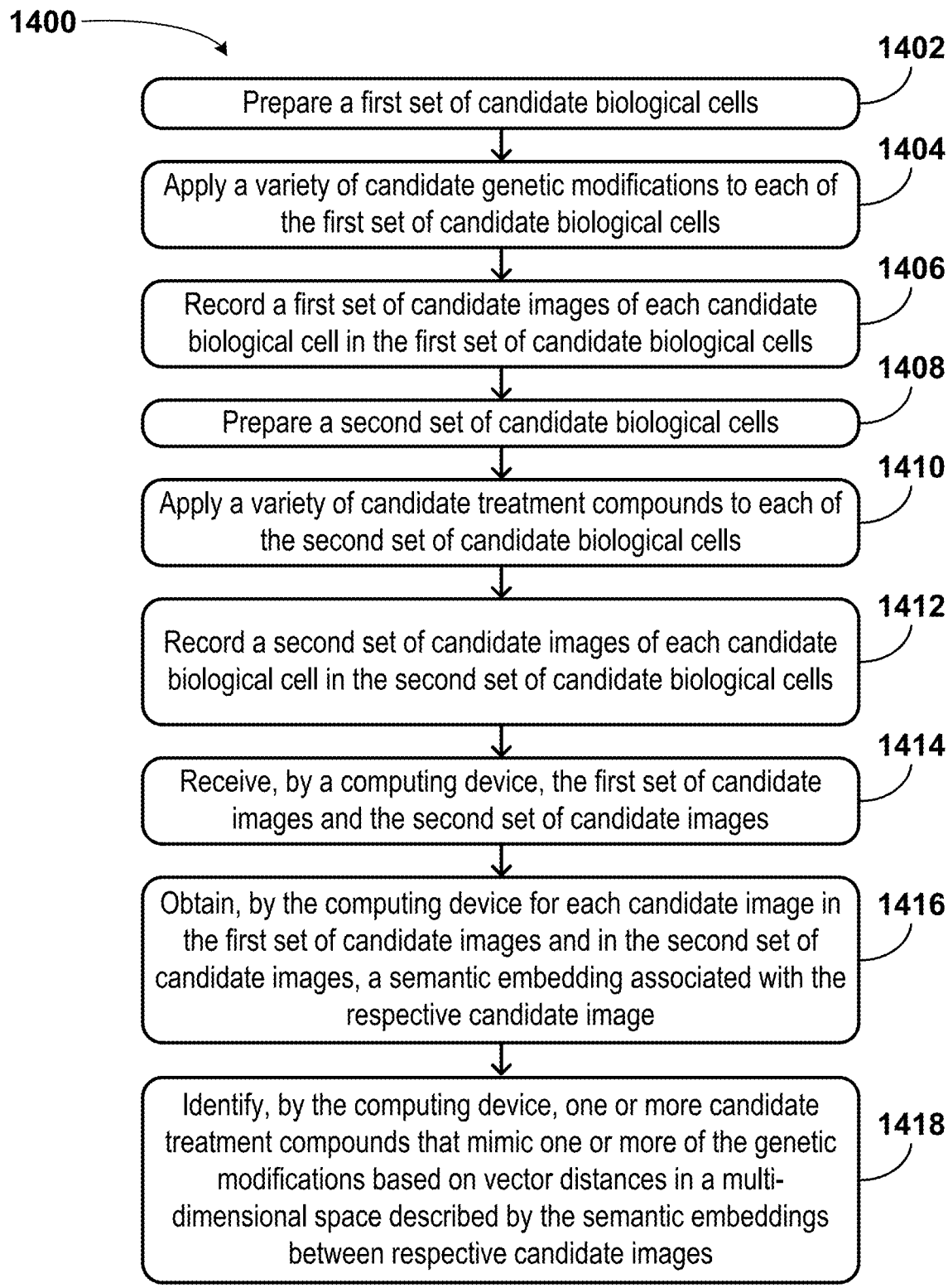
FIG. 14 is an illustration of a method, according to example embodiments.

FIG. 14 is an illustration of a method 1400, according to example embodiments. In some embodiments, various blocks may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and CD-ROM, for example. In addition, one or more blocks in FIG. 14 may represent circuitry that is wired to perform the specific logical operations.

In some embodiments, the method 1400 may include additional blocks occurring before, in between, or after the blocks illustrated in FIG. 14. Further, in some embodiments, one or more of the blocks illustrated in FIG. 14 may be repeated one or more times. In alternate embodiments, the order of various blocks within the method may be rearranged without departing from the scope of the method.

At block 1402, the method 1400 includes preparing a first set of candidate biological cells.

At block 1404, the method 1400 includes applying a variety of candidate genetic modifications to each of the first set of candidate biological cells.

At block 1406, the method 1400 includes recording a first set of candidate images of each candidate biological cell in the first set of candidate biological cells. Each candidate biological cell in the first set of candidate biological cells has a respective candidate phenotype arising in response to the candidate genetic modification being applied.

At block 1408, the method 1400 includes preparing a second set of candidate biological cells.

At block 1410, the method 1400 includes applying a variety of candidate treatment compounds to each of the second set of candidate biological cells.

At block 1412, the method 1400 includes recording a second set of candidate images of each candidate biological cell in the second set of candidate biological cells. Each candidate biological cell in the second set of candidate biological cells has a respective candidate phenotype arising in response to the candidate treatment compound being applied.

At block 1414, the method 1400 includes receiving, by a computing device, the first set of candidate images and the second set of candidate images.

At block 1416, the method 1400 includes obtaining, by the computing device for each candidate image in the first set of candidate images and in the second set of candidate images, a semantic embedding associated with the respective candidate image. The semantic embedding associated with the respective candidate image is generated using a machine-learned, deep metric network model.

At block 1418, the method 1400 includes identifying, by the computing device, one or more candidate treatment compounds that mimic one or more of the genetic modifications based on vector distances in a multi-dimensional space described by the semantic embeddings between respective candidate images.

Figure 15:
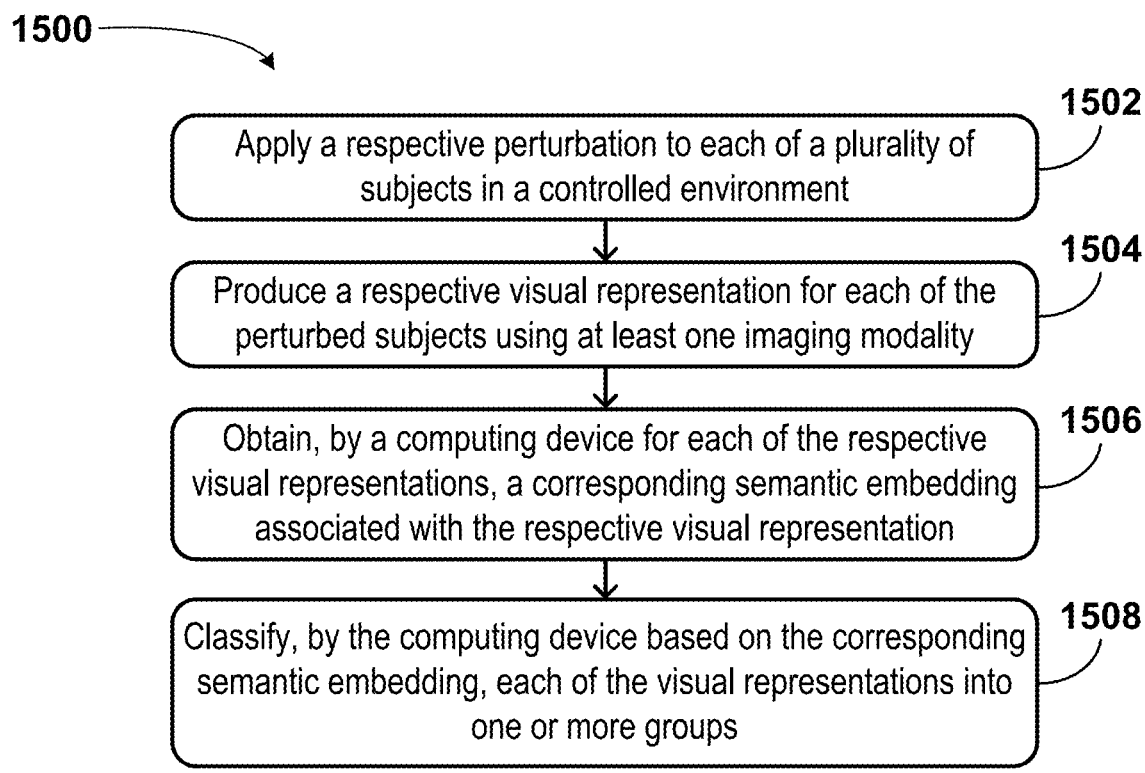
FIG. 15 is an illustration of a method, according to example embodiments.

FIG. 15 is an illustration of a method 1500, according to example embodiments. In some embodiments, various blocks may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and CD-ROM, for example. In addition, one or more blocks in FIG. 15 may represent circuitry that is wired to perform the specific logical operations.

In some embodiments, the method 1500 may include additional blocks occurring before, in between, or after the blocks illustrated in FIG. 15. Further, in some embodiments, one or more of the blocks illustrated in FIG. 15 may be repeated one or more times. In alternate embodiments, the order of various blocks within the method may be rearranged without departing from the scope of the method.

At block 1502, the method 1500 includes applying a respective perturbation to each of a plurality of subjects in a controlled environment.

At block 1504, the method 1500 includes producing a respective visual representation for each of the perturbed subjects using at least one imaging modality.

At block 1506, the method 1500 includes obtaining, by a computing device for each of the respective visual representations, a corresponding semantic embedding associated with the respective visual representation. The semantic embedding associated with the respective visual representation is generated using a machine-learned, deep metric network model.

At block 1508, the method 1500 includes classifying, by the computing device based on the corresponding semantic embedding, each of the visual representations into one or more groups.

In some embodiments of the method 1500, the at least one imaging modality may include computed tomography, magnetic resonance imaging, positron emission tomography, ultrasound, x-ray computed tomography, x-ray diffraction, fluoroscopy, projectional radiography, single-photon emission computed tomography, scintigraphy, elastography, photoacoustic imaging, near-infrared spectroscopy, magnetic particle imaging, optoacoustic imaging, diffuse optical tomography, Raman spectroscopy, fluorescent microscopy, confocal microscopy, two-photon microscopy, hyperspectral analysis, transmission microscopy, electromagnetic scanning, differential interference contrast microscopy, multiphoton microscopy, dark-field microscopy, quantitative phase-contrast microscopy, near-field scanning optical microscopy, photo-activated localization microscopy, second harmonic imaging, holography, scanning electron microscopy, and/or tunneling electron microscopy.

In some embodiments of the method 1500, the plurality of subjects may include biological cells, fibroblasts, malaria cells, yeast cells, yeast cultures, bacteria, bacterial cultures, fungus, fungal cultures, cancer cells, blood cells, malarial parasites, mitochondria, nuclei, axons, dendrites, induced pluripotent stem cells, biological cells from a given region of an organism, biological cells from a given tissue of an organism, biological cells from a given organ of an organism, biological cells from a given system of an organism, biological cell ensembles, tissues, organs, organoids, biological systems, organisms, groups of organisms, ecosystems, chemical compounds, crystals, metallic glasses, mixtures of metallic salts, semiconductors, metals, dielectrics, graphene, microelectromechanical systems (MEMS), and/or nanoelectromechanical systems (NEMS).

In some embodiments of the method 1500, applying the respective perturbation to each of the plurality of subjects includes at least one of: adding one or more small molecule compounds to at least one of the plurality of subjects; applying a candidate treatment compound to at least one of the plurality of subjects; applying a genetic modification to at least one of the plurality of subjects; allowing a predetermined amount of time to elapse for at least one of the plurality of subjects; illuminating at least one of the plurality of subjects with light of a predetermined wavelength; heating or cooling at least one of the plurality of subjects to a predetermined temperature; exposing at least one of the plurality of subjects to another subject of the plurality of subjects; introducing at least one of the plurality of subjects to a different environment; or applying a predetermined force to one or more regions of at least one of the plurality of subjects.

In some embodiments of the method 1500, each of the respective visual representations may include a three-dimensional visual representation. Additionally or alternatively, the machine-learned, deep metric network model may be trained using three-dimensional training data.

In some embodiments of the method 1500, each of the respective visual representations may include a videographic representation. Additionally or alternatively, the machine-learned, deep metric network model was trained using videographic training data.

In some embodiments of the method 1500, producing the respective visual representations may include performing a patch selection to identify each of the respective perturbed subjects. In some embodiments, the patch selection may be machine-learned and/or may include an attention mechanism used to define which regions of a preliminary visual representation are of threshold interest level to be selected by the patch selection.

In some embodiments of the method 1500, obtaining the corresponding semantic embedding associated with the respective visual representations may include incorporating data captured during one or more respective supplementary measurements of a given measurement type. In some embodiments, the data captured during one or more respective supplementary measurements may include experimental metadata (e.g., information about how the experiment was performed, in what spatial location the experiment was performed, subject provenance for subjects of the experiment, or preparation history for the experiment), transcriptomic data, genomic data, proteomic data, metabolomic data, lipidomic data, bulk semiconductor material properties, and/or patient diagnostic data.

Additionally or alternatively, the machine-learned, deep metric network model may be trained using training data that includes data of the given measurement type. Each visual representation may include a plurality of channels. Further, incorporating data captured during one or more respective supplementary measurements may include: retrieving, by the computing device, each channel of the respective visual representation; generating, by the computing device using the machine-learned, deep metric network model, a respective single-channel semantic embedding for each channel of the respective visual representation; generating, by the computing device using the machine-learned, deep metric network model, an additional single-channel semantic embedding for the data captured during one or more respective supplementary measurements; and concatenating, by the computing device, the single-channel semantic embeddings for each channel of the respective visual representation with the additional single-channel semantic embedding into a multi-channel semantic embedding.

In other embodiments, the machine-learned, deep metric network model may be trained using training data that includes data of the given measurement type. Further, incorporating data captured during one or more respective supplementary measurements may include: generating a first preliminary semantic embedding for the respective visual representation using the machine-learned, deep metric network model; generating a second preliminary semantic embedding for the data captured during one or more respective supplementary measurements using the machine-learned, deep metric network model; and generating a composite semantic embedding using an additional machine-learned model. The composite semantic embedding may include a hybrid of the first preliminary semantic embedding and the second preliminary semantic embedding.

In still other embodiments, the machine-learned, deep metric network model was trained using training data that includes data of the given measurement type. Further, incorporating data captured during one or more respective supplementary measurements may include: generating a first preliminary semantic embedding for the respective visual representation using the machine-learned, deep metric network model; generating a second preliminary semantic embedding for the data captured during one or more respective supplementary measurements using the machine-learned, deep metric network model; and generating a composite semantic embedding by applying a mathematical operation to corresponding dimensions of the first preliminary semantic embedding and the second preliminary semantic embedding.

In some embodiments of the method 1500, classifying each of the visual representations into one or more groups includes performing vector arithmetic on the corresponding semantic embedding to determine to which of the one or more groups the respective visual representation belongs.

In some embodiments of the method 1500, classifying each of the visual representations into one or more groups includes applying a classification model to each of the corresponding semantic embeddings. The classification model may be trained to identify responses to the respective perturbations and disregard statistical variations present across the plurality of subjects.

Additionally or alternatively, the classification model may be trained using a human-in-the-loop procedure to identify which variations correspond to notable differences and which variations are attributable to randomness.

In some embodiments of the method 1500, classifying the visual representations into one or more groups may include: identifying one or more values corresponding to one or more respective dimensions of the semantic embedding associated with the respective visual representation; and determining, based on the one or more values, to which of an enumerated list of groups the respective visual representation belongs.

In some embodiments of the method 1500, classifying the visual representations into one or more groups may include extracting information about the respective visual representation based on a topology within the semantic embedding associated with the respective visual representation. The topology may have been enforced during training of the machine-learned, deep metric network model. Further, in some embodiments, the topology is linear, elliptical, circular, polygonal, spherical, ellipsoidal, cylindrical, conical, hyperboloidal, paraboloidal, toroidal, pyramidal, polyhedral, or defined in a dimensional space having greater than three dimensions.

In some embodiments of the method 1500, the machine-learned, deep metric network model is trained using a plurality of photographic images as training data. Further, the photographic images may be query results ranked based on selections. Additionally, rankings of the photographic images may be used in the training of the machine-learned, deep metric network model to determine image similarity between two images.

In some embodiments, the method 1500 may also include training the machine-learned, deep metric network model. Training the machine-learned, deep metric network model may include receiving, by the computing device, a series of three-image sets as training data. Each three-image set may include a query image, a positive image, and a negative image. Further, the query image, the positive image, and the negative image may be query results ranked in comparison with one another based on selections. Additionally, the selections may indicate that a similarity between the query image and the positive image is greater than a similarity between the query image and the negative image. Still further, training the machine-learned, deep metric network model may include refining, by the computing device, the machine-learned, deep metric network model based on each three-image set to account for image components of the query image, the positive image, and the negative image.

In some embodiments, the method 1500 may include determining, by the computing device, a preferred perturbation from among the respective perturbations based on the one or more groups into which each of the visual representations are classified.

Figure 16:
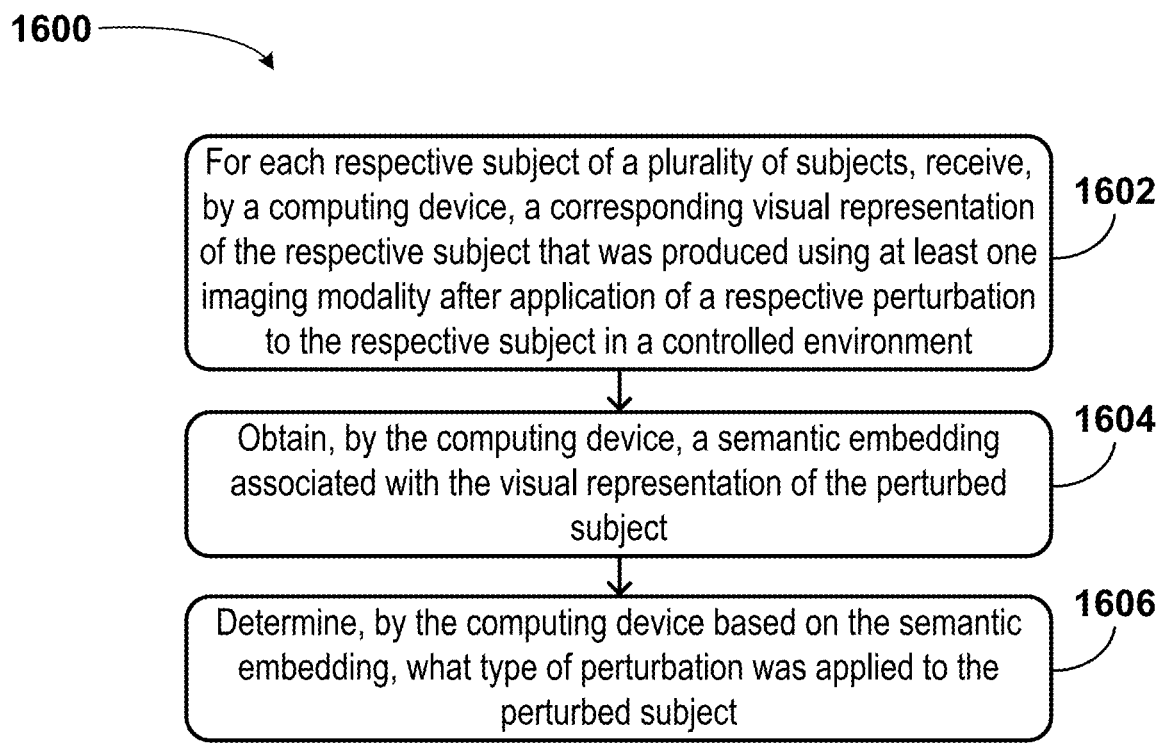
FIG. 16 is an illustration of a method, according to example embodiments.

FIG. 16 is an illustration of a method 1600, according to example embodiments. In some embodiments, various blocks may represent a module, a segment, or a portion of program code, which includes one or more instructions executable by a processor or computing device for implementing specific logical operations or steps. The program code may be stored on any type of computer-readable medium, such as a storage device included in a disk or hard drive. The computer-readable medium may include volatile memory, such as a register memory, a processor cache, and/or a RAM. Additionally or alternatively, the computer-readable medium may include non-volatile memory, such as secondary or persistent long-term storage, like ROM, optical or magnetic disks, and CD-ROM, for example. In addition, one or more blocks in FIG. 16 may represent circuitry that is wired to perform the specific logical operations.

In some embodiments, the method 1600 may include additional blocks occurring before, in between, or after the blocks illustrated in FIG. 16. Further, in some embodiments, one or more of the blocks illustrated in FIG. 16 may be repeated one or more times. In alternate embodiments, the order of various blocks within the method may be rearranged without departing from the scope of the method.

At block 1602, the method 1600 includes, for each respective subject of a plurality of subjects, receiving, by a computing device, a corresponding visual representation of the respective subject that was produced using at least one imaging modality after application of a respective perturbation to the respective subject in a controlled environment.

At block 1604, the method 1600 includes obtaining, by the computing device, a semantic embedding associated with the visual representation of the perturbed subject. The semantic embedding associated with the visual representation of the perturbed subject is generated using a machine-learned, deep metric network model.

At block 1606, the method 1600 includes determining, by the computing device based on the semantic embedding, what type of perturbation was applied to the perturbed subject.

V. CONCLUSION

The above detailed description describes various features and functions of the disclosed systems, devices, and methods with reference to the accompanying figures. While various aspects and embodiments have been disclosed herein, other aspects and embodiments will be apparent. The various aspects and embodiments disclosed herein are for purposes of illustration only and are not intended to be limiting, with the true scope being indicated by the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be used, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed:
1. A method, comprising:
  receiving, by a computing device, a target image of a target biological cell having a target phenotype;
  obtaining, by the computing device, a semantic embedding associated with the target image, wherein the semantic embedding associated with the target image is generated using a machine-learned, deep metric network model;
  obtaining, by the computing device for each of a plurality of candidate images of candidate biological cells each having a respective candidate phenotype, a semantic embedding associated with the respective candidate image, wherein the semantic embedding associated with the respective candidate image is generated using the machine-learned, deep metric network model;
  identifying, by the computing device for each of the semantic embeddings, common morphological variations;
  reducing, by the computing device for each of the semantic embeddings based on the identified common morphological variations, effects of nuisances; and determining, by the computing device, a similarity score for each candidate image, wherein the similarity score for each candidate image represents a degree of similarity between the target phenotype and the respective candidate phenotype.

2. The method of claim 1, wherein the machine-learned, deep metric network model was trained using a plurality of photographic images as training data, wherein the photographic images are query results ranked based on selections, and wherein rankings of the photographic images are used in the training of the machine-learned, deep metric network model to determine image similarity between two images.

3. The method of claim 1, further comprising training the machine-learned, deep metric network model, wherein training the machine-learned, deep metric network model comprises:

receiving, by the computing device, a series of three-image sets as training data, wherein each three-image set comprises a query image, a positive image, and a negative image, wherein the query image, the positive image, and the negative image are query results ranked in comparison with one another based on selections, and wherein the selections indicate that a similarity between the query image and the positive image is greater than a similarity between the query image and the negative image; and refining, by the computing device, the machine-learned, deep metric network model based on each three-image set to account for image components of the query image, the positive image, and the negative image.

4. The method of claim 1, further comprising:

determining, by the computing device, a threshold similarity score; and determining, by the computing device, those candidate images having similarity scores greater than or equal to the threshold similarity score.

5. The method of claim 4, wherein the target phenotype is a healthy phenotype, wherein the candidate images having similarity scores greater than or equal to the threshold similarity score have respective candidate phenotypes corresponding to the healthy phenotype, and wherein those candidate images having similarity scores less than the threshold similarity score have respective candidate phenotypes corresponding to an unhealthy phenotype.

6. The method of claim 4, wherein the target phenotype is an unhealthy phenotype, wherein the candidate images having similarity scores greater than or equal to the threshold similarity score have respective candidate phenotypes corresponding to the unhealthy phenotype, and wherein those candidate images having similarity scores less than the threshold similarity score have respective candidate phenotypes corresponding to a healthy phenotype.

7. The method of claim 1, further comprising:

determining, by the computing device, a maximum similarity score among all of the candidate images, wherein the maximum similarity score corresponds to a candidate image of a candidate biological cell having a candidate phenotype that is most similar to the target phenotype.

8. The method of claim 7, further comprising:

determining, by the computing device, a treatment regimen for a patient based on the candidate biological cell having the candidate phenotype that is most similar to the target phenotype.

9. The method of claim 1, wherein identifying the common morphological variations comprises obtaining, by the computing device for each of a plurality of control group images of control group biological cells having control group phenotypes, a semantic embedding associated with the respective control group image, wherein the semantic embedding associated with the respective control group image is generated using the machine-learned, deep metric network model, wherein reducing the effects of nuisances comprises normalizing, by the computing device, the semantic embeddings associated with the candidate images, and wherein normalizing comprises:

computing, by the computing device, eigenvalues and eigenvectors of a covariance matrix defined by the values of each dimension of the semantic embeddings associated with the control group images using principal component analysis;

scaling, by the computing device, values of each dimension of the semantic embeddings associated with the control group images by a respective dimensional scaling factor such that each dimension is zero-centered and has unit variance; and scaling, by the computing device, values of each corresponding dimension of the semantic embeddings associated with the candidate images by the respective dimensional scaling factor.

10. The method of claim 9, wherein normalizing, by the computing device, the semantic embeddings associated with the candidate images negates an influence of the common morphological variations on the similarity scores.

11. The method of claim 10, wherein the common morphological variations comprise variations in cellular size, variations in nuclear size, variations in cellular shape, variations in nuclear shape, variations in nuclear color, variations in nuclear size relative to cellular size, or variations in nuclear location within a respective cell.

12. The method of claim 1, further comprising:

obtaining the candidate biological cells, wherein the candidate biological cells initially exhibit unhealthy phenotypes;

treating the candidate biological cells with various concentrations of various candidate treatment compounds;

recording the candidate images of the candidate biological cells; and transmitting the plurality candidate images to the computing device.

13. The method of claim 1, wherein the target biological cell was acquired from a first anatomical region of a patient during a biopsy, and wherein the candidate biological cells comprise biological cells acquired from anatomical regions of the patient during the biopsy other than the first anatomical region.

14. The method of claim 1, wherein the semantic embedding associated with the target image and the semantic embeddings associated with the candidate images comprise 64-dimensional embeddings for each channel of a corresponding image.

15. The method of claim 1, further comprising:

scaling, by the computing device, the target image and each of the candidate images such that an image size of the target image and images sizes of each of the candidate images match an image size interpretable using the machine-learned, deep metric network model.

16. The method of claim 15, wherein scaling the target image and each of the candidate images comprises, for each respective image:
    determining, by the computing device, a location of a cellular nucleus within the respective image; and
    cropping, by the computing device, the respective image based on a rectangular box centered on the cellular nucleus.

17. The method of claim 1, wherein obtaining the semantic embedding associated with the target image or one of the respective candidate images comprises:
    retrieving, by the computing device, each channel of a respective image;
    obtaining, by the computing device, a semantic embedding for each channel of the respective image, wherein the semantic embedding for each channel of the respective image is generated using the machine-learned, deep metric network model; and
    concatenating, by the computing device, the semantic embeddings for each channel of the respective image into a single semantic embedding.

18. The method of claim 17,
    wherein each channel in the target image and each of the candidate images corresponds to a predetermined range of wavelengths detectable by one or more cameras, each having one or more associated optical filters,
    wherein each of the one or more cameras is configured to record the target image or at least one of the plurality of candidate images, and
    wherein one or more investigated regions of the target biological cell or the candidate biological cells emit light within the predetermined ranges of wavelengths.

19. The method of claim 18, wherein the one or more investigated regions of the target biological cell or the candidate biological cells emit light within the predetermined ranges of wavelengths due to a fluorescent compound that targets the one or more investigated regions and is excited by an electromagnetic excitation source, a chemical dye that targets the one or more investigated regions, or a chemiluminescent compound that targets the one or more investigated regions.

20. The method of claim 18, wherein the one or more investigated regions correspond to a location of a nucleus, a nucleolus, a cytoskeleton, a mitochondrion, a cellular membrane, an endoplasmic reticulum, a golgi body, a ribosome, a vesicle, a vacuole, a lysosome, or a centrosome within the target biological cell or the candidate biological cells.

21. The method of claim 1, wherein the plurality of candidate cells each correspond to a candidate mechanism of action.

22. The method of claim 1,
    wherein obtaining, by the computing device, the semantic embedding associated with the target image comprises generating, by an autoencoder, the semantic embedding associated with the target image, and
    wherein obtaining, by the computing device for each candidate image, the semantic embedding associated with the respective candidate image comprises generating, by the autoencoder for each candidate image, the semantic embedding associated with the respective candidate image.

23. A non-transitory, computer-readable medium having instructions stored thereon, wherein the instructions, when executed by a processor, cause the processor to execute a method, comprising:
    receiving, by the processor, a target image of a target biological cell having a target phenotype;
    obtaining, by the processor, a semantic embedding associated with the target image, wherein the semantic embedding associated with the target image is generated using a machine-learned, deep metric network model;
    obtaining, by the processor for each of a plurality of candidate images of candidate biological cells each having a respective candidate phenotype, a semantic embedding associated with the respective candidate image, wherein the semantic embedding associated with the respective candidate image is generated using the machine-learned, deep metric network model;
    identifying, by the processor for each of the semantic embeddings, common morphological variations;
    reducing, by the processor for each of the semantic embeddings based on the identified common morphological variations, effects of nuisances; and
    determining, by the processor, a similarity score for each candidate image,
    wherein the similarity score for each candidate image represents a degree of similarity between the target phenotype and the respective candidate phenotype.

24. A method, comprising:
    preparing a multi-well sample plate with a target biological cell having a target phenotype and candidate biological cells;
    applying a variety of candidate treatment regimens to each of the candidate biological cells;
    recording a target image of the target biological cell;
    recording candidate images of each of the candidate biological cells, each having a respective candidate phenotype arising in response to the candidate treatment regimen being applied;
    receiving, by a computing device, the target image and the candidate images;
    obtaining, by the computing device, a semantic embedding associated with the target image, wherein the semantic embedding associated with the target image is generated using a machine-learned, deep metric network model;
    obtaining, by the computing device for each candidate image, a semantic embedding associated with the respective candidate image, wherein the semantic embedding associated with the respective candidate image is generated using the machine-learned, deep metric network model;
    identifying, by the computing device for each of the semantic embeddings, common morphological variations;
    reducing, by the computing device for each of the semantic embeddings based on the identified common morphological variations, effects of nuisances;
    determining, by the computing device, a similarity score for each candidate image,
    wherein the similarity score for each candidate image represents a degree of similarity between the target phenotype and the respective candidate phenotype; and
    selecting, by the computing device, a preferred treatment regimen among the variety of candidate treatment regimens based on the similarity scores.

* * * * *